(12) United States Patent
Cheng et al.

(10) Patent No.: US 10,907,185 B2
(45) Date of Patent: *Feb. 2, 2021

(54) ENZYMATIC SYNTHESIS OF SOLUBLE GLUCAN FIBER

(71) Applicant: DUPONT INDUSTRIAL BIOSCIENCES USA, LLC, Wilmington, DE (US)

(72) Inventors: Qiong Cheng, Wilmington, DE (US); Robert Dicosimo, Chadds Ford, PA (US); Arthur Ouwehand, Inga (FI); Zheng You, Wilmington, DE (US); Jian Ping Lai, Wallingford, PA (US); Zheyong Yu, Shanghai (CN); Zhenghong Zhang, Shanghai (CN)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/313,321

(22) PCT Filed: May 22, 2015

(86) PCT No.: PCT/US2015/032139
§ 371 (c)(1),
(2) Date: Nov. 22, 2016

(87) PCT Pub. No.: WO2015/183726
PCT Pub. Date: Dec. 3, 2015

(65) Prior Publication Data
US 2017/0198324 A1 Jul. 13, 2017

Related U.S. Application Data

(60) Provisional application No. 62/004,314, filed on May 29, 2014.

(51) Int. Cl.
| | | |
|---|---|---|
| *C12P 19/18* | (2006.01) | |
| *A21D 13/40* | (2017.01) | |
| *A23C 9/123* | (2006.01) | |
| *A23G 3/36* | (2006.01) | |
| *A23L 2/52* | (2006.01) | |
| *A61K 31/721* | (2006.01) | |
| *C08B 37/00* | (2006.01) | |
| *A23L 29/269* | (2016.01) | |
| *A23L 33/21* | (2016.01) | |
| *C12P 19/08* | (2006.01) | |
| *A61K 8/73* | (2006.01) | |
| *A61Q 19/00* | (2006.01) | |
| *C12P 19/04* | (2006.01) | |

(Continued)

(52) U.S. Cl.
CPC ............. *C12P 19/18* (2013.01); *A21D 13/40* (2017.01); *A23C 9/123* (2013.01); *A23G 3/36* (2013.01); *A23G 9/32* (2013.01); *A23L 2/52* (2013.01); *A23L 7/126* (2016.08); *A23L 7/135* (2016.08); *A23L 21/10* (2016.08); *A23L 29/273* (2016.08); *A23L 33/21* (2016.08); *A61K 8/73* (2013.01); *A61K 31/716* (2013.01); *A61K 31/721* (2013.01); *A61Q 19/00* (2013.01); *C08B 37/0009* (2013.01); *C08L 5/00* (2013.01); *C12P 19/04* (2013.01); *C12P 19/08* (2013.01); *C12Y 204/01* (2013.01); *C12Y 204/01005* (2013.01); *A23V 2002/00* (2013.01); *A61K 2800/10* (2013.01); *A61K 2800/85* (2013.01); *C08L 2205/16* (2013.01)

(58) Field of Classification Search
CPC ...... C12P 19/18; C12P 19/08; C08B 37/0009; C12Y 204/01005; C12Y 204/01; A61K 31/721; A61K 8/73; A61K 2800/85; A61K 2800/10; A61Q 19/00; A23L 29/273; A23L 33/21; A23L 2/52; A23L 7/126; A23L 7/135; A23L 21/10; A23C 9/123; A21D 13/40; A23G 3/36; A23G 9/32; A23V 2002/00
USPC .......................................................... 514/59
See application file for complete search history.

(56) References Cited

U.S. PATENT DOCUMENTS

| | | | |
|---|---|---|---|
| 2,709,150 A | 5/1955 | Virginia et al. | |
| 2,776,925 A | 1/1957 | Corman et al. | |

(Continued)

FOREIGN PATENT DOCUMENTS

| | | | |
|---|---|---|---|
| EP | 1151085 B1 | 8/2005 | |
| EP | 2365084 A2 | 9/2011 | |

(Continued)

OTHER PUBLICATIONS

Ruhmkorf et al. Identification of Lactobacillus curvatus TMW 1.624 dextransucrase and comparative characterization with Lactobacillus reuteri TMW 1.106 and Lactobacillus animalis TMW 1.971 dextransucrases. Food Microbiology 34 (2013) 52-61. Available online Nov.29, 2012. (Year: 2012).*

(Continued)

*Primary Examiner* — Yih-Horng Shiao
(74) *Attorney, Agent, or Firm* — Thomas Malone

(57) ABSTRACT

An enzymatically produced soluble α-glucan fiber composition is provided suitable for use as a digestion resistant fiber in food and feed applications. The soluble α-glucan fiber composition can be blended with one or more additional food ingredients to produce fiber-containing compositions. Methods for the production and use of compositions comprising the soluble α-glucan fiber are also provided.

7 Claims, No Drawings
Specification includes a Sequence Listing.

(51) Int. Cl.
C08L 5/00 (2006.01)
A61K 31/716 (2006.01)
A23L 7/135 (2016.01)
A23L 7/126 (2016.01)
A23L 21/10 (2016.01)
A23G 9/32 (2006.01)

(56) References Cited

U.S. PATENT DOCUMENTS

| | | | |
|---|---|---|---|
| 4,649,058 | A | 3/1987 | Schwengers |
| 4,861,381 | A | 8/1989 | Paul et al. |
| 5,141,858 | A | 8/1992 | Paul et al. |
| 6,486,314 | B1 | 11/2002 | Van Geel-Schutten et al. |
| 6,630,586 | B1 | 10/2003 | Fouache et al. |
| 6,867,026 | B2 | 3/2005 | Van Geel-Schutten et al. |
| 7,402,420 | B2 | 7/2008 | Kossmann et al. |
| 7,439,049 | B2 | 10/2008 | Bozonet et al. |
| 7,524,645 | B2 | 4/2009 | Monsan et al. |
| 7,612,198 | B2 | 11/2009 | Fuertes et al. |
| 7,897,373 | B2 | 3/2011 | Monsan et al. |
| 8,057,840 | B2 | 11/2011 | Harrison et al. |
| 8,192,956 | B2 | 6/2012 | Kim et al. |
| 10,351,633 | B2 * | 7/2019 | Cheng ............... A23L 33/21 |
| 2005/0059633 | A1 | 3/2005 | Van Geel-Schutten et al. |
| 2009/0123448 | A1 | 5/2009 | Bozonnet et al. |
| 2009/0297663 | A1 | 12/2009 | Van Geel-Schutten et al. |
| 2009/0300798 | A1 | 12/2009 | Kok-Jacon et al. |
| 2010/0047432 | A1 | 2/2010 | Harrison et al. |
| 2010/0122378 | A1 | 5/2010 | Frohberg et al. |
| 2010/0284972 | A1 * | 11/2010 | Naeye ............... A61K 31/733 424/93.3 |
| 2011/0020496 | A1 | 1/2011 | Shimada et al. |
| 2011/0081474 | A1 | 4/2011 | Zhou et al. |
| 2011/0178289 | A1 | 7/2011 | Monsan et al. |
| 2012/0034366 | A1 | 2/2012 | Hoffman et al. |
| 2012/0165290 | A1 | 6/2012 | Dijkhuizen et al. |
| 2014/0087431 | A1 | 3/2014 | Payne et al. |

FOREIGN PATENT DOCUMENTS

| | | |
|---|---|---|
| JP | 2001258589 | 9/2001 |
| JP | 2007181452 A | 7/2007 |
| JP | 4473402 B2 | 6/2010 |
| WO | 03008618 A2 | 1/2003 |
| WO | 2006054474 | 5/2006 |
| WO | 2010129839 A1 | 11/2010 |
| WO | 2013036918 A1 | 3/2013 |
| WO | 2015183714 A1 | 12/2015 |
| WO | 2015183721 A1 | 12/2015 |
| WO | 2015183722 A1 | 12/2015 |
| WO | 2015183724 A1 | 12/2015 |
| WO | 2015183729 A1 | 12/2015 |

OTHER PUBLICATIONS

OM protein—protein search, using sw model. Run on: Aug. 23, 2018. Document: US-15-313-321-1 (Year: 2018).*

OM protein—protein search, using sw model. Run on: Aug. 23, 2018. Document: US-15-313-321-3 (Year: 2018).*

Arguello-Morales et al., 'Proteolytic modification of Leuconostoc mesenteroides B-512F dextransucrase,' Antonie Van Leeuwenhoek, Feb. 1, 2005, vol. 87, No. 2, pp. 131-141.

Bozonnet et al., 'Molecular characterization of DSR-E, an -1,2 linkage-synthesizing dextransucrase with two catalytic domains,' Journal of Bacteriology, Oct. 15, 2002, vol. 184, No. 20, pp. 5753-5761.

Brison et al., 'Synthesis of dextrans with controlled amounts of [alpha]-1,2 linkages using the transglucosidase GBD-CD2,' Applied Microbiology and Biotechnology, Oct. 16, 2009, vol. 86, No. 2, pp. 545-554.

Brison et al., 'Functional and structural characterization of alpha-(1-2) branching sucrase derived from DSR-E glucansucrase,' J. Biol. Chem., Mar. 9, 2012, vol. 287(11), pp. 7915-7924.

Fabre et al., 'Role of the two catalytic domains of DSR-E dextransucrase and their involvement in the formation of highly alpha-1,2 branched dextran,' Journal of Bacteriology, Jan. 1, 2005, vol. 187, No. 1, pp. 296-303.

Fuglsang et al., 'Biochemical analysis of recombinant fungal mutanases,' J. Biol. Chem., 2000, vol. 275, pp. 2009-2018.

Goulas et al., 'Synthesis of isomaltooligosaccharides and oligodextrans by the combined use of dextransucrase and dextranase,' Enzyme and Microbial Technology, 2004, vol. 35, pp. 327-338.

Hakamada et al., 'Nucleotide and deduced amino acid sequences of mutanase-like genes from Paenibacillus isolates: Proposal of a new family of glycoside hydrolases,' Biochimie, 2008, vol. 90, pp. 525-533.

Hayacibara et al., 'The Influence of Mutanase and Dextranase on the production and structure of glucans synthesized by streptococcal glucosyltransferases,' Carbohydrate Research, Pergamon, GB, Aug. 23, 2004, vol. 339, No. 12, pp. 2127-2137.

Hee-Kyoung et al., 'Functional, genetic and bioinformatic characterization of dextransucrase (DSRBCB4) gene in Leuconostoc mesenteroides B-1299CB4,' Journal of Microbiology and Biotechnology, Jun. 2008, vol. 18, No. 6, pp. 1050-1058.

Igarashi et al., 'Molecular characterization of dextranase from Streptococcus rattus,' Microbiol. Immunol., 2004, vol. 48, pp. 155-162.

Jeanes et al., 'Characterization and classification of dextrans from ninety-six strains of bacteria,' Journal of the American Chemical Society, Oct. 20, 1954, vol. 76, pp. 5041-5052.

Kang et al., 'Molecular characterization and expression analysis of the glucansucrase DSRWC from Weissella cibaria synthesizing a $\alpha(1\rightarrow6)$ glucan,' Fems Microbiology Letters, Mar. 1, 2009, vol. 292, No. 1, pp. 33-41.

Kang et al., 'Cloning and characterization of a dextranase gene from Lipomyces starkeyi and its expression in Saccharomyces cerevisiae,' Yeast, 2005, vol. 22, pp. 1239-1248.

Kralj et al., 'Glucan synthesis in the genus Lactobacillus: isolation and characterization of glucansucrase genes, enzymes and glucan products from six different strains,' Microbiology, Nov. 1, 2004, vol. 150, No. Part 11, pp. 3681-3690.

Khalikova et al., 'Microbial Dextran-Hydrolyzing Enzymes: Fundamentals and Applications,' Microbiology and Molecular Biology Reviews, Jun. 1, 2005, pp. 306-325.

Larsson et al., 'Dextranase from penicillium minioluteum: reaction course, crystal structure, and product complex,' Structure, 2003, vol. 11, pp. 1111-1121.

Leemhuis et al., 'Glucansucrases: three-dimensional structures, reactions, mechanism, [alpha]-glucan analysis and their implications in biotechnology and food applications,' Journal of Biotechnology, Jan. 1, 2013, vol. 163, No. 2, pp. 250-272.

Mao et al., 'A novel dextran dextrinase from DSM-2003: purification and properties,' Applied Biochemistry and Biotechnology, Sep. 9, 2012, vol. 168, No. 5, pp. 1256-1264.

Monchois et al., 'Glucansucrases: mechanism of action and structure-function relationships,' FEMS Microbiol Rev., 1999, vol. 23, pp. 131-151.

Monchois et al., 'Cloning and sequencing of a gene coding for an extracellular dextransucrase (DSRB) from Leuconostoc mesenteroides NRRL B-1299 synthesizing only a alpha(1-6) glucan,' Fems Microbiology Letters, Feb. 15, 1998, vol. 159, No. 2, pp. 307-315.

Mountzouris et al., 'A study of dextran production from maltodextrin by cell suspensions of Gluconobacter oxydans NCIB 4943,' Journal of Applied Microbiology, Oct. 1999, vol. 87, No. 4, pp. 546-556.

Naessens et al., 'Dextran dextrinase and dextran of Gluconobacter oxydans,' Journal of Industrial Microbiology & Biotechnology, Aug. 1, 2005, vol. 32, No. 8, pp. 323-334.

Naessens et al., 'Leuconostoc dextransucrase and dextran: production, properties and applications,' Journal of Chemical Technology & Biotechnology, Aug. 1, 2005, vol. 80, No. 8, pp. 845-860.

Sarbini et al., 'In vitro fermentation of linear and α-1,2-branched dextrans by the human fecal microbiota,' Applied and Environmental Microbiology, 2011, vol. 77(15), pp. 5307-5315.

(56) References Cited

OTHER PUBLICATIONS

Sarwat et al., 'Production & characterization of a unique dextran from an indigenous Leuconostoc mesenteroides CMG713,' International Journal of Biological Sciences, Oct. 5, 2008, vol. 4, No. 6, pp. 379-386.

Shimamura et al., 'Identification of Amino Acids Residues in *Streptococcus mutans* Glucosyltransferases Influencing the Structure of the Glucan Product,' J. Bacteriology, 1994, vol. 176, pp. 4845-4850.

Shimotsuura et al., 'Biochemical and molecular characterization of a novel type of mutunase from *Paenibacillus* sp. Strain RM1: Identification of its mutan-binding domain, essential for degradation of *Streptococcus mutans* biofilms,' Applied and Environmental Microbiology, 2008, vol. 74, pp. 2759-2765.

Simpson et al., 'Four glucosyltransferases, GtfJ, GtfK, GtfL, and GtfM from *Streptococcus salivarius* ATCC 25975,' Microbiology, Jun. 1, 1995, vol. 141, No. 6, pp. 1451-1460.

Sims et al., 'Characterization of polysaccharides synthesised by Gluconobacter oxydans NCIMB 4943,' Carbohydrate Polymers, Applied Science Publishers, Ltd., Jul. 1, 2001, vol. 45, No. 3, pp. 285-292.

Suyotha et al., 'Domain structure and function of a α-1,3-glucanase from Bacillus circulans KA-304, and enzyme essential for degrading basidiomycete cell walls,' Biosci. Biotechnol. Biochem., 2013, vol. 77, pp. 639-647.

Suzuki et al., 'Structural elucidation of dextran degradation mechanism by *Streptoccus mutans* dextranase belonging to glycoside hydrolase family 66,' J. Biol. Chem., 2012, vol. 287, pp. 19916-19926.

Tsumori et al., 'Purification and properties of extracellular glucosyltransferase synthesizing 1,6-1,3-X-D-glucan from *Streptococcus mutans* serotype A,' Journal of General Microbiology, Jan. 1, 1985, vol. 131, pp. 3347-3353.

Vettori et al., 'Structural characterization of a new dextran with a low degree of branching produced by Leuconostoc mesenteroides FT045B dextransucrase,' Carbohydrate Polymers, May 1, 2012, vol. 88, No. 4, pp. 1440-1444.

Wang et al., 'Characterization of a novel dextran produced by Gluconobacter oxydans DSM 2003,' Applied Microbiology and Biotechnology, Apr. 16, 2011, vol. 91, No. 2, pp. 287-294.

Yamamoto et al., 'Structure of dextran synthesized by dextrin dextranase from acetobacter capsulatus ATCC 11894,' Bioscience, Biotechnology and Biochemistry, Jan. 12, 1993, vol. 57, No. 9, pp. 1450-1453.

Yamamoto et al., 'Effective dextran production from starch by dextrin dextranase with debranching enzyme,' Journal of Fermentation and Bioengineering, Society of Fermentation Technology, Jan. 1, 1993, vol. 76, No. 5, pp. 411-413.

US Department of Agriculture and US Department of Health and Human Services, Dietary Guidelines for Americans, 2010, 7th Edition, Washington, DC, US Government Printing Office, Dec. 2010.

International Search Report issued for PCT/US2015/032139 dated Aug. 12, 2015.

Written Opinion issued for PCT/US2015/032139 dated Aug. 12, 2015.

\* cited by examiner

```
                        SEQUENCE LISTING

<160> NUMBER OF SEQ ID NOS: 13

<210> SEQ ID NO 1
<211> LENGTH: 1651
<212> TYPE: PRT
<213> ORGANISM: Lactobacillus animalis

<400> SEQUENCE: 1

Met Phe Glu Lys Lys Leu His Tyr Lys Met Tyr Lys Ala Gly Lys His
1               5                   10                  15

Trp Val Phe Ala Ala Ile Ala Val Gly Ile Phe Gly Phe Ala Ser Thr
            20                  25                  30

Thr Ser Ala Leu Ala Asp Glu Thr Ser Ser Asn Glu Thr Gln Thr
        35                  40                  45

Glu Gln Thr Leu Asn Thr Asp Glu Ser Thr Asp Thr Thr Asp Val
    50                  55                  60

Ser Asn Glu Ala Lys Ala Thr Glu Ala Gln Leu Thr Thr Gln Asp Ala
65                  70                  75                  80

Asp Met Ala Ser Ser Glu Glu Lys Thr Thr Asn Val Glu Lys Glu Val
                85                  90                  95

Thr Thr Ala Glu Thr Asn Lys Asp Thr Thr Val Lys Asn Val Glu Ser
            100                 105                 110

Ser Glu Gln Asn Thr Thr Thr Val Ala Asp Lys Asn Ala Val Asp Ser
        115                 120                 125

Thr Ala Gln Val Asn Thr Ala Glu Lys Glu Asn Lys Tyr Thr Gln Glu
    130                 135                 140
```

-continued

```
Asn Val Asn Gly Asn Trp Tyr Leu Lys Asp Glu Gln Gly Asn Tyr Leu
145                 150                 155                 160

Thr Gly Phe Gln Glu Ile Lys Asp Gln Asn Lys Thr Val Tyr Tyr Asn
            165                 170                 175

Pro Asp Ser Lys Gln Met Val Tyr Gly Gln Gln Asn Ile Asn Gly Asn
            180                 185                 190

Trp Tyr Leu Phe Asp Thr Phe Asn Gly Ala Met Gln Thr Gly Leu Gln
            195                 200                 205

Tyr Ile Arg Asp Gln Lys Lys Leu Ala Tyr Tyr Asn Glu Gln Gly Gln
            210                 215                 220

Met Gln Tyr Gly Thr Val Glu Ile Asp Gly Lys Tyr Gln Ala Asp
225                 230                 235                 240

Thr Phe Asn Gly Ala Ile Lys Gly Lys Gly Gln Thr Lys Ile Ala Asp
            245                 250                 255

Asn Trp Tyr Leu Phe Asn Asn Ala Gly Gln Val Val Asp Gly Trp Gln
            260                 265                 270

Trp Ile Asn Asp Gln Gly Lys Thr Val Tyr Tyr Ser Thr Lys Thr Ala
            275                 280                 285

Gln Met Val His Gly Gln Asn Ile Asn Gly His Trp Tyr Leu Phe
290                 295                 300

Asp Lys Thr Thr Gly Ala Met Gln Arg Gly Phe Gln Asn Leu Lys Ala
305                 310                 315                 320

Tyr Gly Asp Asp Lys Thr Val Tyr Tyr Asn Gln Asp Gly Trp Met Leu
            325                 330                 335

Tyr Gly Gln Gln Lys Ile Asp Asn Lys Trp Tyr Asn Phe Asp Thr Phe
            340                 345                 350

Asn Gly Ala Met Lys Thr Gly Phe Val Lys Ile Pro Glu Gln Asn Lys
            355                 360                 365

Thr Val Tyr Tyr Ala Pro Asn Gly Gln Met Gly Tyr Gly Trp Gln Trp
370                 375                 380

Val Asp Asn Ala Thr Arg Tyr Phe Asp Thr Phe Asn Gly Ala Met Ala
385                 390                 395                 400

Thr Gly Gln Lys Leu Ile Thr Gly His Trp Tyr Leu Phe Asp Asn Asn
            405                 410                 415

Gly Ala Met Gln Arg Gly Phe Gln Asn Leu Lys Asn Tyr Gly Asp Asn
            420                 425                 430

Lys Thr Val Tyr Tyr Asn Gln Asp Gly Trp Met Leu Tyr Gly Trp Gln
            435                 440                 445

Trp Val Asn Asn Ala Thr Arg Tyr Phe Asp Thr Phe Asn Gly Ala Met
450                 455                 460

Thr Thr Gly Gln Lys Lys Ile Asn Asp His Trp Tyr Leu Phe Asp Lys
465                 470                 475                 480

Asp Gly Ala Met Gln Arg Gly Ile Gln Tyr Ile Pro Glu Glu Asn Lys
            485                 490                 495

Leu Val Tyr Tyr Asn Gln Asp Gly Trp Met Leu Tyr Gly Lys Gln Asn
            500                 505                 510

Ile Asn Gly Val Asp His Asn Phe Asn Thr Phe Asn Gly Ala Leu Glu
            515                 520                 525

Ala Lys Gly Gln Val Lys Val Gly Asn Asn Trp Tyr Leu Phe Asn Asn
            530                 535                 540

Ser Gly Thr Ile Gln Thr Gly Phe Gln Asp Leu Lys Ala Tyr Gly Gln
545                 550                 555                 560
```

```
Asp Lys Val Val Tyr Asp Pro Lys Thr Ala Ala Met Val Tyr Gly
            565                 570                 575

Tyr Gln Asn Ile Asp Gly Asn Trp Tyr Leu Phe Ser Arg Ala Asn Gly
            580                 585                 590

Ser Met Gln Arg Gly Leu Gln Asn Val Asn Gly Val Asp Leu Leu Phe
            595                 600                 605

Asp Glu Lys Thr Gly Ala Leu Leu Thr Gly Val Gln Asn Ile Lys Gly
            610                 615                 620

Asn Asn Tyr Phe Val Asp Lys Arg Ser Gly Asn Ile Lys Lys Asn Leu
625                 630                 635                 640

Val Val Leu Gly Ala Asp Asn Lys Trp Met Tyr Phe Asp Ala Lys Thr
            645                 650                 655

Gly Lys Gly Thr Asn Thr Leu Glu Asp Gln Tyr Lys Lys Gly Val Val
            660                 665                 670

Ser Gly Asn Val Glu Phe Ile Thr Asn Asn Ala Ala Tyr Ser Phe Asp
            675                 680                 685

Gly Asn Ser Phe Glu Asn Ile Asn Gly Phe Leu Thr Ala Asp Ser Trp
            690                 695                 700

Tyr Arg Pro Lys Ser Ile Leu Lys Asp Gly Ser Thr Trp Thr Ala Thr
705                 710                 715                 720

Thr Glu Thr Asp Leu Arg Pro Leu Leu Met Thr Trp Trp Pro Asn Glu
            725                 730                 735

Gln Ile Lys Ala Asn Tyr Leu Asn Tyr Met Lys Asp Lys Gly Phe Ile
            740                 745                 750

Asn Asn Ser Gly Thr Tyr Asn Ala Glu Ser Asp Pro Asn Tyr Met Asp
            755                 760                 765

Phe Ala Ala Gln Glu Ala Gln Arg Asn Ile Glu Arg Lys Ile Thr Lys
            770                 775                 780

Glu Asn Asp Thr Thr Trp Leu Arg Asp Leu Ile Thr Asp Phe Ile Lys
785                 790                 795                 800

Thr Gln Asp Ile Trp Asn Glu Gln Ser Glu Gly Val Ser Thr Glu Gly
            805                 810                 815

Leu Gln Lys Phe Gln Gly Gly Phe Leu Lys Tyr Val Asn Ser Glu Leu
            820                 825                 830

Thr Pro Tyr Ala Asn Ser Glu Trp Arg Lys Leu Gly Tyr Gln Pro Thr
            835                 840                 845

Met Leu Thr Gln Asn Asn Val Gly Ala Glu Phe Leu Leu Ala Asn Asp
            850                 855                 860

Ile Asp Asn Ser Asn Pro Val Val Gln Ala Glu Gln Leu Asn Trp Leu
865                 870                 875                 880

His Phe Leu Met Asn Phe Gly Thr Ile Thr Ala Asn Asp Pro Ser Ala
            885                 890                 895

Asn Phe Asp Gly Ile Arg Ile Asp Ala Val Asp Asn Val Asp Ala Ser
            900                 905                 910

Leu Leu Ser Ile Ala Gly Asp Tyr Phe Lys Ala Ala Tyr Lys Val Gly
            915                 920                 925

Gln Asn Asp Ala Thr Ala Asn Lys His Ile Ser Ile Leu Glu Asp Trp
            930                 935                 940

Asn Asp Lys Asp Pro Glu Tyr Val Asn Ser Ile Gly Asn Pro Gln Leu
945                 950                 955                 960

Thr Met Asp Asp Tyr Ile Val Gln Gln Leu Lys Phe Ser Leu Gly Gln
            965                 970                 975

Ala Pro Asp Lys Val Asp Arg Met Gln Arg Phe Lys Glu Trp Tyr Leu
```

```
              980               985               990
Val Asp Arg Ser Lys Asp Asn Thr Glu Asn Thr Ala Ile Pro Asn Tyr
                995               1000              1005

Ser Phe Val Arg Ala His Asp Ala Ser Val Gln Glu Asp Ile Leu
1010                1015              1020

Gln Leu Ile Gln Asp Thr Thr Gly Lys Pro Trp Gly Val Tyr Thr
1025                1030              1035

Asn Glu Glu Leu Gln Gln Gly Leu Lys Asp Tyr Met Ala Asp Gln
1040                1045              1050

Lys Leu Thr Asn Lys Lys Tyr Asn Arg Tyr Asn Ile Pro Ser Ser
1055                1060              1065

Tyr Ala Ile Leu Leu Thr Asn Lys Asp Thr Ile Pro Arg Val Tyr
1070                1075              1080

Tyr Gly Asp Leu Tyr Ser Asp Ala Gly Lys Tyr Met Ala Glu Lys
1085                1090              1095

Ser Ile Tyr Phe Asp Ala Ile Asp Asn Leu Leu Lys Thr Arg Thr
1100                1105              1110

Lys Tyr Val Ala Gly Gly Gln Thr Leu Asp Val Asp Gly His Asp
1115                1120              1125

Ile Leu Thr Ser Val Arg Phe Gly Lys Gly Ala Leu Asn Val Thr
1130                1135              1140

Asp Lys Gly Thr Ser Glu Thr Arg Thr Gln Gly Met Gly Leu Ile
1145                1150              1155

Ile Ser Asn Asn Asn Ser Leu Lys Leu Asn Asp Gly Glu Lys Val
1160                1165              1170

Val Leu His Met Gly Ala Ala His Lys Asn Gln Ala Tyr Arg Ala
1175                1180              1185

Val Met Leu Ser Ser Ala Asn Gly Leu Ile Asn Tyr Thr Ser Asp
1190                1195              1200

Ala Asn Ala Pro Val Val Tyr Thr Asn Asn Asp Gly Asp Leu Ile
1205                1210              1215

Phe Thr Asn Lys Asp Val Val Thr Asn Gly Lys Val Gln Ala Asn
1220                1225              1230

Thr Ala Ile Lys Gly Val Met Asn Pro Tyr Val Ser Gly Tyr Leu
1235                1240              1245

Ala Met Trp Val Pro Val Gly Ala Ser Ala Thr Gln Asp Ala Arg
1250                1255              1260

Thr Ala Ala Ser Thr Lys Thr Thr Asp Gly Ser Val Phe His
1265                1270              1275

Ser Asn Ala Ala Leu Asp Ser Asn Leu Ile Tyr Glu Gly Phe Ser
1280                1285              1290

Asn Phe Gln Ala Phe Pro Glu Asn Ala Ser Glu Asn Ala Asn Ala
1295                1300              1305

Ile Ile Ala Gln Asn Val Asp Leu Phe Asn Ser Trp Gly Val Thr
1310                1315              1320

Ser Phe Gln Leu Ala Pro Gln Tyr Val Ser Ser His Asp Gly Ser
1325                1330              1335

Phe Leu Asp Ser Ile Ile Asp Asn Gly Tyr Ala Phe Thr Asp Arg
1340                1345              1350

Tyr Asp Leu Ala Met Ser Lys Asn Asn Lys Tyr Gly Ser Tyr Gln
1355                1360              1365

Asp Leu Val Asn Val Leu Lys Ala Leu His Ala Gly Gly Ile Gln
1370                1375              1380
```

Val Ile Ala Asp Trp Val Pro Asp Gln Ile Tyr Ser Leu Pro Gly
    1385            1390            1395

Lys Glu Val Val Ser Val Val Arg Ser Asp Glu Phe Gly Asn Lys
    1400            1405            1410

Val Asp Gly Thr Gln Ile Asp Asn Thr Leu Tyr Val Val Asn Thr
    1415            1420            1425

Ile Gly Gly Gly Gln Tyr Gln Lys Glu Tyr Gly Gly Arg Tyr Leu
    1430            1435            1440

Glu Glu Leu Lys Gln Lys Tyr Pro Glu Leu Phe Lys Thr Lys Gln
    1445            1450            1455

Pro Ser Thr Gly Val Thr Ile Asp Pro Ser Glu Lys Ile Thr Glu
    1460            1465            1470

Trp Ser Ala Lys Tyr Leu Asn Gly Thr Asn Ile Leu His Arg Gly
    1475            1480            1485

Ala Glu Phe Val Leu Arg Asp Gly Ala Thr Tyr Phe Arg Val Ala
    1490            1495            1500

Glu Thr Ser Glu Val Phe Leu Pro Ser Gln Leu Arg Gly Lys Ile
    1505            1510            1515

Thr Lys Asn Gly Phe Trp Lys Asn Asp Ala Gly Lys Val Asn Tyr
    1520            1525            1530

Tyr Asn Ser Glu Gly Glu Ile Met Lys Asn Ala Phe Val Lys Asp
    1535            1540            1545

Gly Lys Asn Asn Trp Tyr Tyr Phe Asp Asn Asp Gly Asn Met Val
    1550            1555            1560

Thr Asn Thr Ala Leu Thr Ile Asp Ser Asp Ala Gln Val Ala Asp
    1565            1570            1575

Tyr Tyr Phe Leu Asn Asn Gly Ile Ser Leu Arg Asp Gly Phe Val
    1580            1585            1590

Gln Leu Ala Asn Gly Asp Ile Tyr Tyr Tyr Asp Val Asn Gly Arg
    1595            1600            1605

Lys Leu Lys Asn Gly Lys Val Thr Val Asn Asn Val Glu Tyr Thr
    1610            1615            1620

Thr Asp Lys Asn Gly Lys Val Val Gly Glu Asn Val Leu Lys Lys
    1625            1630            1635

Leu Asp Glu Ile Ile Thr Thr Gly Lys Thr Thr Leu Ile
    1640            1645            1650

<210> SEQ ID NO 2
<211> LENGTH: 4941
<212> TYPE: DNA
<213> ORGANISM: Lactobacillus animalis

<400> SEQUENCE: 2
gtgagaagca aaaaattgtg gatcagcttg ttgtttgcgt taacgttaat ctttacgatg      60
gcgttcagca acatgagcgc gcaggctgct ggaaaagacg agacaagcag ctcaaacgaa     120
acacaaacgg aacaaacgct taacacggat gagtcaacag acacaacgac ggacgtctca     180
aatgaggcca agcaacggaa ggcacaactg acaacgcaag atgcagacat ggcgagctca     240
gaagaaaaaa caacgaatgt cgagaaagag gttacaacgg ctgaaacaaa taagacacg      300 acggtcaaaa atgtggagtc aagcgaacag aatacaacga cagtggcaga caagaatgcc     360
gtggattcaa cagctcaagt taacacagcg gagaaggaga caagtacac gcaggagaat      420 gtgaacggca attggtatct gaaagatgag cagggcaact atcttacggg attccaagag     480

```
attaaagacc aaaacaaaac agtgtattat aaccctgata gcaagcagat ggtctacgga    540
cagcaaaaca tcaacggaaa ctggtacctt ttcgatacat tcaatggagc gatgcaaaca    600
ggacttcaat atatcagaga tcaaaaaaag cttgcttatt acaatgaaca gggacaaatg    660
caatatggca cagtcgagat cgatggacaa aagtaccaag cggatacgtt taatggcgcg    720
atcaaaggca aaggccagac aaaaatcgct gacaattggt atcttttcaa taatgccgga    780
caggtcgtgg atggctggca gtggattaac gaccagggaa agacagttta ttactcaaca    840
aaaacggccc aaatggtcca tggccagcag aatattaatg gacattggta cctgttcgat    900
aagacaacag cgctatgca aagaggcttc caaaacctta agcctacgg agacgacaag      960
acggtgtact ataatcaaga cggctggatg ctgtatggcc aacagaagat tgataacaag   1020
tggtacaatt tcgacacgtt caatggagct atgaagacag gattcgtgaa aattccggag   1080
cagaacaaga cagtctacta cgcaccgaac ggccaaatgc agtatggctg cagtgggtc    1140
gataacgcga cgagatattt cgacacgttt aatggcgcaa tggcaacggg acagaagctg   1200
attacaggac actggtatct gtttgacaac aatggcgcaa tgcagagagg cttccagaat   1260
ctgaagaatt atggagacaa taaaacggtt tactacaacc aagatggatg gatgctttat   1320
ggctggcaat gggtcaacaa cgctacaaga tactttgaca catttaacgg agccatgacg   1380
acgggccaga aaaagattaa tgaccattgg tacctttttg ataaggacgg cgccatgcag   1440
agaggaatcc aatacatccc tgaggaaaat aagcttgtgt actacaatca ggacggatgg   1500
atgctgtacg gcaagcaaaa tatcaatggc gtcgatcata actttaatac gttcaatgga   1560
gcacttgagg ctaagggcca agtgaaagtg gcaataattg gtatctgtt caacaatagc    1620
ggaacgattc agacaggctt tcaggacctg aaggcttacg ccaggataa agtcgtttac    1680
tatgatccta agacggcagc catggtttat ggatatcaga acatcgacgg caactggtac   1740
cttttcagca gagcaaatgg cagcatgcaa agaggcctc aaaacgtcaa cggcgttgac   1800
ctgcttttcg atgaaaagac gggcgcactg ctgacaggag ttcaaaatat caagggaaat   1860
aactactttg tggataagag aagcggaaac atcaagaaga accttgtggt ccttggagcc   1920
gataataagt ggatgtactt cgatgcgaaa acggaaaag gcacgaacac gcttgaggat   1980
cagtacaaaa aaggagttgt tagcggcaac gtggaattta ttacgaataa cgcagcgtat   2040
agctttgatg gcaatagctt cgaaaacatt aacggcttcc tgacggccga ttcatggtac   2100
agaccgaaat caattcttaa agatggctca acatggacag caacaacaga gacagacctt   2160
agaccgctgc tgatgacatg gtggccgaac gaacaaatca aggccaacta cctgaactac   2220
atgaaggaca agggattcat caataactca ggcacgtata atgctgagtc agacccgaac   2280
tatatggact tcgctgccca ggaggcgcag agaaatattg agagaaaaat cacgaaggaa   2340
aacgatacga cgtggcttag agatcttatc acagacttca ttaaaacaca ggatatctgg   2400
aacgagcaat cagagggagt tagcacggag ggcctgcaaa aatttcaggg cggctttctt   2460
aagtatgtga atagcgagct gacgccttac gcaaactcag aatggagaaa actgggctac   2520
caaccgacga tgcttacaca aaataacgtt ggcgcggagt tccttcttgc caatgatatc   2580
gacaactcaa atccggtcgt gcaagctgaa caacttaact ggctgcactt tctgatgaac   2640
tttggcacga tcacagctaa cgatccgagc gcgaacttcg acggaatcag aatcgatgca   2700
gtcgataatg tggacgcatc actgctgtca atcgctggcg attatttcaa ggcagcgtac   2760
aaggtgggcc aaaacgatgc cacagccaac aagcacatct caatcctgga agactggaac   2820
gataaggacc ctgagtacgt taatagcatc ggaaacccgc aactgacaat ggatgactac   2880
```

```
atcgtgcaac aactgaaatt ttcactggga caggcacctg ataaggtcga cagaatgcaa    2940
agatttaagg agtggtacct ggttgacaga tcaaaggata atacggaaaa cacagcgatc    3000
ccgaactata gcttcgtgag agcacatgac gcctcagttc aagaggacat cctgcagctg    3060
atccaggaca cgacaggaaa accgtggggc gtctatacga acgaagagct gcaacaaggc    3120
ctgaaggact atatggcgga ccagaagctt acgaacaaga aatacaatag atacaacatc    3180
ccgagcagct atgctatcct gctgacaaac aaagacacaa tccctagagt gtattatggc    3240
gacctgtata gcgacgccgg aaagtacatg gccgagaagt caatttactt tgatgccatt    3300
gacaacctgc ttaaaacgag aacgaaatat gtggcaggcg gccaaacact ggacgttgac    3360
ggacatgata tcctgacaag cgtcagattc ggaaagggag ccctgaatgt cacagataaa    3420
ggcacgagcg agacaagaac gcaaggcatg ggactgatca tcagcaataa caactcactg    3480
aagctgaacg acggagaaaa ggttgtgctt catatgggcg ccgcacacaa gaatcaagcc    3540
tatagagcag tcatgcttag cagcgcaaat ggcctgatta actatacatc agacgcgaac    3600
gcacctgtgg tttatacaaa taacgatggc gatctgatct ttacgaataa agatgtcgtc    3660
acaaatggaa aggtgcaggc caatacagca attaagggcg ttatgaaccc ttacgtcagc    3720
ggctatcttg caatgtgggt gccggttggc gcatcagcga cacaggatgc aagaacagcc    3780
gctagcacga agacaacgac agatggctca gttttccaca gcaacgctgc acttgatagc    3840
aacctgattt atgaaggatt ctcaaacttc caagcttttc cggagaatgc ctcagaaaat    3900
gccaatgcga tcatcgccca aaatgtcgat ctgttcaact catggggagt cacgtcattt    3960
caactggctc ctcaatatgt ctcaagccac gacggcagct tcctggacag catcatcgac    4020
aacggctatg cattcacgga cagatacgac cttgcgatga gcaaaaacaa caaatatggc    4080
tcataccagg atctggttaa tgtcctgaag gcactgcatg cgggaggaat ccaagttatc    4140
gcagattggg ttccggacca aatctattca ctgccgggca aagaggtcgt tagcgttgtt    4200
agaagcgacg agttcggcaa caaagtggat ggcacgcaaa tcgataacac gctgtacgtg    4260
gtcaatacga tcggcggagg ccagtatcaa aaggaatacg gcggaagata ccttgaagaa    4320
cttaaacaaa agtatccgga gcttttaag acgaaacagc cttcaacagg cgttacaatc    4380
gatccgtcag agaagattac ggagtggagc gccaagtatc tgaacggcac aaacattctt    4440
catagaggcg cagaatttgt cctgagagat ggcgctacat actttagagt cgcagaaaca    4500
agcgaagtgt tccttcctag ccagcttaga ggcaaaatca caaaaaacgg attttggaaa    4560 aacgacgcg gaaaagtcaa ctactataac tcagagggaa aaatcatgaa aaatgctttc    4620
gtcaaagacg gaaagaataa ctggtactac ttcgacaatg acggcaatat ggtcacgaac    4680
acggcactga cgattgattc agatgcccag gtggctgatt actatttcct gaataacggc    4740
attagcctta gagacggctt tgtgcaactt gcaaacggag acatctacta ctacgatgtg    4800
aatggcagaa aacttaagaa cggcaaagtt acagtcaata acgttgaata cacaacggac    4860
aaaaatggca aggtggtcgg agagaacgtg ctgaaaaaac tggatgagat tattacaacg    4920
ggaaagacga cacttatttg a                                              4941
```

<210> SEQ ID NO 3
<211> LENGTH: 1614
<212> TYPE: PRT
<213> ORGANISM: Lactobacillus animalis

<400> SEQUENCE: 3

```
Asp Glu Thr Ser Ser Asn Glu Thr Gln Thr Gln Thr Leu Asn
  1               5                  10                  15

Thr Asp Glu Ser Thr Asp Thr Thr Asp Val Ser Asn Glu Ala Lys
             20                  25                  30

Ala Thr Glu Ala Gln Leu Thr Thr Gln Asp Ala Asp Met Ala Ser Ser
         35                  40                  45

Glu Glu Lys Thr Thr Asn Val Glu Lys Glu Val Thr Thr Ala Glu Thr
     50                  55                  60

Asn Lys Asp Thr Thr Val Lys Asn Val Glu Ser Glu Gln Asn Thr
 65              70                  75                  80

Thr Thr Val Ala Asp Lys Asn Ala Val Asp Ser Thr Ala Gln Val Asn
                 85                  90                  95

Thr Ala Glu Lys Glu Asn Lys Tyr Thr Gln Glu Asn Val Asn Gly Asn
             100                 105                 110

Trp Tyr Leu Lys Asp Glu Gln Gly Asn Tyr Leu Thr Gly Phe Gln Glu
             115                 120                 125

Ile Lys Asp Gln Asn Lys Thr Val Tyr Tyr Asn Pro Asp Ser Lys Gln
         130                 135                 140

Met Val Tyr Gly Gln Gln Asn Ile Asn Gly Asn Trp Tyr Leu Phe Asp
145                 150                 155                 160

Thr Phe Asn Gly Ala Met Gln Thr Gly Leu Gln Tyr Ile Arg Asp Gln
             165                 170                 175

Lys Lys Leu Ala Tyr Tyr Asn Glu Gln Gly Gln Met Gln Tyr Gly Thr
         180                 185                 190

Val Glu Ile Asp Gly Gln Lys Tyr Gln Ala Asp Thr Phe Asn Gly Ala
         195                 200                 205

Ile Lys Gly Lys Gly Gln Thr Lys Ile Ala Asp Asn Trp Tyr Leu Phe
    210                 215                 220

Asn Asn Ala Gly Gln Val Val Asp Gly Trp Gln Trp Ile Asn Asp Gln
225                 230                 235                 240

Gly Lys Thr Val Tyr Tyr Ser Thr Lys Thr Ala Gln Met Val His Gly
                 245                 250                 255

Gln Gln Asn Ile Asn Gly His Trp Tyr Leu Phe Asp Lys Thr Thr Gly
             260                 265                 270

Ala Met Gln Arg Gly Phe Gln Asn Leu Lys Ala Tyr Gly Asp Asp Lys
         275                 280                 285

Thr Val Tyr Tyr Asn Gln Asp Gly Trp Met Leu Tyr Gly Gln Gln Lys
     290                 295                 300

Ile Asp Asn Lys Trp Tyr Asn Phe Asp Thr Phe Asn Gly Ala Met Lys
305                 310                 315                 320

Thr Gly Phe Val Lys Ile Pro Glu Gln Asn Lys Thr Val Tyr Tyr Ala
                 325                 330                 335

Pro Asn Gly Gln Met Gln Tyr Gly Trp Gln Trp Val Asp Asn Ala Thr
             340                 345                 350

Arg Tyr Phe Asp Thr Phe Asn Gly Ala Met Ala Thr Gly Gln Lys Leu
         355                 360                 365

Ile Thr Gly His Trp Tyr Leu Phe Asp Asn Gly Ala Met Gln Arg
         370                 375                 380

Gly Phe Gln Asn Leu Lys Asn Tyr Gly Asp Asn Lys Thr Val Tyr Tyr
385                 390                 395                 400

Asn Gln Asp Gly Trp Met Leu Tyr Gly Trp Gln Trp Val Asn Asn Ala
                 405                 410                 415

Thr Arg Tyr Phe Asp Thr Phe Asn Gly Ala Met Thr Thr Gly Gln Lys
```

-continued

```
                420                 425                 430
Lys Ile Asn Asp His Trp Tyr Leu Phe Asp Lys Asp Gly Ala Met Gln
            435                 440                 445
Arg Gly Ile Gln Tyr Ile Pro Glu Glu Asn Lys Leu Val Tyr Tyr Asn
        450                 455                 460
Gln Asp Gly Trp Met Leu Tyr Gly Lys Gln Asn Ile Asn Gly Val Asp
465                 470                 475                 480
His Asn Phe Asn Thr Phe Asn Gly Ala Leu Glu Ala Lys Gly Gln Val
                485                 490                 495
Lys Val Gly Asn Asn Trp Tyr Leu Phe Asn Asn Ser Gly Thr Ile Gln
            500                 505                 510
Thr Gly Phe Gln Asp Leu Lys Ala Tyr Gly Gln Asp Lys Val Val Tyr
        515                 520                 525
Tyr Asp Pro Lys Thr Ala Ala Met Val Tyr Gly Tyr Gln Asn Ile Asp
    530                 535                 540
Gly Asn Trp Tyr Leu Phe Ser Arg Ala Asn Gly Ser Met Gln Arg Gly
545                 550                 555                 560
Leu Gln Asn Val Asn Gly Val Asp Leu Leu Phe Asp Glu Lys Thr Gly
                565                 570                 575
Ala Leu Leu Thr Gly Val Gln Asn Ile Lys Gly Asn Asn Tyr Phe Val
            580                 585                 590
Asp Lys Arg Ser Gly Asn Ile Lys Lys Asn Leu Val Val Leu Gly Ala
        595                 600                 605
Asp Asn Lys Trp Met Tyr Phe Asp Ala Lys Thr Gly Lys Gly Thr Asn
    610                 615                 620
Thr Leu Glu Asp Gln Tyr Lys Lys Gly Val Val Ser Gly Asn Val Glu
625                 630                 635                 640
Phe Ile Thr Asn Asn Ala Ala Tyr Ser Phe Asp Gly Asn Ser Phe Glu
                645                 650                 655
Asn Ile Asn Gly Phe Leu Thr Ala Asp Ser Trp Tyr Arg Pro Lys Ser
            660                 665                 670
Ile Leu Lys Asp Gly Ser Thr Trp Thr Ala Thr Thr Glu Thr Asp Leu
        675                 680                 685
Arg Pro Leu Leu Met Thr Trp Trp Pro Asn Glu Gln Ile Lys Ala Asn
    690                 695                 700
Tyr Leu Asn Tyr Met Lys Asp Lys Gly Phe Ile Asn Asn Ser Gly Thr
705                 710                 715                 720
Tyr Asn Ala Glu Ser Asp Pro Asn Tyr Met Asp Phe Ala Ala Gln Glu
                725                 730                 735
Ala Gln Arg Asn Ile Glu Arg Lys Ile Thr Lys Glu Asn Asp Thr Thr
            740                 745                 750
Trp Leu Arg Asp Leu Ile Thr Asp Phe Ile Lys Thr Gln Asp Ile Trp
        755                 760                 765
Asn Glu Gln Ser Glu Gly Val Ser Thr Glu Gly Leu Gln Lys Phe Gln
    770                 775                 780
Gly Gly Phe Leu Lys Tyr Val Asn Ser Glu Leu Thr Pro Tyr Ala Asn
785                 790                 795                 800
Ser Glu Trp Arg Lys Leu Gly Tyr Gln Pro Thr Met Leu Thr Gln Asn
                805                 810                 815
Asn Val Gly Ala Glu Phe Leu Leu Ala Asn Asp Ile Asp Asn Ser Asn
            820                 825                 830
Pro Val Val Gln Ala Glu Gln Leu Asn Trp Leu His Phe Leu Met Asn
        835                 840                 845
```

```
Phe Gly Thr Ile Thr Ala Asn Asp Pro Ser Ala Asn Phe Asp Gly Ile
    850                 855                 860

Arg Ile Asp Ala Val Asp Asn Val Asp Ala Ser Leu Leu Ser Ile Ala
865                 870                 875                 880

Gly Asp Tyr Phe Lys Ala Ala Tyr Lys Val Gly Gln Asn Asp Ala Thr
                885                 890                 895

Ala Asn Lys His Ile Ser Ile Leu Glu Asp Trp Asn Asp Lys Asp Pro
            900                 905                 910

Glu Tyr Val Asn Ser Ile Gly Asn Pro Gln Leu Thr Met Asp Asp Tyr
        915                 920                 925

Ile Val Gln Gln Leu Lys Phe Ser Leu Gly Gln Ala Pro Asp Lys Val
    930                 935                 940

Asp Arg Met Gln Arg Phe Lys Glu Trp Tyr Leu Val Asp Arg Ser Lys
945                 950                 955                 960

Asp Asn Thr Glu Asn Thr Ala Ile Pro Asn Tyr Ser Phe Val Arg Ala
                965                 970                 975

His Asp Ala Ser Val Gln Glu Asp Ile Leu Gln Leu Ile Gln Asp Thr
            980                 985                 990

Thr Gly Lys Pro Trp Gly Val Tyr  Thr Asn Glu Glu Leu  Gln Gln Gly
         995                 1000                 1005

Leu Lys  Asp Tyr Met Ala Asp  Gln Lys Leu Thr Asn  Lys Lys Tyr
        1010                 1015                 1020

Asn Arg  Tyr Asn Ile Pro Ser  Ser Tyr Ala Ile Leu  Leu Thr Asn
        1025                 1030                 1035

Lys Asp  Thr Ile Pro Arg Val  Tyr Tyr Gly Asp Leu  Tyr Ser Asp
        1040                 1045                 1050

Ala Gly  Lys Tyr Met Ala Glu  Lys Ser Ile Tyr Phe  Asp Ala Ile
        1055                 1060                 1065

Asp Asn  Leu Leu Lys Thr Arg  Thr Lys Tyr Val Ala  Gly Gly Gln
        1070                 1075                 1080

Thr Leu  Asp Val Asp Gly His  Asp Ile Leu Thr Ser  Val Arg Phe
        1085                 1090                 1095

Gly Lys  Gly Ala Leu Asn Val  Thr Asp Lys Gly Thr  Ser Glu Thr
        1100                 1105                 1110

Arg Thr  Gln Gly Met Gly Leu  Ile Ile Ser Asn Asn  Asn Ser Leu
        1115                 1120                 1125

Lys Leu  Asn Asp Gly Glu Lys  Val Val Leu His Met  Gly Ala Ala
        1130                 1135                 1140

His Lys  Asn Gln Ala Tyr Arg  Ala Val Met Leu Ser  Ser Ala Asn
        1145                 1150                 1155

Gly Leu  Ile Asn Tyr Thr Ser  Asp Ala Asn Ala Pro  Val Val Tyr
        1160                 1165                 1170

Thr Asn  Asn Asp Gly Asp Leu  Ile Phe Thr Asn Lys  Asp Val Val
        1175                 1180                 1185

Thr Asn  Gly Lys Val Gln Ala  Asn Thr Ala Ile Lys  Gly Val Met
        1190                 1195                 1200

Asn Pro  Tyr Val Ser Gly Tyr  Leu Ala Met Trp Val  Pro Val Gly
        1205                 1210                 1215

Ala Ser  Ala Thr Gln Asp Ala  Arg Thr Ala Ala Ser  Thr Lys Thr
        1220                 1225                 1230

Thr Thr  Asp Gly Ser Val Phe  His Ser Asn Ala Ala  Leu Asp Ser
        1235                 1240                 1245
```

```
Asn Leu Ile Tyr Glu Gly Phe Ser Asn Phe Gln Ala Phe Pro Glu
    1250                1255                1260

Asn Ala Ser Glu Asn Ala Asn Ala Ile Ile Ala Gln Asn Val Asp
    1265                1270                1275

Leu Phe Asn Ser Trp Gly Val Thr Ser Phe Gln Leu Ala Pro Gln
    1280                1285                1290

Tyr Val Ser Ser His Asp Gly Ser Phe Leu Asp Ser Ile Ile Asp
    1295                1300                1305

Asn Gly Tyr Ala Phe Thr Asp Arg Tyr Asp Leu Ala Met Ser Lys
    1310                1315                1320

Asn Asn Lys Tyr Gly Ser Tyr Gln Asp Leu Val Asn Val Leu Lys
    1325                1330                1335

Ala Leu His Ala Gly Gly Ile Gln Val Ile Ala Asp Trp Val Pro
    1340                1345                1350

Asp Gln Ile Tyr Ser Leu Pro Gly Lys Glu Val Val Ser Val Val
    1355                1360                1365

Arg Ser Asp Glu Phe Gly Asn Lys Val Asp Gly Thr Gln Ile Asp
    1370                1375                1380

Asn Thr Leu Tyr Val Val Asn Thr Ile Gly Gly Gln Tyr Gln
    1385                1390                1395

Lys Glu Tyr Gly Gly Arg Tyr Leu Glu Glu Leu Lys Gln Lys Tyr
    1400                1405                1410

Pro Glu Leu Phe Lys Thr Lys Gln Pro Ser Thr Gly Val Thr Ile
    1415                1420                1425

Asp Pro Ser Glu Lys Ile Thr Glu Trp Ser Ala Lys Tyr Leu Asn
    1430                1435                1440

Gly Thr Asn Ile Leu His Arg Gly Ala Glu Phe Val Leu Arg Asp
    1445                1450                1455

Gly Ala Thr Tyr Phe Arg Val Ala Glu Thr Ser Glu Val Phe Leu
    1460                1465                1470

Pro Ser Gln Leu Arg Gly Lys Ile Thr Lys Asn Gly Phe Trp Lys
    1475                1480                1485

Asn Asp Ala Gly Lys Val Asn Tyr Tyr Asn Ser Glu Gly Glu Ile
    1490                1495                1500

Met Lys Asn Ala Phe Val Lys Asp Gly Lys Asn Trp Tyr Tyr
    1505                1510                1515

Phe Asp Asn Asp Gly Asn Met Val Thr Asn Thr Ala Leu Thr Ile
    1520                1525                1530

Asp Ser Asp Ala Gln Val Ala Asp Tyr Tyr Phe Leu Asn Asn Gly
    1535                1540                1545

Ile Ser Leu Arg Asp Gly Phe Val Gln Leu Ala Asn Gly Asp Ile
    1550                1555                1560

Tyr Tyr Tyr Asp Val Asn Gly Arg Lys Leu Lys Asn Gly Lys Val
    1565                1570                1575

Thr Val Asn Asn Val Glu Tyr Thr Thr Asp Lys Asn Gly Lys Val
    1580                1585                1590

Val Gly Glu Asn Val Leu Lys Lys Leu Asp Glu Ile Ile Thr Thr
    1595                1600                1605

Gly Lys Thr Thr Leu Ile
    1610

<210> SEQ ID NO 4
<211> LENGTH: 1600
<212> TYPE: PRT
```

<213> ORGANISM: Streptococcus salivarius

<400> SEQUENCE: 4

```
Met Glu Asn Lys Val Arg Tyr Lys Leu His Lys Val Lys Gln Trp
1               5                   10                  15

Val Thr Leu Ala Val Ala Ser Val Ala Leu Ala Thr Ile Ile Gly Gly
            20                  25                  30

Ser Val Ala Thr Ser Ser Leu Ala Ser Ala Glu Glu Thr Asn Asn Ser
            35                  40                  45

Asn Gly Ser Pro Ser Thr Thr Val Gly Glu Asn Thr Asn Pro Val
    50                  55                  60

Val Glu Lys Glu Val Gly Thr Thr Thr Glu Val Ala Asn Thr Ser Asn
65                  70                  75                  80

Ala Thr Thr Thr Glu Arg Ala Glu Val Thr Ala Asp Lys Pro Ala Glu
                85                  90                  95

Thr Thr Val Gln Pro Asn Ser Gly Thr Thr Ser Asp Arg Ala Val
            100                 105                 110

Ala Val Glu Val Glu Ala Lys Pro Glu Thr Thr Ala Lys Pro Glu Val
            115                 120                 125

Ala Thr Lys Pro Glu Thr Ala Thr Thr Ser Glu Val Ala Ala Asn Ala
        130                 135                 140

Gly Val Ala Ala Pro Thr Thr Glu Lys Ser Lys Glu Leu Ser Glu Ala
145                 150                 155                 160

Glu Ile Lys Ala Ala Val Ser Leu Asp Asn Ile Lys Lys Glu Lys Asp
                165                 170                 175

Gly Lys Tyr Tyr Tyr Leu Leu Glu Asp Gly Ser His Lys Lys Asn Phe
            180                 185                 190

Ala Ile Thr Val Asn Gly Gln Val Leu Tyr Phe Asp Glu Asn Gly Ala
        195                 200                 205

Leu Ser Ser Thr Ser Thr Tyr Ser Phe Thr Gln Glu Thr Thr Asn Leu
    210                 215                 220

Val Thr Asp Phe Thr Lys Asn Asn Ala Ala Tyr Asp Ser Thr Lys Ala
225                 230                 235                 240

Ser Phe Glu Leu Val Asp Gly Tyr Leu Thr Ala Asp Ser Trp Tyr Arg
                245                 250                 255

Pro Lys Glu Ile Leu Glu Ala Gly Thr Thr Trp Lys Ala Ser Thr Glu
            260                 265                 270

Lys Asp Phe Arg Pro Leu Leu Met Ser Trp Trp Pro Asp Lys Asp Thr
        275                 280                 285

Gln Val Ala Tyr Leu Asn Tyr Met Thr Lys Ala Leu Ser Asn Gly Glu
    290                 295                 300

Glu Thr Lys Asp Val Phe Thr Ile Glu Asn Ser Gln Ala Ser Leu Asn
305                 310                 315                 320

Ala Ala Ala Gln Ile Leu Gln Arg Lys Ile Glu Val Lys Ile Ala Ala
                325                 330                 335

Asn Lys Ser Thr Asp Trp Leu Arg Gln Ser Ile Glu Ala Phe Val Lys
            340                 345                 350

Asp Gln Asp Lys Trp Asn Ile Asn Ser Glu Ser Pro Gly Lys Glu His
        355                 360                 365

Phe Gln Lys Gly Ala Leu Leu Phe Val Asn Ser Asp Ser Thr Lys Trp
    370                 375                 380

Ala Asn Ser Asp Tyr Arg Lys Leu Asn Gln Thr Ala Thr Ser Tyr Ile
385                 390                 395                 400
```

```
Lys Asn His Lys Ile Val Asn Gly Ser Asp Gly Gly Tyr Glu Phe Leu
                405                 410                 415
Leu Ser Asn Asp Ile Asp Asn Ser Asn Pro Val Val Gln Ala Glu Met
            420                 425                 430
Leu Asn Gln Leu Tyr Tyr Phe Met Asn Trp Gly Gln Ile Val Phe Gly
        435                 440                 445
Asp Lys Asp Lys Asp Ala His Phe Asp Gly Ile Arg Val Asp Ala Val
    450                 455                 460
Asp Asn Val Ser Val Asp Met Leu Gln Leu Val Ser Ser Tyr Met Lys
465                 470                 475                 480
Ala Ala Tyr Lys Val Asn Glu Ser Glu Ala Arg Ala Leu Ala Asn Ile
            485                 490                 495
Ser Ile Leu Glu Ala Trp Ser His Asn Asp Pro Tyr Tyr Val Asn Glu
        500                 505                 510
His Asn Thr Ala Ala Leu Ser Met Asp Asn Gly Leu Arg Leu Ser Ile
    515                 520                 525
Val His Gly Leu Thr Arg Pro Val Thr Asn Lys Gly Thr Gly Ala Arg
    530                 535                 540
Asn Ala Ser Met Lys Asp Leu Ile Asn Gly Gly Tyr Phe Gly Leu Ser
545                 550                 555                 560
Asn Arg Ala Glu Val Thr Ser Tyr Asp Gln Leu Gly Phe Ala Thr Tyr
            565                 570                 575
Leu Phe Val Arg Ala His Asp Ser Glu Val Gln Thr Val Ile Ala Asp
        580                 585                 590
Ile Ile Ser Lys Lys Ile Asp Pro Thr Thr Asp Gly Phe Thr Phe Thr
    595                 600                 605
Leu Asp Gln Leu Lys Gln Ala Phe Asp Ile Tyr Asn Ala Asp Met Leu
    610                 615                 620
Lys Val Asp Lys Glu Tyr Thr His Ser Asn Ile Pro Ala Ala Tyr Ala
625                 630                 635                 640
Leu Met Leu Gln Thr Met Gly Ala Ala Thr Arg Val Tyr Tyr Gly Asp
            645                 650                 655
Leu Tyr Thr Asp Asn Gly Gln Tyr Met Ala Lys Lys Ser Pro Tyr Phe
        660                 665                 670
Asp Gln Ile Thr Thr Leu Leu Lys Ala Arg Pro Lys Tyr Val Ala Gly
    675                 680                 685
Gly Gln Thr Ser Tyr Ile His Asn Leu Ala Gly Asp Gly Val Ser Ser
    690                 695                 700
Ala Lys Asp Asn Lys Glu Val Leu Val Ser Val Arg Tyr Gly Gln Asp
705                 710                 715                 720
Leu Met Ser Lys Thr Asp Thr Glu Gly Gly Lys Tyr Gly Arg Asn Ser
            725                 730                 735
Gly Met Leu Thr Leu Ile Ala Asn Asn Pro Asp Leu Lys Leu Ala Asp
        740                 745                 750
Gly Glu Thr Ile Thr Val Asn Met Gly Ala Ala His Lys Asn Gln Ala
    755                 760                 765
Tyr Arg Pro Leu Leu Leu Gly Thr Asp Lys Gly Ile Val Ser Ser Leu
    770                 775                 780
Asn Asp Ser Asp Thr Lys Val Val Lys Tyr Thr Asp Ala Gln Gly Asn
785                 790                 795                 800
Leu Val Phe Thr Ala Asp Glu Ile Lys Gly Phe Lys Thr Val Asp Met
            805                 810                 815
Ser Gly Tyr Leu Ser Val Trp Val Pro Val Gly Ala Thr Asp Asp Gln
```

```
                820                 825                 830
Asn Val Leu Ala Lys Pro Ser Thr Lys Ala Tyr Lys Glu Gly Asp Lys
            835                 840                 845
Val Tyr Ser Ser Ser Ala Ala Leu Glu Ala Gln Val Ile Tyr Glu Gly
        850                 855                 860
Phe Ser Asn Phe Gln Asp Phe Val Lys Glu Asp Ser Gln Tyr Thr Asn
865                 870                 875                 880
Lys Leu Ile Ala Ala Asn Ala Asp Leu Phe Lys Ser Trp Gly Ile Thr
                885                 890                 895
Ser Phe Glu Ile Ala Pro Gln Tyr Val Ser Ser Lys Asp Gly Thr Phe
            900                 905                 910
Leu Asp Ser Ile Ile Glu Asn Gly Tyr Ala Phe Thr Asp Arg Tyr Asp
        915                 920                 925
Phe Ala Met Ser Lys Asn Asn Lys Tyr Gly Ser Lys Glu Asp Leu Arg
    930                 935                 940
Asp Ala Leu Lys Ala Leu His Lys Gln Gly Ile Gln Val Ile Ala Asp
945                 950                 955                 960
Trp Val Pro Asp Gln Leu Tyr Thr Leu Pro Gly Lys Glu Val Val Thr
                965                 970                 975
Ala Thr Arg Thr Asp Thr His Gly Lys Val Leu Asp Asp Thr Ser Leu
            980                 985                 990
Val Asn Lys Leu Tyr Val Thr Asn Thr Lys Ser Ser Gly Asn Asp Phe
        995                 1000                 1005
Gln Ala Gln Tyr Gly Gly Ala Phe Leu Asp Lys Leu Gln Lys Leu
    1010                 1015                 1020
Tyr Pro Glu Ile Phe Lys Glu Val Met Glu Ala Ser Gly Lys Thr
    1025                 1030                 1035
Ile Asp Pro Ser Val Lys Ile Lys Gln Trp Glu Ala Lys Tyr Phe
    1040                 1045                 1050
Asn Gly Thr Asn Ile Gln Lys Arg Gly Ser Asp Tyr Val Leu Ser
    1055                 1060                 1065
Asp Gly Lys Leu Tyr Phe Thr Val Asn Asp Lys Gly Thr Phe Leu
    1070                 1075                 1080
Pro Ala Ala Leu Thr Gly Asp Thr Lys Ala Lys Thr Gly Phe Ala
    1085                 1090                 1095
Tyr Asp Gly Thr Gly Val Thr Tyr Tyr Thr Thr Ser Gly Thr Gln
    1100                 1105                 1110
Ala Lys Ser Gln Phe Val Thr Tyr Asn Gly Lys Gln Tyr Tyr Phe
    1115                 1120                 1125
Asn Asp Lys Gly Tyr Leu Val Thr Gly Glu Gln Thr Ile Asp Gly
    1130                 1135                 1140
Ser Asn Tyr Phe Phe Leu Pro Asn Gly Val Met Phe Thr Asp Gly
    1145                 1150                 1155
Val Arg Lys Asn Ala Lys Gly Gln Ser Leu Val Tyr Gly Lys Ser
    1160                 1165                 1170
Gly Lys Leu Thr Thr Gln Thr Gly Trp Lys Glu Val Thr Val Lys
    1175                 1180                 1185
Asp Asp Ser Gly Lys Glu Glu Lys Phe Tyr Gln Tyr Phe Phe Lys
    1190                 1195                 1200
Gly Gly Ile Met Ala Thr Gly Leu Thr Glu Val Glu Gly Lys Glu
    1205                 1210                 1215
Lys Tyr Phe Tyr Asp Asn Gly Tyr Gln Ala Lys Gly Val Phe Val
    1220                 1225                 1230
```

Pro Thr Lys Asp Gly His Leu Met Phe Phe Cys Gly Asp Ser Gly
    1235                1240                1245

Glu Arg Lys Tyr Ser Gly Phe Phe Glu Gln Asp Gly Asn Trp Tyr
    1250                1255                1260

Tyr Ala Asn Asp Lys Gly Tyr Val Ala Thr Gly Phe Thr Lys Val
    1265                1270                1275

Gly Lys Gln Asn Leu Tyr Phe Asn Glu Lys Gly Val Gln Val Lys
    1280                1285                1290

Asn Arg Phe Phe Gln Val Gly Asp Ala Thr Tyr Ala Asn Asn
    1295                1300                1305

Glu Gly Asp Val Leu Arg Gly Ala Gln Thr Ile Asn Gly Asp Glu
    1310                1315                1320

Leu Tyr Phe Asp Glu Ser Gly Lys Gln Val Lys Gly Glu Phe Val
    1325                1330                1335

Asn Asn Pro Asp Gly Thr Thr Ser Tyr Tyr Asp Ala Ile Thr Gly
    1340                1345                1350

Val Lys Leu Val Asp Thr Ser Leu Val Val Asp Gly Gln Thr Phe
    1355                1360                1365

Asn Val Asp Ala Lys Gly Val Val Thr Lys Ala His Thr Pro Gly
    1370                1375                1380

Phe Tyr Thr Thr Gly Asp Asn Asn Trp Phe Tyr Ala Asp Ser Tyr
    1385                1390                1395

Gly Arg Asn Val Thr Gly Ala Gln Val Ile Asn Gly Gln His Leu
    1400                1405                1410

Tyr Phe Asp Ala Asn Gly Arg Gln Val Lys Gly Gly Phe Val Thr
    1415                1420                1425

Asn Thr Asp Gly Ser Arg Ser Phe Tyr His Trp Asn Thr Gly Asp
    1430                1435                1440

Lys Leu Val Ser Thr Phe Phe Thr Thr Gly His Asp Arg Trp Tyr
    1445                1450                1455

Tyr Ala Asp Asp Arg Gly Asn Val Val Thr Gly Ala Gln Val Ile
    1460                1465                1470

Asn Gly Gln Lys Leu Phe Phe Asp Thr Asp Gly Lys Gln Val Lys
    1475                1480                1485

Gly Ala Phe Ala Thr Asn Ala Asn Gly Ser Arg Ser Tyr Tyr His
    1490                1495                1500

Trp Asn Thr Gly Asn Lys Leu Val Ser Thr Phe Phe Thr Ser Gly
    1505                1510                1515

Asp Asn Asn Trp Tyr Tyr Ala Asp Ala Lys Gly Glu Val Val Val
    1520                1525                1530

Gly Glu Gln Thr Ile Asn Gly Gln His Leu Tyr Phe Asp Gln Thr
    1535                1540                1545

Gly Lys Gln Val Lys Gly Ala Thr Ala Thr Asn Pro Asp Gly Ser
    1550                1555                1560

Ile Ser Tyr Tyr Asp Val His Thr Gly Glu Lys Ala Ile Asn Arg
    1565                1570                1575

Trp Val Lys Ile Pro Ser Gly Gln Trp Val Tyr Phe Asn Ala Gln
    1580                1585                1590

Gly Lys Gly Tyr Val Ser Asn
    1595                1600

<210> SEQ ID NO 5
<211> LENGTH: 4677

```
<212> TYPE: DNA
<213> ORGANISM: Streptococcus salivarius

<400> SEQUENCE: 5
gaagaaacaa ataactctaa tggatcacct tcaacaacta cggtcgggga aaatacaaat      60
cctgtggttg aaaaagaggt aggcacaaca actgaggtag caaatacttc aaatgccaca     120
acaacagagc gagcagaagt tactgctgac aaaccagctg aaacgacggt tcaaccaaat     180
tcaggaacaa ctacaagtga tagagctgta gcagtagagg ttgaagccaa acctgaaacg     240
actgctaagc cagaagttgc tactaaacca gaaacagcta caacatcaga agtcgctgca     300
aatgctggag tagctgctcc aacgactgag aagtctaaag agctttctga agccgaaatt     360
aaggctgcag tctcactcga taatattaaa aagaaaaag atggtaaata ttactatctt     420
ttagaagatg gatcacacaa gaaaaacttt gccattactg taaatggtca ggtcctttat     480
tttgatgaaa atggtgccct ttcaagcaca tcaacgtatt catttacaca agaaacaaca     540
aatctagtca ctgattttac aaaaaataat gctgcctacg attcaactaa agcgagcttt     600
gaacttgttg atggttattt gacagcagac agttggtacc gtccaaaaga aatccttgaa     660
gctggtacaa cttggaaagc gtcaactgaa aaagattttc gtccactttt gatgtcttgg     720
tggcctgata aggatactca agtagcttac ttgaattaca tgactaaggc tcttagcaac     780
ggtgaagaaa caaagatgt ctttacgatt gaaaattctc aagcgagctt gaatgccgca     840
gctcaaatcc tccaacgtaa gattgaagtt aagattgctg ctaataagtc aacagactgg     900
ttgcgtcagt caatcgaggc ttttgttaaa gaccaagata atggaacat taattctgaa     960
tcgccaggta aggaacactt ccaaaaaggt gcgcttcttt ttgtgaacag cgattcaact    1020
aaatgggcta actctgatta tcgtaaactt aatcaaacgg cgacaagtta tattaaaaat    1080
cataagattg ttaatggtag cgatggtggt tatgaattct tgctctcaaa tgacattgac    1140
aactctaatc cagtcgttca agcagaaatg cttaaccaat tgtattactt tatgaactgg    1200
ggacaaatcg tctttggtga taggacaag gatgctcact ttgatggtat acgtgttgat    1260
gctgtggata tgttagcgt tgacatgctt caattagtgt cttcatacat gaaggctgca    1320
tacaaggtta atgagtcgga agctcgtgcc cttgcgaata tctctattct tgaagcatgg    1380
tcacacaatg acccatatta tgtgaatgag cacaacacag cagctctttc tatggataat    1440
ggtctccgtt tgtcaattgt tcacggatta actcgtccag taactaataa aggtacaggt    1500
gcacgtaatg catcaatgaa ggaccttatt aacggaggtt atttcggtct ctcaaaccgt    1560
gcagaagtca cttcatatga tcaacttggt tttgcaacct acctctttgt tcgtgcacat    1620
gactcagaag ttcaaacggt tatcgcagac attatcagta aaaaattga tcctacaaca    1680
gatggtttca ctttcacatt agatcaattg aaacaagcat tcgatattta taatgctgat    1740
atgttgaaag ttgataagga atatacgcat tcaaatattc ctgctgccta tgctttgatg    1800
cttcaaacaa tgggtgcggc aacacgtgtt tattatggag atttgtatac tgataatggt    1860
caatacatgg ctaagaaatc accatacttt gatcaaatca aactcttct taaagcgcgt    1920
cctaagtatg tagctggtgg tcaaacatct tatatccaca accttgctgg tgatggggta    1980
tcatctgcta aagacaataa agaagttctt gtctctgtcc gttatggtca agatttgatg    2040
tctaagacag atacagaagg tggaaaatac ggtcgcaatt caggtatgtt gacccttatt    2100
gctaataacc cggatttgaa attagcagat ggtgaaacta ttactgtaaa tatgggtgca    2160
gctcacaaga accaagccta ccgtccactc ttgcttggta cggataaagg tatcgtgtca    2220
```

```
tcattgaatg attcagatac taaggttgtt aaatatacag atgcacaagg aaatcttgtc    2280
ttcacagctg atgaaatcaa aggctttaag actgttgata tgagtggtta cctttcagtt    2340
tgggtaccag taggtgcgac tgacgatcaa aacgttcttg ctaaaccatc aacaaaagcc    2400
tacaaagaag gggataaggt ttatagttct tctgcagcac ttgaagcaca agtgatttac    2460
gaaggcttct caaacttcca agactttgtt aaagaagata gtcaatacac taataaattg    2520
attgcagcta atgcagacct cttcaagtca tggggcatta cgtcatttga aattgcacct    2580
caatatgtct catctaagga tggaactttc cttgattcta ttattgagaa tggttatgcc    2640
ttcacagacc gttatgactt tgccatgagc aaaaacaata aatacggttc aaaagaagat    2700
cttcgtgatg ctctcaaggc tcttcacaaa caaggtattc aagtcattgc tgactgggtt    2760
ccagaccaat tgtacaccct tccaggtaaa aagtagtga ctgctacgcg tactgataca    2820
catggtaagg tccttgatga tactagcttg gttaataaac tttatgtgac aaataccaag    2880
tcatcaggta atgatttcca agcccagtac ggtggtgcct tcctcgacaa acttcaaaaa    2940
ctttatccag aaatcttcaa agaagttatg gaagcgtctg gtaagacaat tgatccatct    3000
gtgaagatta aacagtggga agctaaatac tttaacggta caaacatcca aaaacgtggt    3060
tctgactatg ttctcagcga tggtaaattg tacttcaccg ttaacgataa aggtaccttc    3120
ctcccagcag ccttgactgg tgatacaaaa gctaagactg ttttgccta tgatggtaca    3180 ggtgtaactt attacacaac atcaggtact caagctaaga gtcagtttgt aacttataac    3240
ggtaagcaat actactttaa cgataagggt taccttgtaa ctggtgaaca aactatcgat    3300
ggttctaact atttcttctt gccaaatggt gtcatgttta ctgatggtgt cagaaaaaat    3360
gccaaaggtc aatcattggt ttatggtaag tcaggtaaat tgacgactca aactggttgg    3420
aaagaagtta ccgttaaaga tgatagtggt aaggaagaga aattctacca atacttcttc    3480
aagggtggta tcatggctac tggtttgact gaagtagaag gtaaggaaaa atacttctat    3540
gataatggtt accaagctaa aggtgtcttc gttcctacaa aagacggcca tttaatgttc    3600
ttctgtggtg attcaggcga acgtaagtac tcaggcttct ttgaacaaga tggtaactgg    3660
tactacgcca atgataaagg ctatgttgct actgggttta ctaaggtagg taaacaaaac    3720
ctttacttca atgaaaaagg tgttcaagtt aagaatcgct tcttccaagt tggtgatgct    3780
acatactatg caaataacga aggtgacgtt cttcgtggtg ctcaaaccat caatggagac    3840
gaactctact ttgatgaatc aggtaaacaa gttaaaggtg agttcgtgaa caatcctgat    3900
ggtacgactt catactacga tgcaatcaca ggtgtgaaac ttgttgatac atcactggta    3960
gttgatggtc aaacctttaa tgtcgatgct aagggtgttg tgactaaggc acatacacca    4020
ggcttctata ctactgggga caacaactgg ttctatgcag actcatatgg acgtaatgtc    4080
acaggtgctc aggtcatcaa tggtcaacac ctctactttg atgctaatgg tcgccaagtt    4140
aagggtggct tcgtaacgaa cactgacggt agtcgttcat tctaccactg gaataccggt    4200
gataaattgg tatcaacctt cttcactacc ggtcatgata gatggtatta tgctgatgat    4260
aggggtaatg tcgttacagg agctcaagtt atcaacggtc aaaaactctt ctttgatact    4320
gatggtaagc aggttaaagg tgctttcgca acaaatgcga atggtagtcg ctcatactac    4380
cactggaata ctggtaataa gttagtatca accttcttca caagtggaga taacaactgg    4440
tattatgcag atgccaaggg tgaagttgtt gttggcgaac agacgatcaa cggtcaacac    4500
ctttactttg accaaactgg taagcaagtg aaggggggcaa ctgctacgaa tcctgatggc    4560
tcaatctctt actatgatgt tcatacaggg gaaaaggcta ttaatcgttg ggttaaaatt    4620
```
ccttcagggc aatgggtata cttcaacgct caaggaaaag gctacgtgtc aaattaa    4677

<210> SEQ ID NO 6
<211> LENGTH: 1558
<212> TYPE: PRT
<213> ORGANISM: Streptococcus salivarius

<400> SEQUENCE: 6

```
Glu Glu Thr Asn Asn Ser Asn Gly Ser Pro Ser Thr Thr Thr Val Gly
1               5                   10                  15

Glu Asn Thr Asn Pro Val Val Glu Lys Glu Val Gly Thr Thr Thr Glu
            20                  25                  30

Val Ala Asn Thr Ser Asn Ala Thr Thr Thr Glu Arg Ala Glu Val Thr
        35                  40                  45

Ala Asp Lys Pro Ala Glu Thr Thr Val Gln Pro Asn Ser Gly Thr Thr
    50                  55                  60

Thr Ser Asp Arg Ala Val Ala Val Glu Val Glu Ala Lys Pro Glu Thr
65                  70                  75                  80

Thr Ala Lys Pro Glu Val Ala Thr Lys Pro Glu Thr Ala Thr Thr Ser
                85                  90                  95

Glu Val Ala Ala Asn Ala Gly Val Ala Ala Pro Thr Thr Glu Lys Ser
            100                 105                 110

Lys Glu Leu Ser Glu Ala Glu Ile Lys Ala Ala Val Ser Leu Asp Asn
        115                 120                 125

Ile Lys Lys Glu Lys Asp Gly Lys Tyr Tyr Tyr Leu Leu Glu Asp Gly
    130                 135                 140

Ser His Lys Lys Asn Phe Ala Ile Thr Val Asn Gly Gln Val Leu Tyr
145                 150                 155                 160

Phe Asp Glu Asn Gly Ala Leu Ser Ser Thr Ser Thr Tyr Ser Phe Thr
                165                 170                 175

Gln Glu Thr Thr Asn Leu Val Thr Asp Phe Thr Lys Asn Asn Ala Ala
            180                 185                 190

Tyr Asp Ser Thr Lys Ala Ser Phe Glu Leu Val Asp Gly Tyr Leu Thr
        195                 200                 205

Ala Asp Ser Trp Tyr Arg Pro Lys Glu Ile Leu Glu Ala Gly Thr Thr
    210                 215                 220

Trp Lys Ala Ser Thr Glu Lys Asp Phe Arg Pro Leu Leu Met Ser Trp
225                 230                 235                 240

Trp Pro Asp Lys Asp Thr Gln Val Ala Tyr Leu Asn Tyr Met Thr Lys
                245                 250                 255

Ala Leu Ser Asn Gly Glu Glu Thr Lys Asp Val Phe Thr Ile Glu Asn
            260                 265                 270

Ser Gln Ala Ser Leu Asn Ala Ala Gln Ile Leu Gln Arg Lys Ile
        275                 280                 285

Glu Val Lys Ile Ala Ala Asn Lys Ser Thr Asp Trp Leu Arg Gln Ser
    290                 295                 300

Ile Glu Ala Phe Val Lys Asp Gln Asp Lys Trp Asn Ile Asn Ser Glu
305                 310                 315                 320

Ser Pro Gly Lys Glu His Phe Lys Gly Ala Leu Leu Phe Val Asn
                325                 330                 335

Ser Asp Ser Thr Lys Trp Ala Asn Ser Asp Tyr Arg Lys Leu Asn Gln
            340                 345                 350

Thr Ala Thr Ser Tyr Ile Lys Asn His Lys Ile Val Asn Gly Ser Asp
        355                 360                 365
```

```
Gly Gly Tyr Glu Phe Leu Leu Ser Asn Asp Ile Asp Asn Ser Asn Pro
        370                 375                 380

Val Val Gln Ala Glu Met Leu Asn Gln Leu Tyr Tyr Phe Met Asn Trp
385                 390                 395                 400

Gly Gln Ile Val Phe Gly Asp Lys Asp Lys Asp Ala His Phe Asp Gly
                405                 410                 415

Ile Arg Val Asp Ala Val Asp Asn Val Ser Val Asp Met Leu Gln Leu
                420                 425                 430

Val Ser Ser Tyr Met Lys Ala Ala Tyr Lys Val Asn Glu Ser Glu Ala
                435                 440                 445

Arg Ala Leu Ala Asn Ile Ser Ile Leu Glu Ala Trp Ser His Asn Asp
450                 455                 460

Pro Tyr Tyr Val Asn Glu His Asn Thr Ala Ala Leu Ser Met Asp Asn
465                 470                 475                 480

Gly Leu Arg Leu Ser Ile Val His Gly Leu Thr Arg Pro Val Thr Asn
                485                 490                 495

Lys Gly Thr Gly Ala Arg Asn Ala Ser Met Lys Asp Leu Ile Asn Gly
                500                 505                 510

Gly Tyr Phe Gly Leu Ser Asn Arg Ala Glu Val Thr Ser Tyr Asp Gln
                515                 520                 525

Leu Gly Phe Ala Thr Tyr Leu Phe Val Arg Ala His Asp Ser Glu Val
                530                 535                 540

Gln Thr Val Ile Ala Asp Ile Ile Ser Lys Lys Ile Asp Pro Thr Thr
545                 550                 555                 560

Asp Gly Phe Thr Phe Thr Leu Asp Gln Leu Lys Gln Ala Phe Asp Ile
                565                 570                 575

Tyr Asn Ala Asp Met Leu Lys Val Asp Lys Glu Tyr Thr His Ser Asn
                580                 585                 590

Ile Pro Ala Ala Tyr Ala Leu Met Leu Gln Thr Met Gly Ala Ala Thr
                595                 600                 605

Arg Val Tyr Tyr Gly Asp Leu Tyr Thr Asp Asn Gly Gln Tyr Met Ala
                610                 615                 620

Lys Lys Ser Pro Tyr Phe Asp Gln Ile Thr Thr Leu Leu Lys Ala Arg
625                 630                 635                 640

Pro Lys Tyr Val Ala Gly Gly Gln Thr Ser Tyr Ile His Asn Leu Ala
                645                 650                 655

Gly Asp Gly Val Ser Ser Ala Lys Asp Asn Lys Glu Val Leu Val Ser
                660                 665                 670

Val Arg Tyr Gly Gln Asp Leu Met Ser Lys Thr Asp Thr Glu Gly Gly
                675                 680                 685

Lys Tyr Gly Arg Asn Ser Gly Met Leu Thr Leu Ile Ala Asn Asn Pro
690                 695                 700

Asp Leu Lys Leu Ala Asp Gly Glu Thr Ile Thr Val Asn Met Gly Ala
705                 710                 715                 720

Ala His Lys Asn Gln Ala Tyr Arg Pro Leu Leu Gly Thr Asp Lys
                725                 730                 735

Gly Ile Val Ser Ser Leu Asn Asp Ser Asp Thr Lys Val Val Lys Tyr
                740                 745                 750

Thr Asp Ala Gln Gly Asn Leu Val Phe Thr Ala Asp Glu Ile Lys Gly
                755                 760                 765

Phe Lys Thr Val Asp Met Ser Gly Tyr Leu Ser Val Trp Val Pro Val
770                 775                 780
```

-continued

Gly Ala Thr Asp Asp Gln Asn Val Leu Ala Lys Pro Ser Thr Lys Ala
785                 790                 795                 800

Tyr Lys Glu Gly Asp Lys Val Tyr Ser Ser Ala Ala Leu Glu Ala
            805                 810                 815

Gln Val Ile Tyr Glu Gly Phe Ser Asn Phe Gln Asp Phe Val Lys Glu
            820                 825                 830

Asp Ser Gln Tyr Thr Asn Lys Leu Ile Ala Ala Asn Ala Asp Leu Phe
            835                 840                 845

Lys Ser Trp Gly Ile Thr Ser Phe Glu Ile Ala Pro Gln Tyr Val Ser
850                 855                 860

Ser Lys Asp Gly Thr Phe Leu Asp Ser Ile Ile Glu Asn Gly Tyr Ala
865                 870                 875                 880

Phe Thr Asp Arg Tyr Asp Phe Ala Met Ser Lys Asn Asn Lys Tyr Gly
                885                 890                 895

Ser Lys Glu Asp Leu Arg Asp Ala Leu Lys Ala Leu His Lys Gln Gly
            900                 905                 910

Ile Gln Val Ile Ala Asp Trp Val Pro Asp Gln Leu Tyr Thr Leu Pro
            915                 920                 925

Gly Lys Glu Val Val Thr Ala Thr Arg Thr Asp Thr His Gly Lys Val
930                 935                 940

Leu Asp Asp Thr Ser Leu Val Asn Lys Leu Tyr Val Thr Asn Thr Lys
945                 950                 955                 960

Ser Ser Gly Asn Asp Phe Gln Ala Gln Tyr Gly Gly Ala Phe Leu Asp
                965                 970                 975

Lys Leu Gln Lys Leu Tyr Pro Glu Ile Phe Lys Glu Val Met Glu Ala
            980                 985                 990

Ser Gly Lys Thr Ile Asp Pro Ser Val Lys Ile Lys Gln Trp Glu Ala
            995                 1000                1005

Lys Tyr Phe Asn Gly Thr Asn Ile Gln Lys Arg Gly Ser Asp Tyr
    1010                1015                1020

Val Leu Ser Asp Gly Lys Leu Tyr Phe Thr Val Asn Asp Lys Gly
    1025                1030                1035

Thr Phe Leu Pro Ala Ala Leu Thr Gly Asp Thr Lys Ala Lys Thr
    1040                1045                1050

Gly Phe Ala Tyr Asp Gly Thr Gly Val Thr Tyr Tyr Thr Thr Ser
    1055                1060                1065

Gly Thr Gln Ala Lys Ser Gln Phe Val Thr Tyr Asn Gly Lys Gln
    1070                1075                1080

Tyr Tyr Phe Asn Asp Lys Gly Tyr Leu Val Thr Gly Glu Gln Thr
    1085                1090                1095

Ile Asp Gly Ser Asn Tyr Phe Phe Leu Pro Asn Gly Val Met Phe
    1100                1105                1110

Thr Asp Gly Val Arg Lys Asn Ala Lys Gly Gln Ser Leu Val Tyr
    1115                1120                1125

Gly Lys Ser Gly Lys Leu Thr Thr Gln Thr Gly Trp Lys Glu Val
    1130                1135                1140

Thr Val Lys Asp Asp Ser Gly Lys Glu Glu Lys Phe Tyr Gln Tyr
    1145                1150                1155

Phe Phe Lys Gly Gly Ile Met Ala Thr Gly Leu Thr Glu Val Glu
    1160                1165                1170

Gly Lys Glu Lys Tyr Phe Tyr Asp Asn Gly Tyr Gln Ala Lys Gly
    1175                1180                1185

Val Phe Val Pro Thr Lys Asp Gly His Leu Met Phe Phe Cys Gly 1190                1195              1200

Asp Ser Gly Glu Arg Lys Tyr Ser Gly Phe Phe Glu Gln Asp Gly
    1205                1210                1215

Asn Trp Tyr Tyr Ala Asn Asp Lys Gly Tyr Val Ala Thr Gly Phe
    1220                1225                1230

Thr Lys Val Gly Lys Gln Asn Leu Tyr Phe Asn Glu Lys Gly Val
    1235                1240                1245

Gln Val Lys Asn Arg Phe Phe Gln Val Gly Asp Ala Thr Tyr Tyr
    1250                1255                1260

Ala Asn Asn Glu Gly Asp Val Leu Arg Gly Ala Gln Thr Ile Asn
    1265                1270                1275

Gly Asp Glu Leu Tyr Phe Asp Glu Ser Gly Lys Gln Val Lys Gly
    1280                1285                1290

Glu Phe Val Asn Asn Pro Asp Gly Thr Thr Ser Tyr Tyr Asp Ala
    1295                1300                1305

Ile Thr Gly Val Lys Leu Val Asp Thr Ser Leu Val Val Asp Gly
    1310                1315                1320

Gln Thr Phe Asn Val Asp Ala Lys Gly Val Val Thr Lys Ala His
    1325                1330                1335

Thr Pro Gly Phe Tyr Thr Thr Gly Asp Asn Asn Trp Phe Tyr Ala
    1340                1345                1350

Asp Ser Tyr Gly Arg Asn Val Thr Gly Ala Gln Val Ile Asn Gly
    1355                1360                1365

Gln His Leu Tyr Phe Asp Ala Asn Gly Arg Gln Val Lys Gly Gly
    1370                1375                1380

Phe Val Thr Asn Thr Asp Gly Ser Arg Ser Phe Tyr His Trp Asn
    1385                1390                1395

Thr Gly Asp Lys Leu Val Ser Thr Phe Phe Thr Thr Gly His Asp
    1400                1405                1410

Arg Trp Tyr Tyr Ala Asp Asp Arg Gly Asn Val Val Thr Gly Ala
    1415                1420                1425

Gln Val Ile Asn Gly Gln Lys Leu Phe Phe Asp Thr Asp Gly Lys
    1430                1435                1440

Gln Val Lys Gly Ala Phe Ala Thr Asn Ala Asn Gly Ser Arg Ser
    1445                1450                1455

Tyr Tyr His Trp Asn Thr Gly Asn Lys Leu Val Ser Thr Phe Phe
    1460                1465                1470

Thr Ser Gly Asp Asn Asn Trp Tyr Tyr Ala Asp Ala Lys Gly Glu
    1475                1480                1485

Val Val Val Gly Glu Gln Thr Ile Asn Gly Gln His Leu Tyr Phe
    1490                1495                1500

Asp Gln Thr Gly Lys Gln Val Lys Gly Ala Thr Ala Thr Asn Pro
    1505                1510                1515

Asp Gly Ser Ile Ser Tyr Tyr Asp Val His Thr Gly Glu Lys Ala
    1520                1525                1530

Ile Asn Arg Trp Val Lys Ile Pro Ser Gly Gln Trp Val Tyr Phe
    1535                1540                1545

Asn Ala Gln Gly Lys Gly Tyr Val Ser Asn
    1550                1555

<210> SEQ ID NO 7
<211> LENGTH: 26
<212> TYPE: PRT
<213> ORGANISM: Bacillus subtilis -continued

<400> SEQUENCE: 7

Met Arg Ser Lys Lys Leu Trp Ile Ser Leu Leu Phe Ala Leu Thr Leu
1               5                   10                  15

Ile Phe Thr Met Ala Phe Ser Asn Met Ser
            20                  25

<210> SEQ ID NO 8
<211> LENGTH: 36
<212> TYPE: DNA
<213> ORGANISM: artificial sequence
<220> FEATURE:
<223> OTHER INFORMATION: synthetic construct

<400> SEQUENCE: 8
ataaaaaacg ctcggttgcc gccgggcgtt ttttat                       36

<210> SEQ ID NO 9
<211> LENGTH: 21
<212> TYPE: DNA
<213> ORGANISM: artificial sequence
<220> FEATURE:
<223> OTHER INFORMATION: synthetic construct

<400> SEQUENCE: 9
ggatcctgac tgcctgagct t                                       21

<210> SEQ ID NO 10
<211> LENGTH: 8616
<212> TYPE: DNA
<213> ORGANISM: artificial sequence
<220> FEATURE:
<223> OTHER INFORMATION: plasmid pTrex

<400> SEQUENCE: 10
aagcttaact agtacttctc gagctctgta catgtccggt cgcgacgtac gcgtatcgat    60
ggcgccagct gcaggcggcc gcctgcagcc acttgcagtc ccgtggaatt ctcacggtga   120
atgtaggcct tttgtagggt aggaattgtc actcaagcac ccccaacctc cattacgcct   180
cccccataga gttcccaatc agtgagtcat ggcactgttc tcaaatagat tggggagaag   240
ttgacttccg cccagagctg aaggtcgcac aaccgcatga tatagggtcg caacggcaa    300 aaaagcacgt ggctcaccga aaagcaagat gtttgcgatc taacatccag gaacctggat   360
acatccatca tcacgcacga ccactttgat ctgctggtaa actcgtattc gccctaaacc   420
gaagtgcgtg gtaaatctac acgtgggccc ctttcggtat actgcgtgtg tcttctctag   480
gtgccattct tttcccttcc tctagtgttg aattgtttgt gttggagtcc gagctgtaac   540
tacctctgaa tctctggaga atggtggact aacgactacc gtgcacctgc atcatgtata   600
taatagtgat cctgagaagg ggggtttgga gcaatgtggg actttgatgg tcatcaaaca   660
aagaacgaag acgcctcttt tgcaaagttt gtttcggct acggtgaaga actggatact   720
tgttgtgtct tctgtgtatt tttgtggcaa caagaggcca gagacaatct attcaaacac   780
caagcttgct cttttgagct acaagaacct gtggggtata tatctagagt tgtgaagtcg   840
gtaatcccgc tgtatagtaa tacgagtcgc atctaaatac tccgaagctg ctgcgaaccc   900
ggagaatcga gatgtgctgg aaagcttcta gcgagcggct aaattagcat gaaaggctat   960
gagaaattct ggagacggct tgttgaatca tggcgttcca ttcttcgaca agcaaagcgt  1020
tccgtcgcag tagcaggcac tcattcccga aaaaactcgg agattcctaa gtagcgatgg  1080

```
aaccggaata atataatagg caatacattg agttgcctcg acggttgcaa tgcaggggta    1140
ctgagcttgg acataactgt tccgtacccc acctcttctc aacctttggc gtttccctga    1200
ttcagcgtac ccgtacaagt cgtaatcact attaacccag actgaccgga cgtgttttgc    1260
ccttcatttg gagaaataat gtcattgcga tgtgtaattt gcctgcttga ccgactgggg    1320
ctgttcgaag cccgaatgta ggattgttat ccgaactctg ctcgtagagg catgttgtga    1380
atctgtgtcg ggcaggacac gcctcgaagg ttcacggcaa gggaaaccac cgatagcagt    1440
gtctagtagc aacctgtaaa gccgcaatgc agcatcactg gaaaatacaa accaatggct    1500
aaaagtacat aagttaatgc ctaaagaagt catataccag cggctaataa ttgtacaatc    1560
aagtggctaa acgtaccgta atttgccaac ggcttgtggg gttgcagaag caacggcaaa    1620
gccccacttc cccacgtttg tttcttcact cagtccaatc tcagctggtg atcccccaat    1680
tgggtcgctt gtttgttccg gtgaagtgaa agaagacaga ggtaagaatg tctgactcgg    1740
agcgttttgc atacaaccaa gggcagtgat ggaagacagt gaaatgttga cattcaagga    1800
gtatttagcc agggatgctt gagtgtatcg tgtaaggagg tttgtctgcc gatacgacga    1860
atactgtata gtcacttctg atgaagtggt ccatattgaa atgtaagtcg gcactgaaca    1920
ggcaaaagat tgagttgaaa ctgcctaaga tctcgggccc tcgggccttc ggcctttggg    1980
tgtacatgtt tgtgctccgg gcaaatgcaa agtgtggtag gatcgaacac actgctgcct    2040
ttaccaagca gctgagggta tgtgataggc aaatgttcag gggccactgc atggtttcga    2100
atagaaagag aagcttagcc aagaacaata gccgataaag atagcctcat taaacggaat    2160
gagctagtag gcaaagtcag cgaatgtgta tatataaagg ttcgaggtcc gtgcctccct    2220
catgctctcc ccatctactc atcaactcag atcctccagg agacttgtac accatctttt    2280
gaggcacaga aacccaatag tcaaccgcgg actgcgcatc atgtatcgga agttggccgt    2340
catctcggcc ttcttggcca cacctcgtgc tagactaggc gcgccgcgcg ccagctccgt    2400
gcgaaagcct gacgcaccgg tagattcttg gtgagcccgt atcatgacgg cggcgggagc    2460
tacatggccc cgggtgattt attttttttg tatctacttc tgacccttttt caaatatacg    2520 gtcaactcat ctttcactgg agatgcggcc tgcttggtat tgcgatgttg tcagcttggc    2580
aaattgtggc tttcgaaaac acaaaacgat tccttagtag ccatgcattt aagataacg    2640 gaatagaaga aagaggaaat taaaaaaaaa aaaaaaacaa acatcccgtt cataacccgt    2700
agaatcgccg ctcttcgtgt atcccagtac cagtttattt tgaatagctc gcccgctgga    2760
gagcatcctg aatgcaagta acaaccgtag aggctgacac ggcaggtgtt gctagggagc    2820
gtcgtgttct acaaggccag acgtcttcgc ggttgatata tatgtatgtt tgactgcagg    2880
ctgctcagcg acgacagtca agttcgccct cgctgcttgt gcaataatcg cagtggggaa    2940
gccacaccgt gactcccatc tttcagtaaa gctctgttgg tgtttatcag caatacacgt    3000
aatttaaact cgttagcatg gggctgatag cttaattacc gtttaccagt gccatggttc    3060
tgcagctttc cttggcccgt aaaattcggc gaagccagcc aatcaccagc taggcaccag    3120
ctaaacccta taattagtct cttatcaaca ccatccgctc cccgggatc aatgaggaga    3180 atgaggggga tgcggggcta aagaagccta cataaccctc atgccaactc ccagtttaca    3240
ctcgtcgagc caacatcctg actataagct aacacagaat gcctcaatcc tgggaagaac    3300
tggccgctga taagcgcgcc cgcctcgcaa aaaccatccc tgatgaatgg aaagtccaga    3360
cgctgcctgc ggaagacagc gttattgatt tcccaaagaa atcggggatc cttttcagagg   3420 ccgaactgaa gatcacagag gcctccgctg cagatcttgt gtccaagctg gcggccggag    3480
```

```
agttgacctc ggtggaagtt acgctagcat tctgtaaacg ggcagcaatc gcccagcagt   3540
tagtagggtc ccctctacct ctcagggaga tgtaacaacg ccaccttatg ggactatcaa   3600
gctgacgctg gcttctgtgc agacaaactg cgcccacgag ttcttccctg acgccgctct   3660
cgcgcaggca agggaactcg atgaatacta cgcaaagcac aagagacccg ttggtccact   3720
ccatggcctc cccatctctc tcaaagacca gcttcgagtc aaggtacacc gttgccccta   3780
agtcgttaga tgtccctttt tgtcagctaa catatgccac cagggctacg aaacatcaat   3840
gggctacatc tcatggctaa acaagtacga cgaaggggac tcggttctga caaccatgct   3900
ccgcaaagcc ggtgccgtct tctacgtcaa gacctctgtc ccgcagaccc tgatggtctg   3960
cgagacagtc aacaacatca tcgggcgcac cgtcaaccca cgcaacaaga actggtcgtg   4020
cggcggcagt tctggtggtg agggtgcgat cgttgggatt cgtggtggcg tcatcggtgt   4080
aggaacggat atcggtggct cgattcgagt gccggccgcg ttcaacttcc tgtacggtct   4140
aaggccgagt catgggcggc tgccgtatgc aaagatggcg aacagcatgg agggtcagga   4200
gacggtgcac agcgttgtcg ggccgattac gcactctgtt gagggtgagt ccttcgcctc   4260
ttccttcttt tcctgctcta taccaggcct ccactgtcct cctttcttgc tttttatact   4320
atatacgaga ccggcagtca ctgatgaagt atgttagacc tccgcctctt caccaaatcc   4380
gtcctcggtc aggagccatg gaaatacgac tccaaggtca tccccatgcc ctggcgccag   4440
tccgagtcgg acattattgc ctccaagatc aagaacggcg ggctcaatat cggctactac   4500
aacttcgacg gcaatgtcct tccacaccct cctatcctgc gcggcgtgga accaccgtc    4560
gccgcactcg ccaaagccgg tcacaccgtg accccgtgga cgccatacaa gcacgatttc   4620
ggccacgatc tcatctccca tatctacgcg gctgacggca gcgccgacgt aatgcgcgat   4680
atcagtgcat ccggcgagcc ggcgattcca aatatcaaag acctactgaa cccgaacatc   4740
aaagctgtta acatgaacga gctctgggac acgcatctcc agaagtggaa ttaccagatg   4800
gagtaccttg agaaatggcg ggaggctgaa gaaaaggccg ggaaggaact ggacgccatc   4860
atcgcgccga ttacgcctac cgctgcggta cggcatgacc agttccggta ctatgggtat   4920
gcctctgtga tcaacctgct ggatttcacg agcgtggttg ttccggttac ctttgcggat   4980
aagaacatcg ataagaagaa tgagagtttc aaggcggtta gtgagcttga tgccctcgtg   5040
caggaagagt atgatccgga ggcgtaccat ggggcaccgg ttgcagtgca ggttatcgga   5100
cggagactca gtgaagagag gacgttggcg attgcagagg aagtggggaa gttgctggga   5160
aatgtggtga ctccatagct aataagtgtc agatagcaat ttgcacaaga aatcaatacc   5220
agcaactgta aataagcgct gaagtgacca tgccatgcta cgaaagagca gaaaaaaacc   5280
tgccgtagaa ccgaagagat atgacacgct tccatctctc aaaggaagaa tcccttcagg   5340
gttgcgtttc cagtctagac acgtataacg gcacaagtgt ctctcaccaa atgggttata   5400
tctcaaatgt gatctaagga tggaaagccc agaatatcga tcgcgcgcag atccatatat   5460
agggcccggg ttataattac ctcaggtcga cgtcccatgg ccattcgaat tcgtaatcat   5520
ggtcatagct gtttcctgtg tgaaattgtt atccgctcac aattccacac aacatacgag   5580
ccggaagcat aaagtgtaaa gcctggggtg cctaatgagt gagctaactc acattaattg   5640
cgttgcgctc actgcccgct ttccagtcgg gaaacctgtc gtgccagctg cattaatgaa   5700
tcggccaacg cgcggggaga ggcggtttgc gtattgggcg ctcttccgct tcctcgctca   5760
ctgactcgct gcgctcggtc gttcggctgc ggcgagcggt atcagctcac tcaaaggcgg   5820
```

```
taatacggtt atccacagaa tcaggggata acgcaggaaa gaacatgtga gcaaaaggcc    5880
agcaaaaggc caggaaccgt aaaaaggccg cgttgctggc gttttttccat aggctccgcc   5940 cccctgacga gcatcacaaa aatcgacgct caagtcagag gtggcgaaac ccgacaggac   6000
tataaagata ccaggcgttt ccccctggaa gctccctcgt gcgctctcct gttccgaccc   6060
tgccgcttac cggatacctg tccgcctttc tcccttcggg aagcgtggcg ctttctcata   6120
gctcacgctg taggtatctc agttcggtgt aggtcgttcg ctccaagctg ggctgtgtgc   6180
acgaaccccc cgttcagccc gaccgctgcg ccttatccgg taactatcgt cttgagtcca   6240
acccggtaag acacgactta tcgccactgg cagcagccac tggtaacagg attagcagag   6300
cgaggtatgt aggcggtgct acagagttct tgaagtggtg gcctaactac ggctacacta   6360
gaagaacagt atttggtatc tgcgctctgc tgaagccagt taccttcgga aaaagagttg   6420
gtagctcttg atccggcaaa caaaccaccg ctggtagcgg tggttttttt gtttgcaagc   6480
agcagattac gcgcagaaaa aaaggatctc aagaagatcc tttgatcttt tctacggggt   6540
ctgacgctca gtggaacgaa aactcacgtt aagggatttt ggtcatgaga ttatcaaaaa   6600
ggatcttcac ctagatcctt ttaaattaaa aatgaagttt taaatcaatc taaagtatat   6660
atgagtaaac ttggtctgac agttaccaat gcttaatcag tgaggcacct atctcagcga   6720
tctgtctatt tcgttcatcc atagttgcct gactccccgt cgtgtagata actacgatac   6780
gggagggctt accatctggc cccagtgctg caatgatacc gcgagaccca cgctcaccgg   6840
ctccagattt atcagcaata aaccagccag ccggaagggc cgagcgcaga agtggtcctg   6900
caactttatc cgcctccatc cagtctatta attgttgccg gaagctaga gtaagtagtt   6960 cgccagttaa tagtttgcgc aacgttgttg ccattgctac aggcatcgtg gtgtcacgct   7020
cgtcgtttgg tatggcttca ttcagctccg gttcccaacg atcaaggcga gttacatgat   7080
cccccatgtt gtgcaaaaaa gcggttagct ccttcggtcc tccgatcgtt gtcagaagta   7140
agttggccgc agtgttatca ctcatggtta tggcagcact gcataattct cttactgtca   7200
tgccatccgt aagatgcttt tctgtgactg gtgagtactc aaccaagtca ttctgagaat   7260
agtgtatgcg gcgaccgagt tgctcttgcc cggcgtcaat acgggataat accgcgccac   7320
atagcagaac tttaaaagtg ctcatcattg gaaaacgttc ttcggggcga aaactctcaa   7380
ggatcttacc gctgttgaga tccagttcga tgtaacccac tcgtgcaccc aactgatctt   7440
cagcatcttt tactttcacc agcgtttctg ggtgagcaaa aacaggaagg caaaatgccg   7500
caaaaaaggg aataagggcg acacggaaat gttgaatact catactcttc cttttttcaat   7560 attattgaag catttatcag ggttattgtc tcatgagcgg atacatattt gaatgtattt   7620
agaaaaataa acaaataggg gttccgcgca catttcccCg aaaagtgcca cctgacgtct   7680
aagaaaccat tattatcatg acattaacct ataaaaatag gcgtatcacg aggccctttc   7740
gtctcgcgcg tttcggtgat gacggtgaaa acctctgaca catgcagctc ccggagacgg   7800
tcacagcttg tctgtaagcg gatgccggga gcagacaagc ccgtcagggc gcgtcagcgg   7860
gtgttggcgg gtgtcgggc tggcttaact atgcggcatc agagcagatt gtactgagag   7920
tgcaccataa aattgtaaac gttaatattt tgttaaaatt cgcgttaaat ttttgttaaa   7980
tcagctcatt ttttaaccaa taggccgaaa tcggcaaaat cccttataaa tcaaaagaat   8040
agcccgagat agggttgagt gttgttccag tttggaacaa gagtccacta ttaaagaacg   8100
tggactccaa cgtcaagggg cgaaaaaccg tctatcaggg cgatggccca ctacgtgaac   8160
catcacccaa atcaagtttt tggggtcga ggtgccgtaa agcactaaat cggaacccta   8220
```

```
aagggagccc ccgatttaga gcttgacggg gaaagccggc gaacgtggcg agaaaggaag    8280
ggaagaaagc gaaggagcg  ggcgctaggg cgctggcaag tgtagcggtc acgctgcgcg    8340
taaccaccac acccgccgcg cttaatgcgc cgctacaggg cgcgtactat ggttgctttg    8400
acgtatgcgg tgtgaaatac cgcacagatg cgtaaggaga aaataccgca tcaggcgcca    8460
ttcgccattc aggctgcgca actgttggga agggcgatcg gtgcgggcct cttcgctatt    8520
acgccagctg gcgaaagggg gatgtgctgc aaggcgatta agttgggtaa cgccagggtt    8580
ttcccagtca cgacgttgta aaacgacggc cagtgc                              8616
```

<210> SEQ ID NO 11
<211> LENGTH: 6
<212> TYPE: PRT
<213> ORGANISM: artificial sequence
<220> FEATURE:
<223> OTHER INFORMATION: synthetic construct

<400> SEQUENCE: 11

```
Ala Gln Ala Ala Gly Lys
1               5
```

<210> SEQ ID NO 12
<211> LENGTH: 1646
<212> TYPE: PRT
<213> ORGANISM: Lactobacillus animalis

<400> SEQUENCE: 12

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
                20                  25                  30

Asp Glu Thr Ser Ser Ser Asn Glu Thr Gln Thr Glu Gln Thr Leu Asn
            35                  40                  45

Thr Asp Glu Ser Thr Asp Thr Thr Thr Asp Val Ser Asn Glu Ala Lys
        50                  55                  60

Ala Thr Glu Ala Gln Leu Thr Thr Gln Asp Ala Asp Met Ala Ser Ser
65                  70                  75                  80

Glu Glu Lys Thr Thr Asn Val Glu Lys Glu Val Thr Thr Ala Glu Thr
                85                  90                  95

Asn Lys Asp Thr Thr Val Lys Asn Val Glu Ser Ser Glu Gln Asn Thr
            100                 105                 110

Thr Thr Val Ala Asp Lys Asn Ala Val Asp Ser Thr Ala Gln Val Asn
        115                 120                 125

Thr Ala Glu Lys Glu Asn Lys Tyr Thr Gln Glu Asn Val Asn Gly Asn
    130                 135                 140

Trp Tyr Leu Lys Asp Glu Gln Gly Asn Tyr Leu Thr Gly Phe Gln Glu
145                 150                 155                 160

Ile Lys Asp Gln Asn Lys Thr Val Tyr Tyr Asn Pro Asp Ser Lys Gln
                165                 170                 175

Met Val Tyr Gly Gln Gln Asn Ile Asn Gly Asn Trp Tyr Leu Phe Asp
            180                 185                 190

Thr Phe Asn Gly Ala Met Gln Thr Gly Leu Gln Tyr Ile Arg Asp Gln
        195                 200                 205

Lys Lys Leu Ala Tyr Tyr Asn Glu Gln Gly Gln Met Gln Tyr Gly Thr
    210                 215                 220

Val Glu Ile Asp Gly Gln Lys Tyr Gln Ala Asp Thr Phe Asn Gly Ala
```

-continued

```
            225                 230                 235                 240

Ile Lys Gly Lys Gly Gln Thr Lys Ile Ala Asp Asn Trp Tyr Leu Phe
                    245                 250                 255

Asn Asn Ala Gly Gln Val Val Asp Gly Trp Gln Trp Ile Asn Asp Gln
                260                 265                 270

Gly Lys Thr Val Tyr Tyr Ser Thr Lys Thr Ala Gln Met Val His Gly
                275                 280                 285

Gln Gln Asn Ile Asn Gly His Trp Tyr Leu Phe Asp Lys Thr Thr Gly
            290                 295                 300

Ala Met Gln Arg Gly Phe Gln Asn Leu Lys Ala Tyr Gly Asp Asp Lys
    305                 310                 315                 320

Thr Val Tyr Tyr Asn Gln Asp Gly Trp Met Leu Tyr Gly Gln Gln Lys
                    325                 330                 335

Ile Asp Asn Lys Trp Tyr Asn Phe Asp Thr Phe Asn Gly Ala Met Lys
                340                 345                 350

Thr Gly Phe Val Lys Ile Pro Glu Gln Asn Lys Thr Val Tyr Tyr Ala
                355                 360                 365

Pro Asn Gly Gln Met Gln Tyr Gly Trp Gln Trp Val Asp Asn Ala Thr
            370                 375                 380

Arg Tyr Phe Asp Thr Phe Asn Gly Ala Met Ala Thr Gly Gln Lys Leu
    385                 390                 395                 400

Ile Thr Gly His Trp Tyr Leu Phe Asp Asn Asn Gly Ala Met Gln Arg
                    405                 410                 415

Gly Phe Gln Asn Leu Lys Asn Tyr Gly Asp Asn Lys Thr Val Tyr Tyr
                420                 425                 430

Asn Gln Asp Gly Trp Met Leu Tyr Gly Trp Gln Trp Val Asn Asn Ala
                435                 440                 445

Thr Arg Tyr Phe Asp Thr Phe Asn Gly Ala Met Thr Thr Gly Gln Lys
            450                 455                 460

Lys Ile Asn Asp His Trp Tyr Leu Phe Asp Lys Asp Gly Ala Met Gln
    465                 470                 475                 480

Arg Gly Ile Gln Tyr Ile Pro Glu Glu Asn Lys Leu Val Tyr Tyr Asn
                    485                 490                 495

Gln Asp Gly Trp Met Leu Tyr Gly Lys Gln Asn Ile Asn Gly Val Asp
                500                 505                 510

His Asn Phe Asn Thr Phe Asn Gly Ala Leu Glu Ala Lys Gly Gln Val
                515                 520                 525

Lys Val Gly Asn Asn Trp Tyr Leu Phe Asn Asn Ser Gly Thr Ile Gln
            530                 535                 540

Thr Gly Phe Gln Asp Leu Lys Ala Tyr Gly Gln Asp Lys Val Val Tyr
    545                 550                 555                 560

Tyr Asp Pro Lys Thr Ala Ala Met Val Tyr Gly Tyr Gln Asn Ile Asp
                    565                 570                 575

Gly Asn Trp Tyr Leu Phe Ser Arg Ala Asn Gly Ser Met Gln Arg Gly
                580                 585                 590

Leu Gln Asn Val Asn Gly Val Asp Leu Leu Phe Asp Glu Lys Thr Gly
                595                 600                 605

Ala Leu Leu Thr Gly Val Gln Asn Ile Lys Gly Asn Asn Tyr Phe Val
            610                 615                 620

Asp Lys Arg Ser Gly Asn Ile Lys Lys Asn Leu Val Val Leu Gly Ala
    625                 630                 635                 640

Asp Asn Lys Trp Met Tyr Phe Asp Ala Lys Thr Gly Lys Gly Thr Asn
                    645                 650                 655
```

-continued

```
Thr Leu Glu Asp Gln Tyr Lys Lys Gly Val Ser Gly Asn Val Glu
            660             665             670

Phe Ile Thr Asn Asn Ala Ala Tyr Ser Phe Asp Gly Asn Ser Phe Glu
            675             680             685

Asn Ile Asn Gly Phe Leu Thr Ala Asp Ser Trp Tyr Arg Pro Lys Ser
            690             695             700

Ile Leu Lys Asp Gly Ser Thr Trp Thr Ala Thr Glu Thr Asp Leu
705             710             715             720

Arg Pro Leu Leu Met Thr Trp Trp Pro Asn Glu Gln Ile Lys Ala Asn
                725             730             735

Tyr Leu Asn Tyr Met Lys Asp Lys Gly Phe Ile Asn Asn Ser Gly Thr
            740             745             750

Tyr Asn Ala Glu Ser Asp Pro Asn Tyr Met Asp Phe Ala Ala Gln Glu
            755             760             765

Ala Gln Arg Asn Ile Glu Arg Lys Ile Thr Lys Glu Asn Asp Thr Thr
            770             775             780

Trp Leu Arg Asp Leu Ile Thr Asp Phe Ile Lys Thr Gln Asp Ile Trp
785             790             795             800

Asn Glu Gln Ser Glu Gly Val Ser Thr Glu Gly Leu Lys Phe Gln
            805             810             815

Gly Gly Phe Leu Lys Tyr Val Asn Ser Glu Leu Thr Pro Tyr Ala Asn
            820             825             830

Ser Glu Trp Arg Lys Leu Gly Tyr Gln Pro Thr Met Leu Thr Gln Asn
            835             840             845

Asn Val Gly Ala Glu Phe Leu Leu Ala Asn Asp Ile Asp Asn Ser Asn
            850             855             860

Pro Val Val Gln Ala Glu Gln Leu Asn Trp Leu His Phe Leu Met Asn
865             870             875             880

Phe Gly Thr Ile Thr Ala Asn Asp Pro Ser Ala Asn Phe Asp Gly Ile
            885             890             895

Arg Ile Asp Ala Val Asp Asn Val Asp Ala Ser Leu Leu Ser Ile Ala
            900             905             910

Gly Asp Tyr Phe Lys Ala Ala Tyr Lys Val Gly Gln Asn Asp Ala Thr
            915             920             925

Ala Asn Lys His Ile Ser Ile Leu Glu Asp Trp Asn Asp Lys Asp Pro
930             935             940

Glu Tyr Val Asn Ser Ile Gly Asn Pro Gln Leu Thr Met Asp Asp Tyr
945             950             955             960

Ile Val Gln Gln Leu Lys Phe Ser Leu Gly Gln Ala Pro Asp Lys Val
            965             970             975

Asp Arg Met Gln Arg Phe Lys Glu Trp Tyr Leu Val Ala Arg Ser Lys
            980             985             990

Asp Asn Thr Glu Asn Thr Ala Ile Pro Asn Tyr Ser Phe Val Arg Ala
            995             1000            1005

His Asp Ala Ser Val Gln Glu Asp Ile Leu Gln Leu Ile Gln Asp
            1010            1015            1020

Thr Thr Gly Lys Pro Trp Gly Val Tyr Thr Asn Glu Glu Leu Gln
            1025            1030            1035

Gln Gly Leu Lys Asp Tyr Met Ala Asp Gln Lys Leu Thr Asn Lys
            1040            1045            1050

Lys Tyr Asn Arg Tyr Asn Ile Pro Ser Ser Tyr Ala Ile Leu Leu
            1055            1060            1065
```

```
Thr Asn Lys Asp Thr Ile Pro Arg Val Tyr Tyr Gly Asp Leu Tyr
1070                1075                1080

Ser Asp Ala Gly Lys Tyr Met Ala Glu Lys Ser Ile Tyr Phe Asp
1085                1090                1095

Ala Ile Asp Asn Leu Leu Lys Thr Arg Thr Lys Tyr Val Ala Gly
1100                1105                1110

Gly Gln Thr Leu Asp Val Asp Gly His Asp Ile Leu Thr Ser Val
1115                1120                1125

Arg Phe Gly Lys Gly Ala Leu Asn Val Thr Asp Lys Gly Thr Ser
1130                1135                1140

Glu Thr Arg Thr Gln Gly Met Gly Leu Ile Ile Ser Asn Asn Asn
1145                1150                1155

Ser Leu Lys Leu Asn Asp Gly Glu Lys Val Val Leu His Met Gly
1160                1165                1170

Ala Ala His Lys Asn Gln Ala Tyr Arg Ala Val Met Leu Ser Ser
1175                1180                1185

Ala Asn Gly Leu Ile Asn Tyr Thr Ser Asp Ala Asn Ala Pro Val
1190                1195                1200

Val Tyr Thr Asn Asn Asp Gly Asp Leu Ile Phe Thr Asn Lys Asp
1205                1210                1215

Val Val Thr Asn Gly Lys Val Gln Ala Asn Thr Ala Ile Lys Gly
1220                1225                1230

Val Met Asn Pro Tyr Val Ser Gly Tyr Leu Ala Met Trp Val Pro
1235                1240                1245

Val Gly Ala Ser Ala Thr Gln Asp Ala Arg Thr Ala Ala Ser Thr
1250                1255                1260

Lys Thr Thr Thr Asp Gly Ser Val Phe His Ser Asn Ala Ala Leu
1265                1270                1275

Asp Ser Asn Leu Ile Tyr Glu Gly Phe Ser Asn Phe Gln Ala Phe
1280                1285                1290

Pro Glu Asn Ala Ser Glu Asn Ala Asn Ala Ile Ile Ala Gln Asn
1295                1300                1305

Val Asp Leu Phe Asn Ser Trp Gly Val Thr Ser Phe Gln Leu Ala
1310                1315                1320

Pro Gln Tyr Val Ser Ser His Asp Gly Ser Phe Leu Asp Ser Ile
1325                1330                1335

Ile Asp Asn Gly Tyr Ala Phe Thr Asp Arg Tyr Asp Leu Ala Met
1340                1345                1350

Ser Lys Asn Asn Lys Tyr Gly Ser Tyr Gln Asp Leu Val Asn Val
1355                1360                1365

Leu Lys Ala Leu His Ala Gly Gly Ile Gln Val Ile Ala Asp Trp
1370                1375                1380

Val Pro Asp Gln Ile Tyr Ser Leu Pro Gly Lys Glu Val Val Ser
1385                1390                1395

Val Val Arg Ser Asp Glu Phe Gly Asn Lys Val Asp Gly Thr Gln
1400                1405                1410

Ile Asp Asn Thr Leu Tyr Val Val Asn Thr Ile Gly Gly Gly Gln
1415                1420                1425

Tyr Gln Lys Glu Tyr Gly Gly Arg Tyr Leu Glu Glu Leu Lys Gln
1430                1435                1440

Lys Tyr Pro Glu Leu Phe Lys Thr Lys Gln Pro Ser Thr Gly Val
1445                1450                1455

Thr Ile Asp Pro Ser Glu Lys Ile Thr Glu Trp Ser Ala Lys Tyr
```

```
                1460                1465                1470
Leu Asn Gly Thr Asn Ile Leu His Arg Gly Ala Glu Phe Val Leu
        1475                1480                1485

Arg Asp Gly Ala Thr Tyr Phe Arg Val Ala Glu Thr Ser Glu Val
    1490                1495                1500

Phe Leu Pro Ser Gln Leu Arg Gly Lys Ile Thr Lys Asn Gly Phe
    1505                1510                1515

Trp Lys Asn Asp Ala Gly Lys Val Asn Tyr Tyr Asn Ser Glu Gly
    1520                1525                1530

Glu Ile Met Lys Asn Ala Phe Val Lys Asp Gly Lys Asn Asn Trp
    1535                1540                1545

Tyr Tyr Phe Asp Asn Asp Gly Asn Met Val Thr Asn Thr Ala Leu
    1550                1555                1560

Thr Ile Asp Ser Asp Ala Gln Val Ala Asp Tyr Tyr Phe Leu Asn
    1565                1570                1575

Asn Gly Ile Ser Leu Arg Asp Gly Phe Val Gln Leu Ala Asn Gly
    1580                1585                1590

Asp Ile Tyr Tyr Tyr Asp Val Asn Gly Arg Lys Leu Lys Asn Gly
    1595                1600                1605

Lys Val Thr Val Asn Asn Val Glu Tyr Thr Thr Asp Lys Asn Gly
    1610                1615                1620

Lys Val Val Gly Glu Asn Val Leu Lys Lys Leu Asp Glu Ile Ile
    1625                1630                1635

Thr Thr Gly Lys Thr Thr Leu Ile
    1640                1645

<210> SEQ ID NO 13
<211> LENGTH: 1587
<212> TYPE: PRT
<213> ORGANISM: Streptococcus salivarius

<400> SEQUENCE: 13

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Ser Ala Glu Glu Thr
            20                  25                  30

Asn Asn Ser Asn Gly Ser Pro Ser Thr Thr Val Gly Glu Asn Thr
        35                  40                  45

Asn Pro Val Val Glu Lys Glu Val Gly Thr Thr Thr Glu Val Ala Asn
    50                  55                  60

Thr Ser Asn Ala Thr Thr Thr Glu Arg Ala Glu Val Thr Ala Asp Lys
65                  70                  75                  80

Pro Ala Glu Thr Thr Val Gln Pro Asn Ser Gly Thr Thr Thr Ser Asp
                85                  90                  95

Arg Ala Val Ala Val Glu Val Glu Ala Lys Pro Glu Thr Thr Ala Lys
            100                 105                 110

Pro Glu Val Ala Thr Lys Pro Glu Thr Ala Thr Thr Ser Glu Val Ala
        115                 120                 125

Ala Asn Ala Gly Val Ala Ala Pro Thr Thr Glu Lys Ser Lys Glu Leu
    130                 135                 140

Ser Glu Ala Glu Ile Lys Ala Ala Val Ser Leu Asp Asn Ile Lys Lys
145                 150                 155                 160

Glu Lys Asp Gly Lys Tyr Tyr Tyr Leu Leu Glu Asp Gly Ser His Lys
                165                 170                 175
```

-continued

Lys Asn Phe Ala Ile Thr Val Asn Gly Gln Val Leu Tyr Phe Asp Glu
                180                 185                 190

Asn Gly Ala Leu Ser Ser Thr Tyr Ser Phe Thr Gln Glu Thr
            195                 200                 205

Thr Asn Leu Val Thr Asp Phe Thr Lys Asn Asn Ala Ala Tyr Asp Ser
            210                 215                 220

Thr Lys Ala Ser Phe Glu Leu Val Asp Gly Tyr Leu Thr Ala Asp Ser
225                 230                 235                 240

Trp Tyr Arg Pro Lys Glu Ile Leu Glu Ala Gly Thr Thr Trp Lys Ala
                245                 250                 255

Ser Thr Glu Lys Asp Phe Arg Pro Leu Leu Met Ser Trp Trp Pro Asp
                260                 265                 270

Lys Asp Thr Gln Val Ala Tyr Leu Asn Tyr Met Thr Lys Ala Leu Ser
                275                 280                 285

Asn Gly Glu Glu Thr Lys Asp Val Phe Thr Ile Glu Asn Ser Gln Ala
            290                 295                 300

Ser Leu Asn Ala Ala Gln Ile Leu Gln Arg Lys Ile Glu Val Lys
305                 310                 315                 320

Ile Ala Ala Asn Lys Ser Thr Asp Trp Leu Arg Gln Ser Ile Glu Ala
                325                 330                 335

Phe Val Lys Asp Gln Asp Lys Trp Asn Ile Asn Ser Glu Ser Pro Gly
                340                 345                 350

Lys Glu His Phe Gln Lys Gly Ala Leu Leu Phe Val Asn Ser Asp Ser
                355                 360                 365

Thr Lys Trp Ala Asn Ser Asp Tyr Arg Lys Leu Asn Gln Thr Ala Thr
                370                 375                 380

Ser Tyr Ile Lys Asn His Lys Ile Val Asn Gly Ser Asp Gly Gly Tyr
385                 390                 395                 400

Glu Phe Leu Leu Ser Asn Asp Ile Asp Asn Ser Asn Pro Val Val Gln
                405                 410                 415

Ala Glu Met Leu Asn Gln Leu Tyr Tyr Phe Met Asn Trp Gly Gln Ile
                420                 425                 430

Val Phe Gly Asp Lys Asp Lys Asp Ala His Phe Asp Gly Ile Arg Val
                435                 440                 445

Asp Ala Val Asp Asn Val Ser Val Asp Met Leu Gln Leu Val Ser Ser
450                 455                 460

Tyr Met Lys Ala Ala Tyr Lys Val Asn Glu Ser Glu Ala Arg Ala Leu
465                 470                 475                 480

Ala Asn Ile Ser Ile Leu Glu Ala Trp Ser His Asn Asp Pro Tyr Tyr
                485                 490                 495

Val Asn Glu His Asn Thr Ala Ala Leu Ser Met Asp Asn Gly Leu Arg
                500                 505                 510

Leu Ser Ile Val His Gly Leu Thr Arg Pro Val Thr Asn Lys Gly Thr
                515                 520                 525

Gly Ala Arg Asn Ala Ser Met Lys Asp Leu Ile Asn Gly Gly Tyr Phe
                530                 535                 540

Gly Leu Ser Asn Arg Ala Glu Val Thr Ser Tyr Asp Gln Leu Gly Phe
545                 550                 555                 560

Ala Thr Tyr Leu Phe Val Arg Ala His Asp Ser Glu Val Gln Thr Val
                565                 570                 575

Ile Ala Asp Ile Ile Ser Lys Lys Ile Asp Pro Thr Thr Asp Gly Phe
                580                 585                 590

Thr Phe Thr Leu Asp Gln Leu Lys Gln Ala Phe Asp Ile Tyr Asn Ala

```
                595                 600                 605
Asp Met Leu Lys Val Asp Lys Glu Tyr Thr His Ser Asn Ile Pro Ala
    610                 615                 620
Ala Tyr Ala Leu Met Leu Gln Thr Met Gly Ala Ala Thr Arg Val Tyr
625                 630                 635                 640
Tyr Gly Asp Leu Tyr Thr Asp Asn Gly Gln Tyr Met Ala Lys Lys Ser
                645                 650                 655
Pro Tyr Phe Asp Gln Ile Thr Thr Leu Leu Lys Ala Arg Pro Lys Tyr
                660                 665                 670
Val Ala Gly Gly Gln Thr Ser Tyr Ile His Asn Leu Ala Gly Asp Gly
                675                 680                 685
Val Ser Ser Ala Lys Asp Asn Lys Glu Val Leu Val Ser Val Arg Tyr
            690                 695                 700
Gly Gln Asp Leu Met Ser Lys Thr Asp Thr Glu Gly Lys Tyr Gly
705                 710                 715                 720
Arg Asn Ser Gly Met Leu Thr Leu Ile Ala Asn Asn Pro Asp Leu Lys
                725                 730                 735
Leu Ala Asp Gly Glu Thr Ile Thr Val Asn Met Gly Ala Ala His Lys
                740                 745                 750
Asn Gln Ala Tyr Arg Pro Leu Leu Leu Gly Thr Asp Lys Gly Ile Val
            755                 760                 765
Ser Ser Leu Asn Asp Ser Asp Thr Lys Val Val Lys Tyr Thr Asp Ala
770                 775                 780
Gln Gly Asn Leu Val Phe Thr Ala Asp Glu Ile Lys Gly Phe Lys Thr
785                 790                 795                 800
Val Asp Met Ser Gly Tyr Leu Ser Val Trp Val Pro Val Gly Ala Thr
                805                 810                 815
Asp Asp Gln Asn Val Leu Ala Lys Pro Ser Thr Lys Ala Tyr Lys Glu
                820                 825                 830
Gly Asp Lys Val Tyr Ser Ser Ala Ala Leu Glu Ala Gln Val Ile
            835                 840                 845
Tyr Glu Gly Phe Ser Asn Phe Gln Asp Phe Val Lys Glu Asp Ser Gln
850                 855                 860
Tyr Thr Asn Lys Leu Ile Ala Ala Asn Ala Asp Leu Phe Lys Ser Trp
865                 870                 875                 880
Gly Ile Thr Ser Phe Glu Ile Ala Pro Gln Tyr Val Ser Ser Lys Asp
                885                 890                 895
Gly Thr Phe Leu Asp Ser Ile Ile Glu Asn Gly Tyr Ala Phe Thr Asp
                900                 905                 910
Arg Tyr Asp Phe Ala Met Ser Lys Asn Asn Lys Tyr Gly Ser Lys Glu
            915                 920                 925
Asp Leu Arg Asp Ala Leu Lys Ala Leu His Lys Gly Ile Gln Val
            930                 935                 940
Ile Ala Asp Trp Val Pro Asp Gln Leu Tyr Thr Leu Pro Gly Lys Glu
945                 950                 955                 960
Val Val Thr Ala Thr Arg Thr Asp Thr His Gly Lys Val Leu Asp Asp
                965                 970                 975
Thr Ser Leu Val Asn Lys Leu Tyr Val Thr Thr Lys Ser Ser Gly
            980                 985                 990
Asn Asp Phe Gln Ala Gln Tyr Gly  Gly Ala Phe Leu Asp Lys Leu Gln
            995                 1000                1005
Lys Leu Tyr Pro Glu Ile Phe Lys Glu Val Met Glu Ala Ser Gly
        1010                1015                1020
```

```
Lys Thr Ile Asp Pro Ser Val Lys Ile Lys Gln Trp Glu Ala Lys
1025                1030                1035

Tyr Phe Asn Gly Thr Asn Ile Gln Lys Arg Gly Ser Asp Tyr Val
1040                1045                1050

Leu Ser Asp Gly Lys Leu Tyr Phe Thr Val Asn Asp Lys Gly Thr
1055                1060                1065

Phe Leu Pro Ala Ala Leu Thr Gly Asp Thr Lys Ala Lys Thr Gly
1070                1075                1080

Phe Ala Tyr Asp Gly Thr Gly Val Thr Tyr Tyr Thr Thr Ser Gly
1085                1090                1095

Thr Gln Ala Lys Ser Gln Phe Val Thr Tyr Asn Gly Lys Gln Tyr
1100                1105                1110

Tyr Phe Asn Asp Lys Gly Tyr Leu Val Thr Gly Glu Gln Thr Ile
1115                1120                1125

Asp Gly Ser Asn Tyr Phe Phe Leu Pro Asn Gly Val Met Phe Thr
1130                1135                1140

Asp Gly Val Arg Lys Asn Ala Lys Gly Gln Ser Leu Val Tyr Gly
1145                1150                1155

Lys Ser Gly Lys Leu Thr Thr Gln Thr Gly Trp Lys Glu Val Thr
1160                1165                1170

Val Lys Asp Asp Ser Gly Lys Glu Glu Lys Phe Tyr Gln Tyr Phe
1175                1180                1185

Phe Lys Gly Gly Ile Met Ala Thr Gly Leu Thr Glu Val Glu Gly
1190                1195                1200

Lys Glu Lys Tyr Phe Tyr Asp Asn Gly Tyr Gln Ala Lys Gly Val
1205                1210                1215

Phe Val Pro Thr Lys Asp Gly His Leu Met Phe Phe Cys Gly Asp
1220                1225                1230

Ser Gly Glu Arg Lys Tyr Ser Gly Phe Phe Glu Gln Asp Gly Asn
1235                1240                1245

Trp Tyr Tyr Ala Asn Asp Lys Gly Tyr Val Ala Thr Gly Phe Thr
1250                1255                1260

Lys Val Gly Lys Gln Asn Leu Tyr Phe Asn Glu Lys Gly Val Gln
1265                1270                1275

Val Lys Asn Arg Phe Phe Gln Val Gly Asp Ala Thr Tyr Tyr Ala
1280                1285                1290

Asn Asn Glu Gly Asp Val Leu Arg Gly Ala Gln Thr Ile Asn Gly
1295                1300                1305

Asp Glu Leu Tyr Phe Asp Glu Ser Gly Lys Gln Val Lys Gly Glu
1310                1315                1320

Phe Val Asn Asn Pro Asp Gly Thr Thr Ser Tyr Tyr Asp Ala Ile
1325                1330                1335

Thr Gly Val Lys Leu Val Asp Thr Ser Leu Val Val Asp Gly Gln
1340                1345                1350

Thr Phe Asn Val Asp Ala Lys Gly Val Val Thr Lys Ala His Thr
1355                1360                1365

Pro Gly Phe Tyr Thr Thr Gly Asp Asn Asn Trp Phe Tyr Ala Asp
1370                1375                1380

Ser Tyr Gly Arg Asn Val Thr Gly Ala Gln Val Ile Asn Gly Gln
1385                1390                1395

His Leu Tyr Phe Asp Ala Asn Gly Arg Gln Val Lys Gly Gly Phe
1400                1405                1410
```

```
Val Thr Asn Thr Asp Gly Ser Arg Ser Phe Tyr His Trp Asn Thr
    1415            1420                1425

Gly Asp Lys Leu Val Ser Thr Phe Phe Thr Thr Gly His Asp Arg
    1430            1435                1440

Trp Tyr Tyr Ala Asp Asp Arg Gly Asn Val Val Thr Gly Ala Gln
    1445            1450                1455

Val Ile Asn Gly Gln Lys Leu Phe Phe Asp Thr Asp Gly Lys Gln
    1460            1465                1470

Val Lys Gly Ala Phe Ala Thr Asn Ala Asn Gly Ser Arg Ser Tyr
    1475            1480                1485

Tyr His Trp Asn Thr Gly Asn Lys Leu Val Ser Thr Phe Phe Thr
    1490            1495                1500

Ser Gly Asp Asn Asn Trp Tyr Tyr Ala Asp Ala Lys Gly Glu Val
    1505            1510                1515

Val Val Gly Glu Gln Thr Ile Asn Gly Gln His Leu Tyr Phe Asp
    1520            1525                1530

Gln Thr Gly Lys Gln Val Lys Gly Ala Thr Ala Thr Asn Pro Asp
    1535            1540                1545

Gly Ser Ile Ser Tyr Tyr Asp Val His Thr Gly Glu Lys Ala Ile
    1550            1555                1560

Asn Arg Trp Val Lys Ile Pro Ser Gly Gln Trp Val Tyr Phe Asn
    1565            1570                1575

Ala Gln Gly Lys Gly Tyr Val Ser Asn
    1580            1585
```

ENZYMATIC SYNTHESIS OF SOLUBLE GLUCAN FIBER

CROSS-REFERENCE TO RELATED APPLICATIONS

This application claims priority to and the benefit of U.S. provisional application No. 62/004,314, titled "Enzymatic Synthesis of Soluble Glucan Fiber," filed May 29, 2014, the disclosure of which is incorporated by reference herein in its entirety.

INCORPORATION BY REFERENCE OF THE SEQUENCE LISTING

The sequence listing provided in the file named "20150515_CL6239WOPCT_SequenceListing_ST25.txt" with a size of 109,502 bytes which was created on May 14, 2015 and which is filed herewith, is incorporated by reference herein in its entirety.

FIELD OF THE INVENTION

This disclosure relates to a soluble α-glucan fiber, compositions comprising the soluble fiber, and methods of making and using the soluble α-glucan fiber. The soluble α-glucan fiber is highly resistant to digestion in the upper gastrointestinal tract, exhibits an acceptable rate of gas production in the lower gastrointestinal tract, is well tolerated as a dietary fiber, and has one or more beneficial properties typically associated with a soluble dietary fiber.

BACKGROUND OF THE INVENTION

Dietary fiber (both soluble and insoluble) is a nutrient important for health, digestion, and preventing conditions such as heart disease, diabetes, obesity, diverticulitis, and constipation. However, most humans do not consume the daily recommended intake of dietary fiber. The 2010 Dietary Fiber Guidelines for Americans (U.S. Department of Agriculture and U.S. Department of Health and Human Services. *Dietary Guidelines for Americans*, 2010. 7th Edition, Washington, D.C.: U.S. Government Printing Office, December 2010) reports that the insufficiency of dietary fiber intake is a public health concern for both adults and children. As such, there remains a need to increase the amount of daily dietary fiber intake, especially soluble dietary fiber suitable for use in a variety of food applications.

Historically, dietary fiber was defined as the non-digestible carbohydrates and lignin that are intrinsic and intact in plants. This definition has been expanded to include carbohydrate polymers with three or more monomeric units that are not significantly hydrolyzed by the endogenous enzymes in the upper gastrointestinal tract of humans and which have a beneficial physiological effect demonstrated by generally accepted scientific evidence. Soluble oligosaccharide fiber products (such as oligomers of fructans, glucans, etc.) are currently used in a variety of food applications. However, many of the commercially available soluble fibers have undesirable properties such as low tolerance (causing undesirable effects such as abdominal bloating or gas, diarrhea, etc.), lack of digestion resistance, instability at low pH (e.g., pH 4 or less), high cost or a production process that requires at least one acid-catalyzed heat treatment step to randomly rearrange the more-digestible glycosidic bonds (for example, α-(1,4) linkages in glucans) into more highly-branched compounds with linkages that are more digestion-resistant. A process that uses only naturally occurring enzymes to synthesize suitable glucan fibers from a safe and readily-available substrate, such as sucrose, may be more attractive to consumers.

Various bacterial species have the ability to synthesize dextran oligomers from sucrose. Jeanes et al. (*JACS* (1954) 76:5041-5052) describe dextrans produced from 96 strains of bacteria. The dextrans were reported to contain a significant percentage (50-97%) of α-(1,6) glycosidic linkages with varying amounts of α-(1,3) and α-(1,4) glycosidic linkages. The enzymes present (both number and type) within the individual strains were not reported, and the dextran profiles in certain strains exhibited variability, where the dextrans produced by each bacterial species may be the product of more than one enzyme produced by each bacterial species.

Glucosyltransferases (glucansucrases; GTFs) belonging to glucoside hydrolase family 70 are able to polymerize the D-glucosyl units of sucrose to form homooligosaccharides or homopolysaccharides. Glucansucrases are further classified by the type of saccharide oligomer formed. For example, dextransucrases are those that produce saccharide oligomers with predominantly α-(1,6) glycosidic linkages ("dextrans"), and mutansucrases are those that tend to produce insoluble saccharide oligomers with a backbone rich in α-(1,3) glycosidic linkages. Mutansucrases are characterized by common amino acids. For example, A. Shimamura et al. (*J. Bacteriology*, (1994) 176:4845-4850) investigated the structure-function relationship of GTFs from *Streptococcus mutans* GS5, and identified several amino acid positions which influence the nature of the glucan product synthesized by GTFs where changes in the relative amounts of α-(1,3)- and α-(1,6)-anomeric linkages were produced. Reuteransucrases tend to produce saccharide oligomers rich in α-(1,4), α-(1,6), and α-(1,4,6) glycosidic linkages, and alternansucrases are those that tend to produce saccharide oligomers with a linear backbone comprised of alternating α-(1,3) and α-(1,6) glycosidic linkages. Some of these enzymes are capable of introducing other glycosidic linkages, often as branch points, to varying degrees. V. Monchois et al. (*FEMS Microbiol Rev.*, (1999) 23:131-151) discusses the proposed mechanism of action and structure-function relationships for several glucansucrases. H. Leemhuis et al. (*J. Biotechnol.*, (2013) 163:250-272) describe characteristic three-dimensional structures, reactions, mechanisms, and α-glucan analyses of glucansucrases.

A non-limiting list of patents and published patent applications describing the use of glucansucrases (wild type, truncated or variants thereof) to produce saccharide oligomers has been reported for dextran (U.S. Pat. Nos. 4,649,058 and 7,897,373; and U.S. Patent Appl. Pub. No. 2011-0178289A1), reuteran (U.S. Patent Application Publication No. 2009-0297663A1 and U.S. Pat. No. 6,867,026), alternan and/or maltoalternan oligomers ("MAOs") (U.S. Pat. Nos. 7,402,420 and 7,524,645; U.S. Patent Appl. Pub. No. 2010-0122378A1; and European Patent EP1151085B1), α-(1,2) branched dextrans (U.S. Pat. No. 7,439,049), and a mixed-linkage saccharide oligomer (lacking an alternan-like backbone) comprising a mix of α-(1,3), α-(1,6), and α-(1,3,6) linkages (U.S. Patent Appl. Pub. No. 2005-0059633A1). U.S. Patent Appl. Pub. No. 2009-0300798A1 to Kol-Jakon et al. discloses genetically modified plant cells expressing a mutansucrase to produce modified starch.

Enzymatic production of isomaltose, isomaltooligosaccharides, and dextran using a combination of a glucosyltransferase and an α-glucanohydrolase has been reported.

U.S. Pat. No. 2,776,925 describes a method for enzymatic production of dextran of intermediate molecular weight comprising the simultaneous action of dextransucrase and dextranase. U.S. Pat. No. 4,861,381A describes a method to enzymatically produce a composition comprising 39-80% isomaltose using a combination of a dextransucrase and a dextranase. Goulas et al. (*Enz. Microb. Tech* (2004) 35:327-338 describes batch synthesis of isomaltooligosaccharides (IMOs) from sucrose using a dextransucrase and a dextranase. U.S. Pat. No. 8,192,956 discloses a method to enzymatically produce isomaltooligosaccharides (IMOs) and low molecular weight dextran for clinical use using a recombinantly expressed hybrid gene comprising a gene encoding an α-glucanase and a gene encoding dextransucrase fused together; wherein the glucanase gene is a gene from *Arthrobacter* sp., wherein the dextransucrase gene is a gene from *Leuconostoc* sp.

Hayacibara et al. (*Carb. Res.* (2004) 339:2127-2137) describes the influence of mutanase and dextranase on the production and structure of glucans formed by glucosyltransferases from sucrose within dental plaque. The reported purpose of the study was to evaluate the production and the structure of glucans synthesized by GTFs in the presence of mutanase and dextranase, alone or in combination, in an attempt to elucidate some of the interactions that may occur during the formation of dental plaque.

Mutanases (glucan endo-1,3-α-glucanohydrolases) are produced by some fungi, including *Trichoderma*, *Aspergillus*, *Penicillium*, and *Cladosporium*, and by some bacteria, including *Streptomyces*, *Flavobacterium*, *Bacteroides*, *Bacillus*, and *Paenibacillus*. W. Suyotha et al., (*Biosci, Biotechnol. Biochem.*, (2013) 77:639-647) describe the domain structure and impact of domain deletions on the activity of an α-1,3-glucanohydrolases from *Bacillus circulans* KA-304. Y. Hakamada et al. (*Biochimie*, (2008) 90:525-533) describe the domain structure analysis of several mutanases, and a phylogenetic tree for mutanases is presented. I. Shimotsuura et al, (*Appl. Environ. Microbiol.*, (2008) 74:2759-2765) report the biochemical and molecular characterization of mutanase from *Paenibacillus* sp. Strain RM1, where the N-terminal domain had strong mutan-binding activity but no mutanase activity, whereas the C-terminal domain was responsible for mutanase activity but had mutan-binding activity significantly lower than that of the intact protein. C. C. Fuglsang et al. (*J. Biol. Chem.*, (2000) 275:2009-2018) describe the biochemical analysis of recombinant fungal mutanases (endoglucanases), where the fungal mutanases are comprised of a $NH_2$-terminal catalytic domain and a putative COOH-terminal polysaccharide binding domain.

Dextranases (α-1,6-glucan-6-glucanohydrolases) are enzymes that hydrolyzes α-1,6-linkages of dextran. N. Suzuki et al. (*J. Biol. Chem*, (2012) 287: 19916-19926) describes the crystal structure of *Streptococcus mutans* dextranase and identifies three structural domains, including domain A that contains the enzyme's catalytic module, and a dextran-binding domain C; the catalytic mechanism was also described relative to the enzyme structure. A. M. Larsson et al. (*Structure*, (2003) 11:1111-1121) reports the crystal structure of dextranase from *Penicillium minioluteum*, where the structure is used to define the reaction mechanism. H-K Kang et al. (*Yeast*, (2005) 22:1239-1248) describes the characterization of a dextranase from *Lipomyces starkeyi*. T. Igarashi et al. (*Microbiol. Immunol.*, (2004) 48:155-162) describe the molecular characterization of dextranase from *Streptococcus rattus*, where the conserved region of the amino acid sequence contained two functional domains, catalytic and dextran-binding sites.

Various saccharide oligomer compositions have been reported in the art. For example, U.S. Pat. No. 6,486,314 discloses an α-glucan comprising at least 20, up to about 100,000 α-anhydroglucose units, 38-48% of which are 4-linked anhydroglucose units, 17-28% are 6-linked anhydroglucose units, and 7-20% are 4,6-linked anhydroglucose units and/or gluco-oligosaccharides containing at least two 4-linked anhydroglucose units, at least one 6-linked anhydroglucose unit and at least one 4,6-linked anhydroglucose unit. U.S. Patent Appl. Pub. No. 2010-0284972A1 discloses a composition for improving the health of a subject comprising an α-(1,2)-branched α-(1,6) oligodextran. U.S. Patent Appl. Pub. No. 2011-0020496A1 discloses a branched dextrin having a structure wherein glucose or isomaltooligosaccharide is linked to a non-reducing terminal of a dextrin through an α-(1,6) glycosidic bond and having a DE of 10 to 52. U.S. Pat. No. 6,630,586 discloses a branched maltodextrin composition comprising 22-35% (1,6) glycosidic linkages; a reducing sugars content of <20%; a polymolecularity index (Mp/Mn) of <5; and number average molecular weight (Mn) of 4500 g/mol or less. U.S. Pat. No. 7,612,198 discloses soluble, highly branched glucose polymers, having a reducing sugar content of less than 1%, a level of α-(1,6) glycosidic bonds of between 13 and 17% and a molecular weight having a value of between $0.9 \times 10^5$ and $1.5 \times 10^5$ daltons, wherein the soluble highly branched glucose polymers have a branched chain length distribution profile of 70 to 85% of a degree of polymerization (DP) of less than 15, of 10 to 14% of DP of between 15 and 25 and of 8 to 13% of DP greater than 25.

Saccharide oligomers and/or carbohydrate compositions comprising the oligomers have been described as suitable for use as a source of soluble fiber in food applications (U.S. Pat. No. 8,057,840 and U.S. Patent Appl. Pub. Nos. 2010-0047432A1 and 2011-0081474A1). U.S. Patent Appl. Pub. No. 2012-0034366A1 discloses low sugar, fiber-containing carbohydrate compositions which are reported to be suitable for use as substitutes for traditional corn syrups, high fructose corn syrups, and other sweeteners in food products.

There remains a need to develop new soluble α-glucan fiber compositions that are digestion resistant, exhibit a relatively low level and/or slow rate of gas formation in the lower gastrointestinal tract, are well-tolerated, have low viscosity, and are suitable for use in foods and other applications. Preferably the α-glucan fiber compositions can be enzymatically produced from sucrose using enzymes already associated with safe use in humans.

SUMMARY OF THE INVENTION

An α-glucan soluble fiber composition is provided that is suitable for use in a variety of applications including, but not limited to, food applications, compositions to improve gastrointestinal health, and personal care compositions. The soluble fiber composition may be directly used as an ingredient in food or may be incorporated into carbohydrate compositions suitable for use in food applications.

A process for producing the soluble glucan fiber composition is provided. Methods of using the soluble fiber composition or carbohydrate compositions comprising the soluble fiber composition in food applications are also provided. In certain aspects, methods are provided for improving the health of a subject comprising administering the present soluble fiber composition to a subject in an amount effective to exert at least one health benefit typically associated with soluble dietary fiber such as altering the caloric content of food, decreasing the glycemic index of food, altering fecal weight and supporting bowel function, altering cholesterol metabolism, provide energy-yielding metabolites through colonic fermentation, and possibly providing prebiotic effects.

A soluble fiber composition is provided comprising on a dry solids basis the following:
a. at least 95% α-(1,6) glycosidic linkages;
b. 1% or less α-(1,3) glycosidic linkages;
c. less than 2% α-(1,3,6) glycosidic linkages;
d. less than 1.5% α-(1,4) glycosidic linkages;
e. a weight average molecular weight of less than 20000 Daltons;
f. a viscosity of less than 0.25 Pascal second (Pa·s) at 12 wt % in water at 20° C.;
g. a dextrose equivalence (DE) in the range of 1 to 30;
h. a digestibility of less than 10% as measured by the Association of Analytical Communities (AOAC) method 2009.01;
i. a solubility of at least 20% (w/w) in pH 7 water at 25° C.; and
j. a polydispersity index of less than 5.

In another embodiment, a carbohydrate composition is provided comprising: 0.01 to 99 wt % (dry solids basis) of the present soluble α-glucan fiber composition.

In another embodiment, a food product, cosmetic composition or pharmaceutical composition is provided comprising the present soluble α-glucan fiber composition or a carbohydrate composition comprising the present soluble α-glucan fiber composition.

In another embodiment, a method is provided to produce a soluble α-glucan fiber composition comprising:
a. providing a set of reaction components comprising:
  i. sucrose;
  ii. at least one polypeptide having glucosyltransferase activity, said polypeptide comprising an amino acid sequence having at least 90% identity to SEQ ID NO: 1, 3, 4 or 6;
  iii. optionally one or more acceptors;
b. combining the set of reaction components under suitable aqueous reaction conditions whereby a product comprising a soluble α-glucan fiber composition is produced; and
c. optionally isolating the soluble α-glucan fiber composition from the product of step (b).

In another embodiment, a method is provided to make a blended carbohydrate composition comprising combining the present soluble α-glucan fiber composition with: a monosaccharide, a disaccharide, glucose, sucrose, fructose, leucrose, corn syrup, high fructose corn syrup, isomerized sugar, maltose, trehalose, panose, raffinose, cellobiose, isomaltose, honey, maple sugar, a fruit-derived sweetener, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, a resistant maltodextrin, a branched maltodextrin, inulin, polydextrose, a fructooligosaccharide, a galactooligosaccharide, an isomaltooligosaccharide, a xylooligosaccharide, an arabinoxylooligosaccharide, a nigerooligosaccharide, a gentiooligosaccharide, a filler, an excipient, a binder or any combination thereof.

In another embodiment, a method is provided to make a food product comprising mixing one or more edible food ingredients with the present soluble α-glucan fiber composition or the carbohydrate composition comprising the present soluble α-glucan fiber composition, or a combination thereof.

In another embodiment, a method is provided to reduce the glycemic index of a food or beverage comprising incorporating into the food or beverage the present soluble α-glucan fiber composition.

In another embodiment, a method is provided for inhibiting the elevation of blood-sugar level in a mammal comprising a step of administering the present soluble α-glucan fiber composition to the mammal.

In another embodiment, a method is provided for lowering lipids in the living body of a mammal comprising a step of administering the present soluble α-glucan fiber composition to the mammal.

In another embodiment, a method is provided for treating constipation in a mammal comprising a step of administering the present soluble α-glucan fiber composition to the mammal.

In another embodiment, a method to alter fatty acid production in the colon of a mammal is provided, the method comprising a step of administering the present soluble α-glucan fiber composition to the mammal; preferably wherein the short chain fatty acid production is increased and/or the branched chain fatty acid production is decreased.

In another embodiment, a low cariogenicity composition is provided comprising the present soluble α-glucan fiber composition and at least one polyol.

In another embodiment, a composition is provided comprising 0.01 to 99 wt % (dry solids basis) of the present soluble α-glucan fiber composition and: a synbiotic, a peptide, a peptide hydrolysate, a protein, a protein hydrolysate, a soy protein, a dairy protein, an amino acid, a polyol, a polyphenol, a vitamin, a mineral, an herbal, an herbal extract, a fatty acid, a polyunsaturated fatty acid (PUFAs), a phytosteroid, betaine, a carotenoid, a digestive enzyme, a probiotic organism or any combination thereof.

In another embodiment, a product produced by any of the methods described herein is also provided; preferably wherein the product is the present soluble α-glucan fiber composition.

BRIEF DESCRIPTION OF THE BIOLOGICAL SEQUENCES

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO: 1 is the amino acid sequence of the *Lactobacillus animalis* KCTC 3501 glucosyltransferase as provided in GENBANK® gi:335358117; which may be referred to herein as "GTF8117".

SEQ ID NO: 2 is the polynucleotide sequence encoding the *Bacillus subtilis* AprE signal peptide coupled through a peptide linker to the mature form of the *Lactobacillus animalis* KCTC 3501 glucosyltransferase (GENBANK® gi:335358117).

SEQ ID NO: 3 is the amino acid sequence of the mature *Lactobacillus animalis* KCTC 3501 glucosyltransferase (GENBANK® gi:335358117); which is also referred to herein as the "8117" glucosyltransferase or "GTF8117".

SEQ ID NO: 4 is the amino acid sequence of the *Streptococcus salivarius* M18 glucosyltransferase as provided in GENBANK® gi:345526831; which may also be referred to herein as "GTF6831".

SEQ ID NO: 5 is the polynucleotide sequence encoding the *Streptococcus salivarius* glucosyltransferase (GENBANK® gi:345526831).

SEQ ID NO: 6 is the amino acid sequence of the mature *Streptococcus salivarious* M18 3501 glucosyltransferase which is also referred to herein as the "6831" glucosyltransferase or "GTF6831".

SEQ ID NO: 7 is the amino acid sequence of the *B. subtilis* AprE signal peptide used in the expression vector that was coupled to various enzymes for expression in *B. subtilis*.

SEQ ID NO: 8 is a polynucleotide sequence of a terminator sequence.

SEQ ID NO: 9 is a polynucleotide sequence of a linker sequence.

SEQ ID NO: 10 is the polynucleotide sequence of plasmid pTrex3.

SEQ ID NO: 11 is the amino acid sequence used as a peptide linker.

SEQ ID NO: 12 is the amino acid sequence of the *Bacillus subtilis* AprE signal peptide coupled through a peptide linker (SEQ ID NO: 11) to the mature form of the *Lactobacillus animalis* glucosyltransferase.

SEQ ID NO: 13 is the amino acid sequence of the *Bacillus subtilis* AprE signal peptide coupled to the mature *Streptococcus salivarius* glucosyltransferase.

DETAILED DESCRIPTION OF THE INVENTION

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "obtainable from" shall mean that the source material (for example, sucrose) is capable of being obtained from a specified source, but is not necessarily limited to that specified source.

As used herein, the term "effective amount" will refer to the amount of the substance used or administered that is suitable to achieve the desired effect. The effective amount of material may vary depending upon the application. One of skill in the art will typically be able to determine an effective amount for a particular application or subject without undo experimentation.

As used herein, the term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated.

As used herein, the terms "very slow to no digestibility", "little or no digestibility", and "low to no digestibility" will refer to the relative level of digestibility of the soluble glucan fiber as measured by the Association of Official Analytical Chemists International (AOAC) method 2009.01 ("AOAC 2009.01"; McCleary et al. (2010) *J. AOAC Int.*, 93(1), 221-233); where little or no digestibility will mean less than 12% of the soluble glucan fiber composition is digestible, preferably less than 5% digestible, more preferably less than 1% digestible on a dry solids basis (d.s.b.). In another aspect, the relative level of digestibility may be alternatively be determined using AOAC 2011.25 (Integrated Total Dietary Fiber Assay) (McCleary et al., (2012) *J. AOAC Int.*, 95 (3), 824-844.

As used herein, term "water soluble" will refer to the present glucan fiber composition comprised of fibers that are soluble at 20 wt % or higher in pH 7 water at 25° C.

As used herein, the terms "soluble fiber", "soluble glucan fiber", "α-glucan fiber", "cane sugar fiber", "glucose fiber", "beet sugar fiber", "soluble dietary fiber", and "soluble glucan fiber composition" refer to the present fiber composition comprised of water soluble glucose oligomers having a glucose polymerization degree of 3 or more that is digestion resistant (i.e., exhibits very slow to no digestibility) with little or no absorption in the human small intestine and is at least partially fermentable in the lower gasterointestinal tract. Digestibility of the soluble glucan fiber composition is measured using AOAC method 2009.01. The present soluble glucan fiber composition is enzymatically synthesized from sucrose (α-D-Glucopyranosyl β-D-fructofuranoside; CAS #57-50-1) obtainable from, for example, sugarcane and/or sugar beets. In one embodiment, the present soluble α-glucan fiber composition is not alternan or maltoalternan oligosaccharide.

As used herein, "weight average molecular weight" or "$M_w$" is calculated as $M_w = \Sigma N_i M_i^2 / \Sigma N_i M_i$; where $M_i$ is the molecular weight of a chain and $N_i$ is the number of chains of that molecular weight. The weight average molecular weight can be determined by technics such as static light scattering, small angle neutron scattering, X-ray scattering, and sedimentation velocity.

As used herein, "number average molecular weight" or "$M_n$" refers to the statistical average molecular weight of all the polymer chains in a sample. The number average molecular weight is calculated as $M_n = \Sigma N_i M_i / \Sigma N_1$ where $M_i$ is the molecular weight of a chain and $M_i$ is the number of chains of that molecular weight. The number average molecular weight of a polymer can be determined by technics such as gel permeation chromatography, viscometry via the (Mark-Houwink equation), and colligative methods such as vapor pressure osmometry, end-group determination or proton NMR.

As used herein, "polydispersity index", "PDI", "heterogeneity index", and "dispersity" refer to a measure of the distribution of molecular mass in a given polymer (such as a glucose oligomer) sample and can be calculated by dividing the weight average molecular weight by the number average molecular weight ($PDI = M_w/M_n$).

It shall be noted that the terms "glucose" and "glucopyranose" as used herein are considered as synonyms and used interchangeably. Similarly the terms "glucosyl" and "glucopyranosyl" units are used herein are considered as synonyms and used interchangeably.

As used herein, "glycosidic linkages" or "glycosidic bonds" will refer to the covalent the bonds connecting the sugar monomers within a saccharide oligomer (oligosaccharides and/or polysaccharides). Example of glycosidic linkage may include α-linked glucose oligomers with 1,6-α-D-glycosidic linkages (herein also referred to as α-D-(1,6) linkages or simply "α-(1,6)" linkages); 1,3-α-D-glycosidic linkages (herein also referred to as α-D-(1,3) linkages or simply "α-(1,3)" linkages; 1,4-α-D-glycosidic linkages (herein also referred to as α-D-(1,4) linkages or simply "α-(1,4)" linkages; 1,2-α-D-glycosidic linkages (herein also referred to as α-D-(1,2) linkages or simply "α-(1,2)" linkages; and combinations of such linkages typically associated with branched saccharide oligomers.

As used herein, the terms "glucansucrase", "glucosyltransferase", "glucoside hydrolase type 70", "GTF", and "GS" will refer to transglucosidases classified into family 70 of the glycoside-hydrolases typically found in lactic acid bacteria such as *Streptococcus, Leuconostoc*, Weisella or *Lactobacillus* genera (see Carbohydrate Active Enzymes database; "CAZy"; Cantarel et al., (2009) *Nucleic Acids Res* 37:D233-238). The GTF enzymes are able to polymerize the D-glucosyl units of sucrose to form homooligosaccharides or homopolysaccharides. Glucosyltransferases can be identified by characteristic structural features such as those described in Leemhuis et al. (*J. Biotechnology* (2013) 162: 250-272) and Monchois et al. (*FEMS Micro. Revs.* (1999) 23:131-151). Depending upon the specificity of the GTF enzyme, linear and/or branched glucans comprising various glycosidic linkages may be formed such as α-(1,2), α-(1,3), α-(1,4) and α-(1,6). Glucosyltransferases may also transfer the D-glucosyl units onto hydroxyl acceptor groups. A non-limiting list of acceptors may include carbohydrates, alcohols, polyols or flavonoids. Specific acceptors may also include maltose, isomaltose, isomaltotriose, and methyl-α-D-glucan, to name a few. The structure of the resultant glycosylated product is dependent upon the enzyme specificity. A non-limiting list of glucosyltransferase sequences is provided as amino acid SEQ ID NOs: 1, 3, 4 or 6. In one aspect, the glucosyltransferase is expressed in a truncated and/or mature form. In another embodiment, the polypeptide having glucosyltransferase activity comprises at least 90% identity, preferably 91, 92, 93, 94, 95, 96, 97, 98, 99 or 100% identity to SEQ ID NO: 1, 3, 4 or 6.

As used herein, the term "isomaltooligosaccharide" or "IMO" refers to a glucose oligomers comprised essentially of α-D-(1,6) glycosidic linkage typically having an average size of DP 2 to 20.

Isomaltooligosaccharides can be produced commercially from an enzymatic reaction of α-amylase, pullulanase, β-amylase, and α-glucosidase upon corn starch or starch derivative products. Commercially available products comprise a mixture of isomaltooligosaccharides (DP ranging from 3 to 8, e.g., isomaltotriose, isomaltotetraose, isomaltopentaose, isomaltohexaose, isomaltoheptaose, isomaltooctaose) and may also include panose.

As used herein, the term "dextran" refers to water soluble α-glucans comprising at least 95% α-D-(1,6) glycosidic linkages (typically with up to 5% α-D-(1,3) glycosidic linkages at branching points) that are more than 10% digestible as measured by the Association of Official Analytical Chemists International (AOAC) method 2009.01 ("AOAC 2009.01"). Dextrans often have an average molecular weight above 1000 kDa. As used herein, enzymes capable of synthesizing dextran from sucrose may be described as "dextransucrases" (EC 2.4.1.5).

As used herein, the term "mutan" refers to water insoluble α-glucans comprised primarily (50% or more of the glycosidic linkages present) of 1,3-α-D glycosidic linkages and typically have a degree of polymerization (DP) that is often greater than 9. Enzymes capable of synthesizing mutan or α-glucan oligomers comprising greater than 50% 1,3-α-D glycosidic linkages from sucrose may be described as "mutansucrases" (EC 2.4.1.-) with the proviso that the enzyme does not produce alternan.

As used herein, the term "alternan" refers to α-glucans having alternating 1,3-α-D glycosidic linkages and 1,6-α-D glycosidic linkages over at least 50% of the linear oligosaccharide backbone. Enzymes capable of synthesizing alternan from sucrose may be described as "alternansucrases" (EC 2.4.1.140).

As used herein, the term "reuteran" refers to soluble α-glucan comprised 1,4-α-D-glycosidic linkages (typically >50%); 1,6-α-D-glycosidic linkages; and 4,6-disubstituted α-glucosyl units at the branching points. Enzymes capable of synthesizing reuteran from sucrose may be described as "reuteransucrases" (EC 2.4.1.-).

As used herein, the terms "α-glucanohydrolase" and "glucanohydrolase" will refer to an enzyme capable of hydrolyzing an α-glucan oligomer. As used herein, the glucanohydrolase may be defined by the endohydrolysis activity towards certain α-D-glycosidic linkages. Examples may include, but are not limited to, dextranases (EC 3.2.1.1; capable of endohydrolyzing α-(1,6)-linked glycosidic bonds), mutanases (EC 3.2.1.59; capable of endohydrolyzing α-(1,3)-linked glycosidic bonds), and alternanases (EC 3.2.1.-; capable of endohydrolytically cleaving alternan). Various factors including, but not limited to, level of branching, the type of branching, and the relative branch length within certain α-glucans may adversely impact the ability of an α-glucanohydrolase to endohydrolyze some glycosidic linkages.

As used herein, the term "dextranase" (α-1,6-glucan-6-glucanohydrolase; EC 3.2.1.11) refers to an enzyme capable of endohydrolysis of 1,6-α-D-glycosidic linkages (the linkage predominantly found in dextran). Dextranases are known to be useful for a number of applications including the use as ingredient in dentifrice for prevent dental caries, plaque and/or tartar and for hydrolysis of raw sugar juice or syrup of sugar canes and sugar beets. Several microorganisms are known to be capable of producing dextranases, among them fungi of the genera *Penicillium, Paecilomyces, Aspergillus, Fusarium, Spicaria, Verticillium, Helminthosporium* and *Chaetomium*; bacteria of the genera *Lactobacillus, Streptococcus, Cellvibrio, Cytophaga, Brevibacterium, Pseudomonas, Corynebacterium, Arthrobacter* and *Flavobacterium*, and yeasts such as *Lipomyces starkeyi*. Food grade dextranases are commercially available. An example of a food grade dextrinase is DEXTRANASE® Plus L, an enzyme from *Chaetomium erraticum* sold by Novozymes A/S, Bagsvaerd, Denmark.

As used herein, the term "mutanase" (glucan endo-1,3-α-glucosidase; EC 3.2.1.59) refers to an enzyme which hydrolytically cleaves 1,3-α-D-glycosidic linkages (the linkage predominantly found in mutan). Mutanases are available from a variety of bacterial and fungal sources.

As used herein, the term "alternanase" (EC 3.2.1.-) refers to an enzyme which endo-hydrolytically cleaves alternan (U.S. Pat. No. 5,786,196 to Cote et al.).

As used herein, the term "wild type enzyme" will refer to an enzyme (full length and active truncated forms thereof) comprising the amino acid sequence as found in the organism from which was obtained and/or annotated. The enzyme (full length, mature or catalytically active truncation thereof) may be recombinantly produced in a microbial host cell. The enzyme is typically purified prior to being used as a processing aid in the production of the present soluble α-glucan fiber composition.

As used herein, the terms "substrate" and "suitable substrate" will refer a composition comprising sucrose. In one embodiment, the substrate composition may further comprise one or more suitable acceptors, such as maltose, isomaltose, isomaltotriose, and methyl-α-D-glucan, to name a few.

As used herein, the terms "suitable enzymatic reaction mixture", "suitable reaction components", "suitable aqueous reaction mixture", and "reaction mixture", refer to the materials (suitable substrate(s)) and water in which the reactants come into contact with the enzyme(s). The suitable reaction components may be comprised of a plurality of enzymes. In one aspect, the suitable reaction components comprises at least one glucansucrase enzyme.

As used herein, "one unit of glucansucrase activity" or "one unit of glucosyltransferase activity" is defined as the amount of enzyme required to convert 1 μmol of sucrose per minute when incubated with 200 g/L sucrose at pH 5.5 and 37° C. The sucrose concentration was determined using HPLC.

As used herein, the term "enzyme catalyst" refers to a catalyst comprising at least one polypeptide having the necessary enzymatic activity (i.e., at least one enzyme) to obtain the desired soluble glucan fiber composition from sucrose. The enzyme catalyst(s) may be in the form of a whole microbial cell, permeabilized microbial cell(s), one or more cell components of a microbial cell extract(s), partially purified enzyme(s) or purified enzyme(s). In certain embodiments the enzyme catalyst(s) may also be chemically modified (such as by pegylation or by reaction with cross-linking reagents). The enzyme catalyst(s) may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

As used herein, "pharmaceutically-acceptable" means that the compounds or compositions in question are suitable for use in contact with the tissues of humans and other animals without undue toxicity, incompatibility, instability, irritation, allergic response, and the like, commensurate with a reasonable benefit/risk ratio.

As used herein, the term "oligosaccharide" refers to homopolymers containing between 3 and about 30 monosaccharide units linked by α-glycosidic bonds.

As used herein the term "polysaccharide" refers to homopolymers containing greater than 30 monosaccharide units linked by α-glycosidic bonds.

As used herein, the term "food" is used in a broad sense herein to include a variety of substances that can be ingested by humans including, but not limited to, beverages, dairy products, baked goods, energy bars, jellies, jams, cereals, dietary supplements, and medicinal capsules or tablets.

As used herein, the term "pet food" or "animal feed" is used in a broad sense herein to include a variety of substances that can be ingested by nonhuman animals and may include, for example, dog food, cat food, and feed for livestock.

A "subject" is generally a human, although as will be appreciated by those skilled in the art, the subject may be a non-human animal. Thus, other subjects may include mammals, such as rodents (including mice, rats, hamsters and guinea pigs), cats, dogs, rabbits, cows, horses, goats, sheep, pigs, and primates (including monkeys, chimpanzees, orangutans and gorillas).

The term "cholesterol-related diseases", as used herein, includes but is not limited to conditions which involve elevated levels of cholesterol, in particular non-high density lipid (non-HDL) cholesterol in plasma, e.g., elevated levels of LDL cholesterol and elevated HDL/LDL ratio, hypercholesterolemia, and hypertriglyceridemia, among others. In patients with hypercholesteremia, lowering of LDL cholesterol is among the primary targets of therapy. In patients with hypertriglyceridemia, lower high serum triglyceride concentrations are among the primary targets of therapy. In particular, the treatment of cholesterol-related diseases as defined herein comprises the control of blood cholesterol levels, blood triglyceride levels, blood lipoprotein levels, blood glucose, and insulin sensitivity by administering the present glucan fiber or a composition comprising the present glucan fiber.

As used herein, "personal care products" means products used in the cosmetic treatment hair, skin, scalp, and teeth, including, but not limited to shampoos, body lotions, shower gels, topical moisturizers, toothpaste, tooth gels, mouthwashes, mouthrinses, anti-plaque rinses, and/or other topical treatments. In some particularly preferred embodiments, these products are utilized on humans, while in other embodiments, these products find cosmetic use with non-human animals (e.g., in certain veterinary applications).

As used herein, the terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

It would be recognized by one of ordinary skill in the art that modifications of amino acid sequences disclosed herein can be made while retaining the function associated with the disclosed amino acid sequences. For example, it is well known in the art that alterations in a gene which result in the production of a chemically equivalent amino acid at a given site may not affect the functional properties of the encoded protein. For example, any particular amino acid in an amino acid sequence disclosed herein may be substituted for another functionally equivalent amino acid. For the purposes of the present invention substitutions are defined as exchanges within one of the following five groups:
  1. Small aliphatic, nonpolar or slightly polar residues: Ala, Ser, Thr (Pro, Gly);
  2. Polar, negatively charged residues and their amides: Asp, Asn, Glu, Gln;
  3. Polar, positively charged residues: His, Arg, Lys;
  4. Large aliphatic, nonpolar residues: Met, Leu, Ile, Val (Cys); and
  5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g., plasmid) genes. Host organisms containing the transformed nucleic acid molecules are referred to as "transgenic", "recombinant" or "transformed" organisms.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Accelrys Software Corp., San Diego, Calif.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA), CLUSTALW (for example, version 1.83; Thompson et al., *Nucleic Acids Research*, 22(22):4673-4680 (1994)), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

Structural and Functional Properties of the Present Soluble α-Glucan Fiber Composition Human gastrointestinal enzymes readily recognize and digest linear α-glucan oligomers having a substantial amount of α-(1,4) glycosidic bonds. Replacing these linkages with alternative linkages such as α-(1,2), α-(1,3), and α-(1,6) typically reduces the digestibility of the α-glucan oligomers. Increasing the degree of branching (using the alternative linkages) may also reduce the relative level of digestibility.

The present soluble α-glucan fiber composition was prepared from cane sugar (sucrose) using one or more enzymatic processing aids that have essentially the same amino acid sequences as found in nature (or mature form or catalytically active truncations thereof) from microorganisms which having a long history of exposure to humans (microorganisms naturally found in the oral cavity or found in foods such a beer, fermented soybeans, etc.) and/or enzymes generally recognized as safe (GRAS). The soluble fibers have slow to no digestibility, exhibit high tolerance (i.e., as measured by an acceptable amount of gas formation), low viscosity (enabling use in a broad range of food applications), and are at least partially fermentable by gut microflora, providing possible prebiotic effects (for example, increasing the number and/or activity of bifidobacteria and lactic acid bacteria reported to be associated with providing potential prebiotic effects).

The present soluble α-glucan fiber composition is characterized by the following combination of parameters:

a. at least 95% α-(1,6) glycosidic linkages;
b. 1% or less α-(1,3) glycosidic linkages;
c. less than 2% α-(1,3,6) glycosidic linkages;
d. less than 1.5% α-(1,4) glycosidic linkages;
e. a weight average molecular weight of less than 20000 Daltons;
f. a viscosity of less than 0.25 Pascal second (Pa·s) at 12 wt % in water 20° C.;
g. a dextrose equivalence (DE) in the range of 1 to 30;
h. a digestibility of less than 12% as measured by the Association of Analytical Communities (AOAC) method 2009.01;
i. a solubility of at least 20% (w/w) in pH 7 water at 25° C.; and
j. a polydispersity index of less than 5.

In one embodiment, the present soluble α-glucan fiber composition comprises at least 95%, preferably at least 96, 97, or at least 98%, α-(1,6) glycosidic linkages.

In another embodiment, in addition to the α-(1,6) glycosidic linkage embodiments described above, the present soluble α-glucan fiber composition further comprises 1% or less, preferably 0.9, 0.8, 0.7, 0.6, 0.5, 0.4, 0.3, 0.2, or 0.1% or less α-(1,3) glycosidic linkages.

In another embodiment, in addition to the above embodiments, the present soluble α-glucan fiber composition further comprises less than 2%, preferably 0.5% to less than 2%, more preferably 0.5% to 1.5% α-(1,3,6) glycosidic linkages.

In another embodiment, in addition to the above mentioned glycosidic linkage content embodiments, the present soluble α-glucan fiber composition further comprises less than 1.5%, preferably 0.5% to less than 1.5%, α-(1,4) glycosidic linkages.

In another embodiment, in addition the above mentioned glycosidic linkage content embodiments, the present α-glucan fiber composition comprises a weight average molecular weight ($M_w$) of less than 20000 Daltons, preferably 500 Daltons to less than 20,000 Daltons, more preferably between 500 and 18,000 Daltons, and most preferably about 700 to about 18000 Daltons.

In another embodiment, in addition to any of the above features, the present α-glucan fiber composition comprises a viscosity of less than 250 centipoise (cP) (0.25 Pascal second (Pa·s), preferably less than 10 centipoise (cP) (0.01 Pascal second (Pa·s)), preferably less than 7 cP (0.007 Pas), more preferably less than 5 cP (0.005 Pas), more preferably less than 4 cP (0.004 Pas), and most preferably less than 3 cP (0.003 Pas) at 12 wt % in water at 20° C.

The present soluble α-glucan fiber composition has a digestibility of less than 10%, preferably less than 9%, 8%, 7%, 6%, 5%, 4%, 3%, 2% or 1% digestible as measured by the Association of Analytical Communities (AOAC) method 2009.01. In another aspect, the relative level of digestibility may be alternatively determined using AOAC 2011.25 (Integrated Total Dietary Fiber Assay) (McCleary et al., (2012) *J. AOAC Int.*, 95 (3), 824-844.

In addition to any of the above embodiments, the present soluble α-glucan fiber composition has a solubility of at least 20% (w/w), preferably at least 30%, 40%, 50%, 60%, or 70% in pH 7 water at 25° C.

In one embodiment, the present soluble α-glucan fiber composition comprises a reducing sugar content of less than 10 wt %, preferably less than 5 wt %, and most preferably 1 wt % or less.

In another embodiment, the present soluble α-glucan fiber composition comprises a number average molecular weight (Mn) between 400 and 2000 g/mol; preferably 500 to 1500 g/mol.

In one embodiment, the present soluble α-glucan fiber composition comprises a caloric content of less than 4 kcal/g, preferably less than 3 kcal/g, more preferably less than 2.5 kcal/g, and most preferably about 2 kcal/g or less.

Compositions Comprising Glucan Fibers

Depending upon the desired application, the present glucan fibers/fiber composition may be formulated (e.g., blended, mixed, incorporated into, etc.) with one or more other materials suitable for use in foods, personal care products and/or pharmaceuticals. As such, the present invention includes compositions comprising the present glucan fiber composition. The term "compositions comprising the present glucan fiber composition" in this context may include, for example, a nutritional or food composition, such as food products, food supplements, dietary supplements (for example, in the form of powders, liquids, gels, capsules, sachets or tablets) or functional foods. In a further embodiment, "compositions comprising the present glucan fiber composition" may also include personal care products, cosmetics, and pharmaceuticals.

The present glucan fibers/fiber composition may be directed as an ingredient in a desired product (e.g., foods, personal care products, etc.) or may be blended with one or more additional food grade materials to form a carbohydrate composition that is used in the desired product (e.g., foods, personal care products, etc.). The amount of the α-glucan fiber composition incorporated into the carbohydrate composition may vary according to the application. As such, the present invention comprises a carbohydrate composition comprising the present soluble α-glucan fiber composition. In one embodiment, the carbohydrate composition comprises 0.01 to 99 wt % (dry solids basis), preferably 0.1 to 90 wt %, more preferably 1 to 90%, and most preferably 5 to 80 wt % of the soluble glucan fiber composition described above.

The term "food" as used herein is intended to encompass food for human consumption as well as for animal consumption. By "functional food" it is meant any fresh or processed food claimed to have a health-promoting and/or disease-preventing and/or disease-(risk)-reducing property beyond the basic nutritional function of supplying nutrients. Functional food may include, for example, processed food or foods fortified with health-promoting additives. Examples of functional food are foods fortified with vitamins, or fermented foods with live cultures.

The carbohydrate composition comprising the present soluble α-glucan fiber composition may contain other materials known in the art for inclusion in nutritional compositions, such as water or other aqueous solutions, fats, sugars, starch, binders, thickeners, colorants, flavorants, odorants, acidulants (such as lactic acid or malic acid, among others), stabilizers, or high intensity sweeteners, or minerals, among others. Examples of suitable food products include bread, breakfast cereals, biscuits, cakes, cookies, crackers, yogurt, kefir, miso, natto, tempeh, kimchee, sauerkraut, water, milk, fruit juice, vegetable juice, carbonated soft drinks, non-carbonated soft drinks, coffee, tea, beer, wine, liquor, alcoholic drink, snacks, soups, frozen desserts, fried foods, pizza, pasta products, potato products, rice products, corn products, wheat products, dairy products, hard candies, nutritional bars, cereals, dough, processed meats and cheeses, yoghurts, ice cream confections, milk-based drinks, salad dressings, sauces, toppings, desserts, confectionery products, cereal-based snack bars, prepared dishes, and the like. The carbohydrate composition comprising the present α-glucan fiber may be in the form of a liquid, powder, tablet, cube, granule, gel, or syrup.

In one embodiment, the carbohydrate composition according to the invention may comprise at least two fiber sources (i.e., at least one additional fiber source beyond the present α-glucan fiber composition). In another embodiment, one fiber source is the present glucan fiber and the second fiber source is an oligo- or polysaccharide, selected from the group consisting of resistant/branched maltodextrins/fiber dextrins (such as NUTRIOSE® from Roquette Freres, Lestrem, France; FIBERSOL-2® from ADM-Matsutani LLC, Decatur, Ill.), polydextrose (LITESSE® from Danisco—DuPont Nutrition & Health, Wilmington, Del.), soluble corn fiber (for example, PROMITOR® from Tate & Lyle, London, UK), isomaltooligosaccharides (IMOs), alternan and/or maltoalternan oligosaccharides (MAOs) (for example, FIBERMALT™ from Aevotis GmbH, Potsdam, Germany; SUCROMALT™ (from Cargill Inc., Minneapolis, Minn.), pullulan, resistant starch, inulin, fructooligosaccharides (FOS), galactooligosaccharides (GOS), xylooligosaccharides, arabinoxylooligosaccharides, nigerooligosaccharides, gentiooligosaccharides, hemicellulose and fructose oligomer syrup. The present soluble α-glucan fiber can be added to foods as a replacement or supplement for conventional carbohydrates. As such, another embodiment of the invention is a food product comprising the present soluble α-glucan fiber. In another aspect, the food product comprises the soluble α-glucan fiber composition produced by the present process.

The soluble α-glucan fiber composition may be used in a carbohydrate composition and/or food product comprising one or more high intensity artificial sweeteners including, but not limited to stevia, aspartame, sucralose, neotame, acesulfame potassium, saccharin, and combinations thereof. The present soluble α-glucan fiber may be blended with sugar substitutes such as brazzein, curculin, erythritol, glycerol, glycyrrhizin, hydrogenated starch hydrolysates, inulin, isomalt, lactitol, mabinlin, maltitol, maltooligosaccharide, maltoalternan oligosaccharides (such as XTEND® SUCROMALT™, available from Cargill Inc., Minneapolis, Minn.), mannitol, miraculin, a mogroside mix, monatin, monellin, osladin, pentadin, sorbitol, stevia, tagatose, thaumatin, xylitol, and any combination thereof.

A food product containing the soluble α-glucan fiber composition will have a lower glycemic response, lower glycemic index, and lower glycemic load than a similar food product in which a conventional carbohydrate is used. Further, because the soluble α-glucan fiber is characterized by very low to no digestibility in the human stomach or small intestine, the caloric content of the food product is reduced. The present soluble α-glucan fiber may be used in the form of a powder, blended into a dry powder with other suitable food ingredients or may be blended or used in the form of a liquid syrup comprising the present dietary fiber (also referred to herein as an "soluble fiber syrup", "fiber syrup" or simply the "syrup"). The "syrup" can be added to food products as a source of soluble fiber. It can increase the fiber content of food products without having a negative impact on flavor, mouth feel, or texture.

The fiber syrup can be used in food products alone or in combination with bulking agents, such as sugar alcohols or maltodextrins, to reduce caloric content and/or to enhance nutritional profile of the product. The fiber syrup can also be used as a partial replacement for fat in food products.

The fiber syrup can be used in food products as a tenderizer or texturizer, to increase crispness or snap, to improve eye appeal, and/or to improve the rheology of dough, batter, or other food compositions. The fiber syrup can also be used in food products as a humectant, to increase product shelf life, and/or to produce a softer, moister texture. It can also be used in food products to reduce water activity or to immobilize and manage water. Additional uses of the fiber syrup may include: replacement of an egg wash and/or to enhance the surface sheen of a food product, to alter flour starch gelatinization temperature, to modify the texture of the product, and to enhance browning of the product.

The fiber syrup can be used in a variety of types of food products. One type of food product in which the present syrup can be very useful is bakery products (i.e., baked foods), such as cakes, brownies, cookies, cookie crisps, muffins, breads, and sweet doughs. Conventional bakery products can be relatively high in sugar and high in total carbohydrates. The use of the present syrup as an ingredient in bakery products can help lower the sugar and carbohydrate levels, as well as reduce the total calories, while increasing the fiber content of the bakery product.

There are two main categories of bakery products: yeast-raised and chemically-leavened. In yeast-raised products, like donuts, sweet doughs, and breads, the present fiber-containing syrup can be used to replace sugars, but a small amount of sugar may still be desired due to the need for a fermentation substrate for the yeast or for crust browning. The fiber syrup can be added with other liquids as a direct replacement for non-fiber containing syrups or liquid sweeteners. The dough would then be processed under conditions commonly used in the baking industry including being mixed, fermented, divided, formed or extruded into loaves or shapes, proofed, and baked or fried. The product can be baked or fried using conditions similar to traditional products. Breads are commonly baked at temperatures ranging from 420° F. to 520° F. (216-271° C.)°. for 20 to 23 minutes and doughnuts can be fried at temperatures ranging from 400415° F. (204-213° C.), although other temperatures and times could also be used.

Chemically leavened products typically have more sugar and may contain have a higher level of the carbohydrate compositions and/or edible syrups comprising the present soluble α-glucan fiber. A finished cookie can contain 30% sugar, which could be replaced, entirely or partially, with carbohydrate compositions and/or syrups comprising the present glucan fiber composition. These products could have a pH of 4-9.5, for example. The moisture content can be between 2-40%, for example.

The present carbohydrate compositions and/or fiber-containing syrups are readily incorporated and may be added to the fat at the beginning of mixing during a creaming step or in any method similar to the syrup or dry sweetener that it is being used to replace. The product would be mixed and then formed, for example by being sheeted, rotary cut, wire cut, or through another forming process. The products would then be baked under typical baking conditions, for example at 200450° F. (93-232° C.).

Another type of food product in which the carbohydrate compositions and/or fiber-containing syrups can be used is breakfast cereal. For example, fiber-containing syrups could be used to replace all or part of the sugar in extruded cereal pieces and/or in the coating on the outside of those pieces. The coating is typically 30-60% of the total weight of the finished cereal piece. The syrup can be applied in a spray or drizzled on, for example.

Another type of food product in which the present α-glucan fiber composition (optionally used in the form of a carbohydrate composition and/or fiber-containing syrup) can be used is dairy products. Examples of dairy products in which it can be used include yogurt, yogurt drinks, milk drinks, flavored milks, smoothies, ice cream, shakes, cottage cheese, cottage cheese dressing, and dairy desserts, such as quarg and the whipped mousse-type products. This would include dairy products that are intended to be consumed directly (such as packaged smoothies) as well as those that are intended to be blended with other ingredients (such as blended smoothies). It can be used in pasteurized dairy products, such as ones that are pasteurized at a temperature from 160° F. to 285° F. (71-141° C.).

Another type of food product in which the composition comprising the α-glucan fiber composition can be used is confections. Examples of confections in which it can be used include hard candies, fondants, nougats and marshmallows, gelatin jelly candies or gummies, jellies, chocolate, licorice, chewing gum, caramels and toffees, chews, mints, tableted confections, and fruit snacks. In fruit snacks, a composition comprising the present α-glucan fiber could be used in combination with fruit juice. The fruit juice would provide the majority of the sweetness, and the composition comprising the glucan fiber would reduce the total sugar content and add fiber. The present compositions comprising the glucan fiber can be added to the initial candy slurry and heated to the finished solids content. The slurry could be heated from 200-305° F. (93-152° C.). to achieve the finished solids content. Acid could be added before or after heating to give a finished pH of 2-7. The composition comprising the glucan fiber could be used as a replacement for 0-100% of the sugar and 1-100% of the corn syrup or other sweeteners present.

Another type of food product in which a composition comprising the α-glucan fiber composition can be used is jams and jellies. Jams and jellies are made from fruit. A jam contains fruit pieces, while jelly is made from fruit juice. The composition comprising the present fiber can be used in place of sugar or other sweeteners as follows: Weigh fruit and juice into a tank. Premix sugar, the fiber-containing composition and pectin. Add the dry composition to the liquid and cook to a temperature of 214-220° F. (101-104° C.). Hot fill into jars and retort for 5-30 minutes.

Another type of food product in which a composition comprising the present α-glucan fiber composition (such as a fiber-containing syrup) can be used is beverages. Examples of beverages in which it can be used include carbonated beverages, fruit juices, concentrated juice mixes (e.g., margarita mix), clear waters, and beverage dry mixes. The use of the present α-glucan fiber may overcome the clarity problems that result when other types of fiber are added to beverages. A complete replacement of sugars may be possible (which could be, for example, being up to 12% or more of the total formula).

Another type of food product is high solids fillings. Examples of high solids fillings include fillings in snack bars, toaster pastries, donuts, and cookies. The high solids filling could be an acid/fruit filling or a savory filling, for example. The soluble α-glucan fiber composition could be added to products that would be consumed as is, or products that would undergo further processing, by a food processor (additional baking) or by a consumer (bake stable filling). In some embodiments of the invention, the high solids fillings would have a solids concentration between 67-90%. The solids could be entirely replaced with a composition comprising the present α-glucan fiber or it could be used for a partial replacement of the other sweetener solids present (e.g., replacement of current solids from 5-100%). Typically fruit fillings would have a pH of 2-6, while savory fillings would be between 4-8 pH. Fillings could be prepared cold or heated at up to 250° F. (121° C.) to evaporate to the desired finished solids content.

Another type of food product in which the α-glucan fiber composition or a carbohydrate composition (comprising the α-glucan fiber composition) can be used is extruded and sheeted snacks. Examples of extruded and sheeted can be used include puffed snacks, crackers, tortilla chips, and corn chips. In preparing an extruded piece, a composition comprising the present glucan fiber would be added directly with the dry products. A small amount of water would be added in the extruder, and then it would pass through various zones ranging from 100° F. to 300° F. (38-149° C.). The dried product could be added at levels from 0-50% of the dry products mixture. A syrup comprising the present glucan fiber could also be added at one of the liquid ports along the extruder. The product would come out at either a low moisture content (5%) and then baked to remove the excess moisture, or at a slightly higher moisture content (10%) and then fried to remove moisture and cook out the product. Baking could be at temperatures up to 500° F. (260° C.). for 20 minutes. Baking would more typically be at 350° F. (177° C.) for 10 minutes. Frying would typically be at 350° F. (177° C.) for 2-5 minutes. In a sheeted snack, the composition comprising the present glucan fiber could be used as a partial replacement of the other dry ingredients (for example, flour). It could be from 0-50% of the dry weight. The product would be dry mixed, and then water added to form cohesive dough. The product mix could have a pH from 5 to 8. The dough would then be sheeted and cut and then baked or fried. Baking could be at temperatures up to 500° F. (260° C.) for 20 minutes. Frying would typically be at 350° F. (177° C.) for 2-5 minutes. Another potential benefit from the use of a composition comprising the present glucan fiber is a reduction of the fat content of fried snacks by as much as 15% when it is added as an internal ingredient or as a coating on the outside of a fried food.

Another type of food product in which a fiber-containing syrup can be used is gelatin desserts. The ingredients for gelatin desserts are often sold as a dry mix with gelatin as a gelling agent. The sugar solids could be replaced partially or entirely with a composition comprising the present glucan fiber in the dry mix. The dry mix can then be mixed with water and heated to 212° F. (100° C.). to dissolve the gelatin and then more water and/or fruit can be added to complete the gelatin dessert. The gelatin is then allowed to cool and set. Gelatin can also be sold in shelf stable packs. In that case the stabilizer is usually carrageenan-based. As stated above, a composition comprising the present glucan fiber could be used to replace up to 100% of the other sweetener solids. The dry ingredients are mixed into the liquids and then pasteurized and put into cups and allowed to cool and set.

Another type of food product in which a composition comprising the present glucan fiber can be used is snack bars. Examples of snack bars in which it can be used include breakfast and meal replacement bars, nutrition bars, granola bars, protein bars, and cereal bars. It could be used in any part of the snack bars, such as in the high solids filling, the binding syrup or the particulate portion. A complete or partial replacement of sugar in the binding syrup may be possible. The binding syrup is typically from 50-90% solids and applied at a ratio ranging from 10% binding syrup to 90% particulates, to 70% binding syrup to 30% particulates. The binding syrup is made by heating a solution of sweeteners, bulking agents and other binders (like starch) to 160-230° F. (71-110° C.) (depending on the finished solids needed in the syrup). The syrup is then mixed with the particulates to coat the particulates, providing a coating throughout the matrix. A composition comprising the present glucan fiber could also be used in the particulates themselves. This could be an extruded piece, directly expanded or gun puffed. It could be used in combination with another grain ingredient, corn meal, rice flour or other similar ingredient.

Another type of food product in which the composition comprising the present glucan fiber syrup can be used is cheese, cheese sauces, and other cheese products. Examples of cheese, cheese sauces, and other cheese products in which it can be used include lower milk solids cheese, lower fat cheese, and calorie reduced cheese. In block cheese, it can help to improve the melting characteristics, or to decrease the effect of the melt limitation added by other ingredients such as starch. It could also be used in cheese sauces, for example as a bulking agent, to replace fat, milk solids, or other typical bulking agents.

Another type of food product in which a composition comprising the present glucan fiber can be used is films that are edible and/or water soluble. Examples of films in which it can be used include films that are used to enclose dry mixes for a variety of foods and beverages that are intended to be dissolved in water, or films that are used to deliver color or flavors such as a spice film that is added to a food after cooking while still hot. Other film applications include, but are not limited to, fruit and vegetable leathers, and other flexible films.

In another embodiment, compositions comprising the present glucan fiber can be used is soups, syrups, sauces, and dressings. A typical dressing could be from 0-50% oil, with a pH range of 2-7. It could be cold processed or heat processed. It would be mixed, and then stabilizer would be added. The composition comprising the present glucan fiber could easily be added in liquid or dry form with the other ingredients as needed. The dressing composition may need to be heated to activate the stabilizer. Typical heating conditions would be from 170-200° F. (77-93° C.) for 1-30 minutes. After cooling, the oil is added to make a pre-emulsion. The product is then emulsified using a homogenizer, colloid mill, or other high shear process.

Sauces can have from 0-10% oil and from 10-50% total solids, and can have a pH from 2-8. Sauces can be cold processed or heat processed. The ingredients are mixed and then heat processed. The composition comprising the present glucan fiber could easily be added in liquid or dry form with the other ingredients as needed. Typical heating would be from 170-200° F. (77-93° C.) for 1-30 minutes.

Soups are more typically 20-50% solids and in a more neutral pH range (4-8). They can be a dry mix, to which a dry composition comprising the present glucan fiber could be added, or a liquid soup which is canned and then retorted. In soups, resistant corn syrup could be used up to 50% solids, though a more typical usage would be to deliver 5 g of fiber/serving.

Another type of food product in which a composition comprising the present α-glucan fiber composition can be used is coffee creamers. Examples of coffee creamers in which it can be used include both liquid and dry creamers. A dry blended coffee creamer can be blended with commercial creamer powders of the following fat types: soybean, coconut, palm, sunflower, or canola oil, or butterfat. These fats can be non-hydrogenated or hydrogenated. The composition comprising the present α-glucan fiber composition can be added as a fiber source, optionally together with fructo-oligosaccharides, polydextrose, inulin, maltodextrin, resistant starch, sucrose, and/or conventional corn syrup solids. The composition can also contain high intensity sweeteners, such as sucralose, acesulfame potassium, aspartame, or combinations thereof. These ingredients can be dry blended to produce the desired composition.

A spray dried creamer powder is a combination of fat, protein and carbohydrates, emulsifiers, emulsifying salts, sweeteners, and anti-caking agents. The fat source can be one or more of soybean, coconut, palm, sunflower, or canola oil, or butterfat. The protein can be sodium or calcium caseinates, milk proteins, whey proteins, wheat proteins, or soy proteins. The carbohydrate could be a composition comprising the present α-glucan fiber composition alone or in combination with fructooligosaccharides, polydextrose, inulin, resistant starch, maltodextrin, sucrose, corn syrup or any combination thereof. The emulsifiers can be mono- and diglycerides, acetylated mono- and diglycerides, or propylene glycol monoesters. The salts can be trisodium citrate, monosodium phosphate, disodium phosphate, trisodium phosphate, tetrasodium pyrophosphate, monopotassium phosphate, and/or dipotassium phosphate. The composition can also contain high intensity sweeteners, such as those describe above. Suitable anti-caking agents include sodium silicoaluminates or silica dioxides. The products are combined in slurry, optionally homogenized, and spray dried in either a granular or agglomerated form.

Liquid coffee creamers are simply a homogenized and pasteurized emulsion of fat (either dairy fat or hydrogenated vegetable oil), some milk solids or caseinates, corn syrup, and vanilla or other flavors, as well as a stabilizing blend. The product is usually pasteurized via HTST (high temperature short time) at 185° F. (85° C.) for 30 seconds, or UHT (ultra-high temperature), at 285° F. (141° C.) for 4 seconds, and homogenized in a two stage homogenizer at 500-3000 psi (3.45-20.7 MPa) first stage, and 200-1000 psi (1.38-6.89 MPa) second stage. The coffee creamer is usually stabilized so that it does not break down when added to the coffee.

Another type of food product in which a composition comprising the present α-glucan fiber composition (such as a fiber-containing syrup) can be used is food coatings such as icings, frostings, and glazes. In icings and frostings, the fiber-containing syrup can be used as a sweetener replacement (complete or partial) to lower caloric content and increase fiber content. Glazes are typically about 70-90% sugar, with most of the rest being water, and the fiber-containing syrup can be used to entirely or partially replace the sugar. Frosting typically contains about 2-40% of a liquid/solid fat combination, about 20-75% sweetener solids, color, flavor, and water. The fiber-containing syrup can be used to replace all or part of the sweetener solids, or as a bulking agent in lower fat systems.

Another type of food product in which the fiber-containing syrup can be used is pet food, such as dry or moist dog food. Pet foods are made in a variety of ways, such as extrusion, forming, and formulating as gravies. The fiber-containing syrup could be used at levels of 0-50% in each of these types.

Another type of food product in which a composition comprising the present α-glucan fiber composition, such as a syrup, can be used is fish and meat. Conventional corn syrup is already used in some meats, so a fiber-containing syrup can be used as a partial or complete substitute. For example, the syrup could be added to brine before it is vacuum tumbled or injected into the meat. It could be added with salt and phosphates, and optionally with water binding ingredients such as starch, carrageenan, or soy proteins. This would be used to add fiber, a typical level would be 5 g/serving which would allow a claim of excellent source of fiber.

Personal Care and/or Pharmaceutical Compositions Comprising the Present Soluble Fiber The present glucan fiber and/or compositions comprising the present glucan fiber may be used in personal care products. For example, one may be able to use such materials as a humectants, hydrocolloids or possibly thickening agents. The present fibers and/or compositions comprising the present fibers may be used in conjunction with one or more other types of thickening agents if desired, such as those disclosed in U.S. Pat. No. 8,541,041, the disclosure of which is incorporated herein by reference in its entirety.

Personal care products herein include but are not limited to, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient. An active ingredient is generally recognized as an ingredient that produces the intended pharmacological or cosmetic effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup or other product including, but not limited to, a lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, toothpaste, or mouthwash, for example.

A pharmaceutical product herein can be in the form of an emulsion, liquid, elixir, gel, suspension, solution, cream, capsule, tablet, sachet or ointment, for example. Also, a pharmaceutical product herein can be in the form of any of the personal care products disclosed herein. A pharmaceutical product can further comprise one or more pharmaceutically acceptable carriers, diluents, and/or pharmaceutically acceptable salts. The present fibers and/or compositions comprising the present fibers can also be used in capsules, encapsulants, tablet coatings, and as an excipients for medicaments and drugs.

Enzymatic Synthesis of the Soluble α-Glucan Fiber Composition

Methods are provided to enzymatically produce a soluble α-glucan fiber composition. Two different methods are described herein. In one embodiment, the "single enzyme" method comprises the use of at least one glucosyltransferase (in the absence of an α-glucanohydrolase) belonging to glucoside hydrolase type 70 (E.C. 2.4.1.-) capable of catalyzing the synthesis of a digestion resistant soluble α-glucan fiber composition using sucrose as a substrate.

Glycoside hydrolase family 70 enzymes are transglucosidases produced by lactic acid bacteria such as *Streptococcus, Leuconostoc, Weisella* or *Lactobacillus* genera (see Carbohydrate Active Enzymes database; "CAZy"; Cantarel et al., (2009) *Nucleic Acids Res* 37:D233-238). The recombinantly expressed glucosyltransferases preferably have an amino acid sequence identical to that found in nature (i.e., the same as the full length sequence as found in the source organism or a catalytically active truncation thereof).

The GTF enzymes are able to polymerize the D-glucosyl units of sucrose to form homooligosaccharides or homopolysaccharides. Depending upon the specificity of the GTF enzyme, linear and/or branched glucans comprising various glycosidic linkages may be formed such as α-(1,2), α-(1,3), α-(1,4) and α-(1,6). Glucosyltransferases may also transfer the D-glucosyl units onto hydroxyl acceptor groups. A non-limiting list of acceptors may include carbohydrates, alcohols, polyols or flavonoids. The structure of the resultant glucosylated product is dependent upon the enzyme specificity.

In the present invention the D-glucopyranosyl donor is sucrose. As such the reaction is:

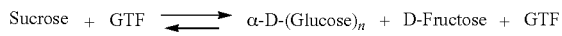

Sucrose + GTF ⇌ α-D-(Glucose)$_n$ + D-Fructose + GTF

The type of glycosidic linkage predominantly formed is used to name/classify the glucosyltransferase enzyme. Examples include dextransucrases (α-(1,6) linkages; EC 2.4.1.5), mutansucrases (α-(1,3) linkages; EC 2.4.1.-), alternansucrases (alternating α(1,3)-α(1,6) backbone; EC 2.4.1.140), and reuteransucrases (mix of α-(1,4) and α-(1,6) linkages; EC 2.4.1.-).

In one aspect, the glucosyltransferase (GTF) is capable of forming glucans having α-(1,6) glycosidic linkages with the proviso that that glucan product is not alternan (i.e., the enzyme is not an alternansucrase).

In one aspect, the glucosyltransferase comprises an amino acid sequence having at least 90% identity, preferably at least 91, 92, 93, 94, 95, 96, 97, 98, 99 or 100% identity to SEQ ID NO: 1, 3, 4 or 6. In a preferred aspect, the glucosyltransferase comprises an amino acid sequence selected from the group consisting of SEQ ID NOs: 1, 3, 4 or 6. However, it should be noted that some wild type sequences may be found in nature in a truncated form. As such, and in a further embodiment, the glucosyltransferase suitable for use may be a truncated and/or mature form of the wild type sequence. In a further embodiment, the truncated/mature form of the glucosyltransferase comprises a sequence derived from the full length wild type amino acid sequence selected from the group consisting of SEQ ID NOs: 1 and 4. In another embodiment, the glucosyltransferase may be truncated and/or in a mature form (i.e., signal peptide removed) and will have an amino acid sequence selected from the group consisting of SEQ ID NOs: 3 and 6.

The concentration of the catalyst in the aqueous reaction formulation depends on the specific catalytic activity of the catalyst, and is chosen to obtain the desired rate of reaction. The weight of each catalyst (either a single glucosyltransferase or individually a glucosyltransferase and α-glucanohydrolase) reactions typically ranges from 0.0001 mg to 20 mg per mL of total reaction volume, preferably from 0.001 mg to 10 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

The pH of the final reaction formulation is from about 3 to about 8, preferably from about 4 to about 8, more preferably from about 5 to about 8, even more preferably about 5.5 to about 7.5, and yet even more preferably about 5.5 to about 6.5. The pH of the reaction may optionally be controlled by the addition of a suitable buffer including, but not limited to, phosphate, pyrophosphate, bicarbonate, acetate, or citrate. The concentration of buffer, when employed, is typically from 0.1 mM to 1.0 M, preferably from 1 mM to 300 mM, most preferably from 10 mM to 100 mM.

The sucrose concentration initially present when the reaction components are combined is at least 50 g/L, preferably 50 g/L to 600 g/L, more preferably 100 g/L to 500 g/L, more preferably 150 g/L to 450 g/L, and most preferably 250 g/L to 450 g/L. The substrate for the α-glucanohydrolase (when present) will be the members of the glucose oligomer population formed by the glucosyltransferase. As the glucose oligomers present in the reaction system may act as acceptors, the exact concentration of each species present in the reaction system will vary. Additionally, other acceptors may be added (i.e., external acceptors) to the initial reaction mixture such as maltose, isomaltose, isomaltotriose, and methyl-α-D-glucan, to name a few.

The length of the reaction may vary and may often be determined by the amount of time it takes to use all of the available sucrose substrate. In one embodiment, the reaction is conducted until at least 90%, preferably at least 95% and most preferably at least 99% of the sucrose initially present in the reaction mixture is consumed. In another embodiment, the reaction time is 1 hour to 168 hours, preferably 1 hour to 72 hours, and most preferably 1 hour to 24 hours.

Single Enzyme Method (Glucosyltransferase)

Two glucosyltransferases/glucansucrases have been identified capable of producing the present α-glucan fiber composition in the absence of an α-glucanohydrolase. Specifically, a glucosyltransferase from *Lactobacillus animalis* KCTC 3501 (GENBANK® gi: 335358117 (or a catalytically active truncation thereof suitable for expression in the recombinant microbial host cell); also referred to herein as the "8117" glucosyltransferase or "GTF8117") can produce the present α-glucan fiber composition. In one aspect, the *Lactobacillus animalis* GTF8117 may be produced as a catalytically active fragment of the full length sequence reported in GENBANK® gi: 335358117. In one embodiment, the present α-glucan fiber composition is produced using the *Lactobacillus animalis* GTF8117 glucosyltransferase or a catalytically active fragment thereof.

In one embodiment, a method to produce an α-glucan fiber composition is provided comprising:
   a. providing a set of reaction components comprising:
      i. sucrose;
      ii. at least one polypeptide having glucosyltransferase activity having at least 90% identity to SEQ ID NO: 1,3, 4 or 6; and
      iii. optionally one more acceptors;
   b. combining under suitable aqueous reaction conditions the set of reaction components of (a) to form a single reaction mixture, whereby a product mixture comprising glucose oligomers is formed;
   c. optionally isolating the soluble α-glucan fiber composition from the product mixture comprising glucose oligomers; and
   d. optionally concentrating the soluble α-glucan fiber composition.

In a preferred embodiment, the present α-glucan fiber composition is produced using a glucosyltransferase enzyme having an amino acid sequence having at least 90%, preferably 91, 92, 93, 94, 95, 96, 97, 98, 99, or 100% to SEQ ID NO: 1 (the full length form) or SEQ ID NO: 3 (a catalytically active mature form) with the understanding the such enzymes will retain a similar activity and produce a product profile consistent with the present α-glucan fiber composition.

In another embodiment, a glucosyltransferase from *Streptococcus salivarius* M18 GENBANK® gi: 345526831 (or a catalytically active truncation thereof suitable for expression in the recombinant microbial host cell; herein also referred to as the "6831" glucosyltransferase or simply "GTF6831") has also been identified as being capable of producing the present α-glucan fiber composition in the absence of an α-glucanohydrolase (e.g., dextranase, mutanase, etc.). In one aspect, the *Streptococcus salivarius* GTF6831 may be produced as a catalytically active fragment of the full length sequence reported in GENBANK® gi: 345526831. In one embodiment, the present α-glucan fiber composition is produced using the *Streptococcus salivarius* GTF6831 glucosyltransferase or a catalytically active fragment thereof. In a preferred embodiment, the present α-glucan fiber composition is produced using a glucosyltransferase enzyme having an amino acid sequence having at least 90%, preferably 91, 92, 93, 94, 95, 96, 97, 98, 99, or 100% to SEQ ID NO: 4 (the full length form) or SEQ ID NO: 6 (a catalytically active mature form) with the understanding the such enzymes will retain a similar activity and produce a product profile consistent with the present α-glucan fiber composition.

The temperature of the enzymatic reaction system comprising concomitant use of at least one glucosyltransferase may be chosen to control both the reaction rate and the stability of the enzyme catalyst activity. The temperature of the reaction may range from just above the freezing point of the reaction formulation (approximately 0° C.) to about 60° C., with a preferred range of 5° C. to about 55° C., and a more preferred range of reaction temperature of from about 20° C. to about 47° C.

Methods to Identify Substantially Similar Enzymes Having the Desired Activity

The skilled artisan recognizes that substantially similar enzyme sequences may also be used in the present compositions and methods so long as the desired activity is retained (i.e., glucosyltransferase activity capable of forming glucans having the desired glycosidic linkages). For example, it has been demonstrated that catalytically activity truncations may be prepared and used so long as the desired activity is retained (or even improved in terms of specific activity). In one embodiment, substantially similar sequences are defined by their ability to hybridize, under highly stringent conditions with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash of 0.1×SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook, J. and Russell, D., T., supra). For hybridizations with shorter nucleic acids, i.e., oligonucleotides, the position of mismatches becomes more important, and the length of the oligonucleotide determines its specificity. In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, N Y (1988); *Biocomputing: Informatics and Genome Projects* (Smith, D. W., ed.) Academic Press, N Y (1993); *Computer Analysis of Sequence Data, Part I* (Griffin, A. M., and Griffin, H. G., eds.) Humana Press, N J (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS,* 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 20%, preferably at least 30%, 40%, 50%, 60%, 70%, 80%, 85%, 90%, 91%, 92%, 93%, 94%, 95%, 96%, 97%, 98%, or 99% identical to the amino acid sequences reported herein. In another aspect, suitable isolated nucleic acid molecules encode a polypeptide having an amino acid sequence that is at least about 20%, preferably at least 30%, 40%, 50%, 60%, 70%, 80%, 85%, 90%, 91%, 92%, 93%, 94%, 95%, 96%, 97%, 98%, or 99% identical to the amino acid sequences reported herein; with the proviso that the polypeptide retains the respective activity (i.e., glucosyltransferase or α-glucanohydrolase activity).

Gas Production

A rapid rate of gas production in the lower gastrointestinal tract gives rise to gastrointestinal discomfort such as flatulence and bloating, whereas if gas production is gradual and low the body can more easily cope. For example, inulin gives a boost of gas production which is rapid and high when compared to the present glucan fiber composition at an equivalent dosage (grams soluble fiber), whereas the present glucan fiber composition preferably has a rate of gas release that is lower than that of inulin at an equivalent dosage.

In one embodiment, the soluble α-glucan fiber composition of the invention comprises a rate of gas production that is well tolerated for food applications. In one embodiment, the relative rate of gas production is no more than the rate observed for inulin under similar conditions, preferably the same or less than inulin, more preferably less than inulin, and most preferably much less than inulin at an equivalent dosage. In another embodiment, the relative rate of gas formation is measured over 3 hours or 24 hours using the methods described herein. In a preferred aspect, the rate of gas formation is at least 1%, preferably 2%, 3%, 4%, 5%, 6%, 7%, 8%, 9%, 10%, 15%, 20%, 25% or at least 30% less than the rate observed for inulin under the same reaction conditions.

Beneficial Physiological Properties

Short Chain Fatty Acid Production

Use of the compounds according to the present invention may facilitate the production of energy yielding metabolites through colonic fermentation. Use of compounds according to the invention may facilitate the production of short chain fatty acids, such as propionate and/or butyrate. SCFAs are known to lower cholesterol. Consequently, the compounds of the invention may lower the risk of developing high cholesterol. The present glucan fiber composition may stimulate the production of short chain fatty acids, especially proprionate and/or butyrate, in fermentation studies. As the production of short chain fatty acids (SCFA) or the increased ratio of SCFA to acetate is beneficial for the control of cholesterol levels in a mammal in need thereof, the current invention may be of particular interest to nutritionists and consumers for the prevention and/or treatment of cardiovascular risks. Thus, another aspect of the invention provides a method for improving the health of a subject comprising administering a composition comprising the present α-glucan fiber composition to a subject in an amount effective to exert a beneficial effect on the health of said subject, such as for treating cholesterol-related diseases. In addition, it is generally known that short chain fatty acids lower the pH in the gut and this helps calcium absorption. Thus, compounds according to the present invention may also affect mineral absorption. This means that they may also improve bone health, or prevent or treat osteoporosis by lowering the pH due to SCFA increases in the gut. The production of SCFA may increase viscosity in small intestine which reduces the re-absorption of bile acids; increasing the synthesis of bile acids from cholesterol and reduces circulating low density lipoprotein (LDL) cholesterol.

An "effective amount" of a compound or composition as defined herein refers to an amount effective, at dosages and for periods of time necessary, to achieve a desired beneficial physiological effect, such as lowering of blood cholesterol, increasing short chain fatty acid production or preventing or treating a gastrointestinal disorder. For instance, the amount of a composition administered to a subject will vary depending upon factors such as the subject's condition, the subject's body weight, the age of the subject, and whether a composition is the sole source of nutrition. The effective amount may be readily set by a medical practitioner or dietician. In general, a sufficient amount of the composition is administered to provide the subject with up to about 50 g of dietary fiber (insoluble and soluble) per day; for example about 25 g to about 35 g of dietary fiber per day. The amount of the present soluble α-glucan fiber composition that the subject receives is preferably in the range of about 0.1 g to about 50 g per day, more preferably in the rate of 0.5 g to 20 g per day, and most preferably 1 to 10 g per day. A compound or composition as defined herein may be taken in multiple doses, for example 1 to 5 times, spread out over the day or acutely, or may be taken in a single dose. A compound or composition as defined herein may also be fed continuously over a desired period. In certain embodiments, the desired period is at least one week or at least two weeks or at least three weeks or at least one month or at least six months.

In a preferred embodiment, the present invention provides a method for decreasing blood triglyceride levels in a subject in need thereof by administering a compound or a composition as defined herein to a subject in need thereof. In another preferred embodiment, the invention provides a method for decreasing low density lipoprotein levels in a subject in need thereof by administering a compound or a composition as defined herein to a subject in need thereof. In another preferred embodiment, the invention provides a method for increasing high density lipoprotein levels in a subject in need thereof by administering a compound or a composition as defined herein to a subject in need thereof.

Attenuation of Postprandial Blood Glucose Concentrations/Glycemic Response

The presence of bonds other than $\alpha$-(1,4) backbone linkages in the present $\alpha$-glucan fiber composition provides improved digestion resistance as enzymes of the human digestion track may have difficulty hydrolyzing such bonds and/or branched linkages. The presence of branches provides partial or complete indigestibility to glucan fibers, and therefore virtually no or a slower absorption of glucose into the body, which results in a lower glycemic response. Accordingly, the present invention provides an $\alpha$-glucan fiber composition for the manufacture of food and drink compositions resulting in a lower glycemic response. For example, these compounds can be used to replace sugar or other rapidly digestible carbohydrates, and thereby lower the glycemic load of foods, reduce calories, and/or lower the energy density of foods. Also, the stability of the present $\alpha$-glucan fiber composition possessing these types of bonds allows them to be easily passed through into the large intestine where they may serve as a substrate specific for the colonic microbial flora.

Improvement of Gut Health

In a further embodiment, compounds of the present invention may be used for the treatment and/or improvement of gut health. The present $\alpha$-glucan fiber composition is preferably slowly fermented in the gut by the gut microflora. Preferably, the present compounds exhibit in an in vitro gut model a tolerance no worse than inulin or other commercially available fibers such as PROMITOR® (soluble corn fiber, Tate & Lyle), NUTRIOSE® (soluble corn fiber or dextrin, Roquette), or FIBERSOL®-2 (digestion-resistant maltodextrin, Archer Daniels Midland Company & Matsutani Chemical), (i.e., similar level of gas production), preferably an improved tolerance over one or more of the commercially available fibers, i.e. the fermentation of the present glucan fiber results in less gas production than inulin in 3 hours or 24 hours, thereby lowering discomfort, such as flatulence and bloating, due to gas formation. In one aspect, the present invention also relates to a method for moderating gas formation in the gastrointestinal tract of a subject by administering a compound or a composition as defined herein to a subject in need thereof, so as to decrease gut pain or gut discomfort due to flatulence and bloating. In further embodiments, compositions of the present invention provide subjects with improved tolerance to food fermentation, and may be combined with fibers, such as inulin or FOS, GOS, or lactulose to improve tolerance by lowering gas production.

In another embodiment, compounds of the present invention may be administered to improve laxation or improve regularity by increasing stool bulk.

Prebiotics and Probiotics

The soluble $\alpha$-glucan fiber composition(s) may be useful as prebiotics, or as "synbiotics" when used in combination with probiotics, as discussed below. By "prebiotic" it is meant a food ingredient that beneficially affects the subject by selectively stimulating the growth and/or activity of one or a limited number of bacteria in the gastrointestinal tract, particularly the colon, and thus improves the health of the host. Examples of prebiotics include fructooligosaccharides, inulin, polydextrose, resistant starch, soluble corn fiber, glucooligosaccharides and galactooligosaccharides, arabinoxylan-oligosaccharides, lactitol, and lactulose.

In another embodiment, compositions comprising the soluble $\alpha$-glucan fiber composition further comprise at least one probiotic organism. By "probiotic organism" it is meant living microbiological dietary supplements that provide beneficial effects to the subject through their function in the digestive tract. In order to be effective the probiotic microorganisms must be able to survive the digestive conditions, and they must be able to colonize the gastrointestinal tract at least temporarily without any harm to the subject. Only certain strains of microorganisms have these properties. Preferably, the probiotic microorganism is selected from the group comprising *Lactobacillus* spp., *Bifidobacterium* spp., *Bacillus* spp., *Enterococcus* spp., *Escherichia* spp., *Streptococcus* spp., and *Saccharomyces* spp. Specific microorganisms include, but are not limited to *Bacillus subtilis, Bacillus cereus, Bifidobacterium bificum, Bifidobacterium breve, Bifidobacterium infantis, Bifidobacterium lactis, Bifidobacterium longum, Bifidobacterium thermophilum, Enterococcus faecium, Enterococcus faecium, Lactobacillus acidophilus, Lactobacillus bulgaricus, Lactobacillus casei, Lactobacillus lactis, Lactobacillus plantarum, Lactobacillus reuteri, Lactobacillus rhamnosus, Streptococcus faecium, Streptococcus mutans, Streptococcus thermophilus, Saccharomyces boulardii, Torulopsia, Aspergillus oryzae*, and *Streptomyces* among others, including their vegetative spores, non-vegetative spores (*Bacillus*) and synthetic derivatives. More preferred probiotic microorganisms include, but are not limited to members of three bacterial genera: *Lactobacillus, Bifidobacterium* and *Saccharomyces*. In a preferred embodiment, the probiotic microorganism is *Lactobacillus, Bifidobacterium*, and a combination thereof The probiotic organism can be incorporated into the composition as a culture in water or another liquid or semisolid medium in which the probiotic remains viable. In another technique, a freeze-dried powder containing the probiotic organism may be incorporated into a particulate material or liquid or semi-solid material by mixing or blending.

In a preferred embodiment, the composition comprises a probiotic organism in an amount sufficient to delivery at least 1 to 200 billion viable probiotic organisms, preferably 1 to 100 billion, and most preferably 1 to 50 billion viable probiotic organisms. The amount of probiotic organisms delivery as describe above is may be per dosage and/or per day, where multiple dosages per day may be suitable for some applications. Two or more probiotic organisms may be used in a composition.

Methods to Obtain the Enzymatically-Produced Soluble α-Glucan Fiber Composition

Any number of common purification techniques may be used to obtain the present soluble α-glucan fiber composition from the reaction system including, but not limited to centrifugation, filtration, fractionation, chromatographic separation, dialysis, evaporation, precipitation, dilution or any combination thereof, preferably by dialysis or chromatographic separation, most preferably by dialysis (ultrafiltration).

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The enzyme(s) may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, the fungal host cell is *Trichoderma*, preferably a strain of *Trichoderma reesei*. In one embodiment, bacterial host strains include *Escherichia, Bacillus, Kluyveromyces*, and *Pseudomonas*. In a preferred embodiment, the bacterial host cell is *Bacillus subtilis* or *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters which are useful to drive expression of the present cephalosporin C deacetylase coding region in the desired host cell are numerous and familiar to those skilled in the art. Virtually any promoter capable of driving these genes is suitable for the present invention including but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived from the preferred host cell.

Industrial Production

A variety of culture methodologies may be applied to produce the enzyme(s). For example, large-scale production of a specific gene product over-expressed from a recombinant microbial host may be produced by batch, fed-batch, and continuous culture methodologies. Batch and fed-batch culturing methods are common and well known in the art and examples may be found in *Biotechnology: A Textbook of Industrial Microbiology* by Wulf Crueger and Anneliese Crueger (authors), Second Edition, (Sinauer Associates, Inc., Sunderland, Mass. (1990) and *Manual of Industrial Microbiology and Biotechnology*, Third Edition, Richard H. Baltz, Arnold L. Demain, and Julian E. Davis (Editors), (ASM Press, Washington, D.C. (2010).

Commercial production of the desired enzyme(s) may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired enzyme(s) from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst. Alternatively, the resulting partially-purified enzyme catalyst solution can be stabilized as a liquid formulation by the addition of polyols such as maltodextrin, sorbitol, or propylene glycol, to which is optionally added a preservative such as sorbic acid, sodium sorbate or sodium benzoate.

The production of the soluble α-glucan fiber can be carried out by combining the obtained enzyme(s) under any suitable aqueous reaction conditions which result in the production of the soluble α-glucan fiber such as the conditions disclosed herein. The reaction may be carried out in water solution, or, in certain embodiments, the reaction can be carried out in situ within a food product. Methods for producing a fiber using an enzyme catalyst in situ in a food product are known in the art. In certain embodiments, the enzyme catalyst is added to a sucrose-containing liquid food product. The enzyme catalyst can reduce the amount of sucrose in the liquid food product while increasing the amount of soluble α-glucan fiber and fructose. A suitable method for in situ production of fiber using a polypeptide material (i.e., an enzyme catalyst) within a food product can be found in WO2013/182686, the contents of which are herein incorporated by reference for the disclosure of a method for in situ production of fiber in a food product using an enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

Description of Certain Embodiments

In a first embodiment, a soluble α-glucan fiber composition is provided, said soluble α-glucan fiber composition comprising:

a. at least 95% α-(1,6) glycosidic linkages, preferably at least 96, 97, or at least 98%, α-(1,6) glycosidic linkages;
b. 1% or less α-(1,3) glycosidic linkages, preferably 0.9, 0.8, 0.7, 0.6, 0.5, 0.4, 0.3, 0.2, or 0.1% or less α-(1,3) glycosidic linkages;
c. less than 2% α-(1,3,6) glycosidic linkages, preferably 0.5% to less than 2%, more preferably 0.5% to 1.5% α-(1,3,6) glycosidic linkages;
d. less than 1.5% α-(1,4) glycosidic linkages, preferably 0.5% to less than 1.5%;
e. a weight average molecular weight of less than 20000 Daltons, preferably 500 Daltons to less than 20,000 Daltons, more preferably between 500 and 18,000 Daltons, and most preferably about 700 to about 18000 Daltons;
f. a viscosity of less than 0.25 Pascal second (Pa·s), preferably less than 0.01, 0.007, 0.005, 0.004, 0.003, 0.002 or 0.001 Pa·s at 12 wt % in water at 20° C.;
g. a dextrose equivalence (DE) in the range of 1 to 30;
h. a digestibility of less than 12%, preferably less than 11%, 10%, 9%, 8%, 7%, 6%, 5%, 4%, 3%, 2%, or 1% as measured by the Association of Analytical Communities (AOAC) method 2009.01;
i. a solubility of at least 20% (w/w), preferably at least 30%, 40%, 50%, 60%, or 70% in pH 7 water at 25° C.; and
j. a polydispersity index of less than 5, preferably a polydispersity index of less than 4, 3, 2, or 1.5.

In another embodiment to any of the above embodiments, the present soluble α-glucan fiber composition comprises less than 10%, preferably less than 9, 8, 7, 6, 5, 4, 3, 2 or 1% reducing sugars.

In another embodiment to any of the above embodiments, the soluble α-glucan fiber composition comprises less than 1.5% α-(1,4), preferably 0.5% to less than 1.5% glycosidic linkages.

In another embodiment to any of the above embodiments, the soluble α-glucan fiber composition is characterized by a number average molecular weight (Mn) between 400 and 2000 g/mol, preferably 500 to 1500 g/mol.

In one embodiment, a carbohydrate composition is provided comprising: 0.01 to 99 wt %, preferably 10 to 90 wt %, (dry solids basis) of the soluble α-glucan fiber composition of the first embodiment.

In another embodiment to any of the above embodiments, the carbohydrate composition further comprises: a monosaccharide, a disaccharide, glucose, sucrose, fructose, leucrose, corn syrup, high fructose corn syrup, isomerized sugar, maltose, trehalose, panose, raffinose, cellobiose, isomaltose, honey, maple sugar, a fruit-derived sweetener, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, a resistant maltodextrin, a branched maltodextrin, inulin, polydextrose, a fructooligosaccharide, a galactooligosaccharide, an isomaltooligosaccharide, a xylooligosaccharide, an arabinoxylooligosaccharide, a nigerooligosaccharide, a gentiooligosaccharide, a filler, an excipient, a binder or any combination thereof.

In another embodiment to any of the above embodiments, the carbohydrate composition is in the form of a liquid, a syrup, a powder, granules, shaped spheres, shaped sticks, shaped plates, shaped cubes, tablets, capsules, sachets, or any combination thereof.

In another embodiment, a food product, a personal care product, or pharmaceutical product is provided comprising the soluble α-glucan fiber composition of the first embodiment or a carbohydrate composition comprising the soluble α-glucan fiber composition of the first embodiment.

In another embodiment, a method to produce a soluble α-glucan fiber composition is provided comprising:
a. providing a set of reaction components comprising:
  i. sucrose; preferably at a concentration of at least 50 g/L, preferably at least 200 g/L;
  ii. at least one polypeptide having glucosyltransferase activity, said polypeptide comprising an amino acid sequence having at least 90% identity, preferably at least 91, 92, 93, 94, 95, 96, 97, 98, 99 or 100% identity to SEQ ID NO: 1, 3, 4 or 6; and
  iii. optionally one or more acceptors;
b. combining the set of reaction components under suitable aqueous reaction conditions whereby a product comprising a soluble α-glucan fiber composition is produced;
c. optionally isolating the soluble α-glucan fiber composition from the product of step (b); and
d. optionally concentrating the soluble α-glucan fiber composition.

In another embodiment of the method above, combining the set of reaction components under suitable aqueous reaction conditions comprises combining the set of reaction components within a food product.

A composition or method according to any of the above embodiments wherein the carbohydrate composition further comprises: monosaccharides, disaccharides, glucose, sucrose, fructose, leucrose, corn syrup, high fructose corn syrup, isomerized sugar, maltose, trehalose, panose, raffinose, cellobiose, isomaltose, honey, maple sugar, fruit-derived sweeteners, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, resistant maltodextrins, branched maltodextrins, inulin, polydextrose, fructooligosaccharides, galactooligosaccharides, isomaltooligosaccharides, xylooligosaccharides, arabinoxylooligosaccharides, nigerooligosaccharides, gentiooligosaccharides, hemicellulose, fructose oligomer syrup, fillers, excipients, binders, or any combination thereof.

A composition or method according to any of the above embodiments wherein the carbohydrate composition is in the form of a liquid, a syrup, a powder, granules, shaped spheres, shaped sticks, shaped plates, shaped cubes, tablets, powders, capsules, sachets, or any combination thereof.

A composition or method according to any of the above embodiments where the food product or food composition is:
  a. a bakery product selected from the group consisting of cakes, brownies, cookies, cookie crisps, muffins, breads, and sweet doughs, extruded cereal pieces, and coated cereal pieces;
  b. a dairy product selected from the group consisting of yogurt, yogurt drinks, milk drinks, flavored milks, smoothies, ice cream, shakes, cottage cheese, cottage cheese dressing, quarg, and whipped mousse-type products;
  c. confections selected from the group consisting of hard candies, fondants, nougats and marshmallows, gelatin jelly candies, gummies, jellies, chocolate, licorice, chewing gum, caramels, toffees, chews, mints, tableted confections, and fruit snacks;
  d. beverages selected from the group consisting of carbonated beverages, fruit juices, concentrated juice mixes, clear waters, and beverage dry mixes;
  e. high solids fillings for snack bars, toaster pastries, donuts, or cookies;
  f. extruded and sheeted snacks selected from the group consisting of puffed snacks, crackers, tortilla chips, and corn chips;
  g. snack bars, nutrition bars, granola bars, protein bars, and cereal bars;
  h. cheeses, cheese sauces, and other edible cheese products;
  i. edible films;
  j. water soluble soups, syrups, sauces, dressings, or coffee creamers; or
  k. dietary supplements; preferably in the form of tablets, powders, capsules or sachets.

A composition comprising 0.01 to 99 wt % (dry solids basis) of the present soluble α-glucan fiber composition and: a synbiotic, a peptide, a peptide hydrolysate, a protein, a protein hydrolysate, a soy protein, a dairy protein, an amino acid, a polyol, a polyphenol, a vitamin, a mineral, an herbal, an herbal extract, a fatty acid, a polyunsaturated fatty acid (PUFAs), a phytosteroid, betaine, a carotenoid, a digestive enzyme, a probiotic organism or any combination thereof.

Another embodiment is the use of the soluble α-glucan fiber composition in a food composition suitable for consumption by animals, including humans.

A method according to any of the above embodiments wherein the isolating step comprises centrifugation, filtration, fractionation, chromatographic separation, dialysis, evaporation, dilution or any combination thereof.

A method according to any of the above embodiments wherein the sucrose concentration is initially at least 200 g/L when the set of reaction components are combined.

A method according to any of the above embodiments wherein the suitable aqueous reaction conditions comprise a reaction temperature between 0° C. to 60° C., preferably 20° C. to 47° C.

A method according to any of the above embodiments wherein the suitable aqueous reaction conditions comprise a pH range of 3 to 8, preferably 4 to 8.

A method according to any of the above embodiments wherein the suitable aqueous reaction conditions comprise including a buffer selected from the group consisting of phosphate, pyrophosphate, bicarbonate, acetate, and citrate A method according to any of the above embodiments wherein said at least one glucosyltransferase is selected from the group consisting of SEQ ID NOs: 1, 3, 4, 6, and any combination thereof.

A product produced by any of the above process embodiments; preferably wherein the product produced is the soluble α-glucan fiber composition of the first embodiment.

EXAMPLES

Unless defined otherwise herein, all technical and scientific terms used herein have the same meaning as commonly understood by one of ordinary skill in the art to which this invention belongs. Singleton, et al., *DICTIONARY OF MICROBIOLOGY AND MOLECULAR BIOLOGY*, 2D ED., John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used in this invention.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "sec" or "s" means second(s), "ms" mean milliseconds, "min" means minute(s), "h" or "hr" means hour(s), "μL" means microliter(s), "mL" means milliliter(s), "L" means liter(s); "mL/min" is milliliters per minute; "μg/mL" is microgram(s) per milliliter(s); "LB" is Luria broth; "μm" is micrometers, "nm" is nanometers; "OD" is optical density; "IPTG" is isopropyl-β-D-thio-galactoside; "g" is gravitational force; "mM" is millimolar; "SDS-PAGE" is sodium dodecyl sulfate polyacrylamide; "mg/mL" is milligrams per milliliters; "N" is normal; "w/v" is weight for volume; "DTT" is dithiothreitol; "BCA" is bicinchoninic acid; "DMAc" is N, N'-dimethyl acetamide; "LiCl" is Lithium chloride' "NMR" is nuclear magnetic resonance; "DMSO" is dim ethylsulfoxide; "SEC" is size exclusion chromatography; "GI" or "gi"

means GenInfo Identifier, a system used by GENBANK® and other sequence databases to uniquely identify polynucleotide and/or polypeptide sequences within the respective databases; "DPx" means glucan degree of polymerization having "x" units in length; "ATCC" means American Type Culture Collection (Manassas, Va.), "DSMZ" and "DSM" will refer to Leibniz Institute DSMZ-German Collection of Microorganisms and Cell Cultures, (Braunschweig, Germany); "EELA" is the Finish Food Safety Authority (Helsinki, Finland;) CCUG" refer to the Culture Collection, University of Goteborg, Sweden; "Suc." means sucrose; "Gluc." means glucose; "Fruc." means fructose; "Leuc." means leucrose; and "Rxn" means reaction.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N Y (1984); and by Ausubel, F. M. et. al., *Short Protocols in Molecular Biology*, 5$^{th}$ Ed. *Current Protocols* and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., (American Society for Microbiology Press, Washington, D.C. (1994)), *Biotechnology: A Textbook of Industrial Microbiology* by Wulf Crueger and Anneliese Crueger (authors), Second Edition, (Sinauer Associates, Inc., Sunderland, Mass. (1990)), and *Manual of Industrial Microbiology and Biotechnology*, Third Edition, Richard H. Baltz, Arnold L. Demain, and Julian E. Davis (Editors), (American Society of Microbiology Press, Washington, D.C. (2010).

All reagents, restriction enzymes and materials used for the growth and maintenance of bacterial cells were obtained from BD Diagnostic Systems (Sparks, Md.), Invitrogen/Life Technologies Corp. (Carlsbad, Calif.), Life Technologies (Rockville, Md.), QIAGEN (Valencia, Calif.), Sigma-Aldrich Chemical Company (St. Louis, Mo.) or Pierce Chemical Co. (A division of Thermo Fisher Scientific Inc., Rockford, Ill.) unless otherwise specified. IPTG, (cat #16758) and triphenyltetrazolium chloride were obtained from the Sigma Co., (St. Louis, Mo.). Bellco spin flask was from the Bellco Co., (Vineland, N.J.). LB medium was from Becton, Dickinson and Company (Franklin Lakes, N.J.). BCA protein assay was from Sigma-Aldrich (St Louis, Mo.).

Growth of Recombinant *E. coli* Strains for Production of GTF Enzymes

*Escherichia coli* strains expressing a functional GTF enzyme were grown in shake flask using LB medium with ampicillin (100 µg/mL) at 37° C. and 220 rpm to $OD_{600nm}$=0.4-0.5, at which time isopropyl-β-D-thio-galactoside (IPTG) was added to a final concentration of 0.5 mM and incubation continued for 2-4 hr at 37° C. Cells were harvested by centrifugation at 5,000×g for 15 min and resuspended (20%-25% wet cell weight/v) in 50 mM phosphate buffer pH 7.0). Resuspended cells were passed through a French Pressure Cell (SLM Instruments, Rochester, N.Y.) twice to ensure >95% cell lysis. Cell lysate was centrifuged for 30 min at 12,000×g and 4° C. The resulting supernatant (cell extract) was analyzed by the BCA protein assay and SDS-PAGE to confirm expression of the GTF enzyme, and the cell extract was stored at −80° C.

pHYT Vector

The pHYT vector backbone is a replicative *Bacillus subtilis* expression plasmid containing the *Bacillus subtilis* aprE promoter. It was derived from the *Escherichia coli-Bacillus subtilis* shuttle vector pHY320PLK (GENBANK® Accession No. D00946 and is commercially available from Takara Bio Inc. (Otsu, Japan)). The replication origin for *Escherichia coli* and ampicillin resistance gene are from pACYC177 (GENBANK® X06402 and is commercially available from New England Biolabs Inc., Ipswich, Mass.). The replication origin for *Bacillus subtilis* and tetracycline resistance gene were from pAMalpha-1 (Francia et al., *J Bacteriol*. 2002 September; 184(18):5187-93)).

To construct pHYT, a terminator sequence: 5'-ATAAAAAACGCTCGGTTGCCGCCGGGCGTTTTT-TAT-3' (SEQ ID NO: 8) from phage lambda was inserted after the tetracycline resistance gene. The entire expression cassette (EcoRI-BamHI fragment) containing the aprE promoter—AprE signal peptide sequence-coding sequence encoding the enzyme of interest (e.g., coding sequences for various GTFs)—BPN' terminator was cloned into the EcoRI and HindIII sites of pHYT using a BamHI-HindIII linker that destroyed the HindIII site. The linker sequence is 5'-GGATCCTGACTGCCTGAGCTT-3' (SEQ ID NO: 9). The aprE promoter and AprE signal peptide sequence (SEQ ID NO: 7) are native to *Bacillus subtilis*. The BPN' terminator is from subtilisin of *Bacillus amyloliquefaciens*. In the case when native signal peptide was used, the AprE signal peptide was replaced with the native signal peptide of the expressed gene.

Biolistic Transformation Method for *T. reesei*

A *Trichoderma reesei* spore suspension is spread onto the center ~6 cm diameter of an acetamidase transformation plate (150 µL of a $5\times10^7$-$5\times10^8$ spore/mL suspension). The plate is then air dried in a biological hood. The stopping screens (BioRad 165-2336) and the macrocarrier holders (BioRad 1652322) are soaked in 70% ethanol and air dried. DRIERITE® desiccant (calcium sulfate desiccant; W. A. Hammond DRIERITE® Company, Xenia, Ohio) is placed in small Petri dishes (6 cm Pyrex) and overlaid with Whatman filter paper (GE Healthcare Bio-Sciences, Pittsburgh, Pa.). The macrocarrier holder containing the macrocarrier (BioRad 165-2335; Bio-Rad Laboratories, Hercules, Calif.) are placed flatly on top of the filter paper and the Petri dish lid replaced. A tungsten particle suspension is prepared by adding 60 mg tungsten M-10 particles (microcarrier, 0.7 micron, BioRad #1652266, Bio-Rad Laboratories) to an Eppendorf tube. Ethanol (1 mL) (100%) was added. The tungsten is vortexed in the ethanol solution and allowed to soak for 15 minutes. The Eppendorf tube is microfuged briefly at maximum speed to pellet the tungsten. The ethanol is decanted and washed three times with sterile distilled water. After the water wash is decanted the third time, the tungsten is resuspended in 1 mL of sterile 50% glycerol. The transformation reaction is prepared by adding 25 µL suspended tungsten to a 1.5 mL-Eppendorf tube for each transformation. Subsequent additions are made in order, 2 µL DNA pTrex3 expression vectors (SEQ ID NO: 10; see U.S. Pat. No. 6,426,410), 25 µL 2.5M $CaCl_2$, 10 µL 0.1M spermidine. The reaction is vortexed continuously for 5-10 minutes, keeping the tungsten suspended. The Eppendorf tube is then microfuged briefly and decanted. The tungsten pellet is washed with 200 μL of 70% ethanol, microfuged briefly to pellet and decanted. The pellet is washed with 200 μL of 100% ethanol, microfuged briefly to pellet, and decanted. The tungsten pellet is resuspended in 24 μL 100% ethanol. The Eppendorf tube is placed in an ultrasonic water bath for 15 seconds and 8 μL aliquots are transferred onto the center of the desiccated macrocarriers. The macrocarriers are left to dry in the desiccated Petri dishes.

A Helium tank is turned on to 1500 psi (~10.3 MPa). 1100 psi (~7.58 MPa) rupture discs (BioRad 165-2329) are used in the Model PDS-1000/He™ BIOLISTIC® Particle Delivery System (BioRad). When the tungsten solution is dry, a stopping screen and the macrocarrier holder are inserted into the PDS-1000. An acetamidase plate, containing the target *T. reesei* spores, is placed 6 cm below the stopping screen. A vacuum of 29 inches Hg (~98.2 kPa) is pulled on the chamber and held. The He BIOLISTIC® Particle Delivery System is fired. The chamber is vented and the acetamidase plate removed for incubation at 28° C. until colonies appeared (5 days).

Modified amdS Biolistic Agar (MABA) Per Liter
    Part I, make in 500 mL distilled water ($dH_2O$)
        1000× salts 1 mL
        Noble agar 20 g
        pH to 6.0, autoclave
    Part II, make in 500 mL $dH_2O$
        Acetamide 0.6 g
        CsCl 1.68 g
        Glucose 20 g
        $KH_2PO_4$ 15 g
        $MgSO_4.7H_2O$ 0.6 g
        $CaCl_2.2H_2O$ 0.6 g
    pH to 4.5, 0.2 micron filter sterilize; leave in 50° C. oven to warm, add to agar, mix, pour plates. Stored at room temperature (~21° C.)
1000× Salts per liter
    $FeSO_4.7H_2O$ 5 g
    $MnSO_4.H_2O$ 1.6 g
    $ZnSO_4.7H_2O$ 1.4 g
    $CoCl_2.6H_2O$ 1 g
    Bring up to 1 L $dH_2O$.
    0.2 micron filter sterilize Determination of the Glucosyltransferase Activity Glucosyltransferase activity assay was performed by incubating 1-10% (v/v) crude protein extract containing GTF enzyme with 200 g/L sucrose in 25 mM or 50 mM sodium acetate buffer at pH 5.5 in the presence or absence of 25 g/L dextran (MW ~1500, Sigma-Aldrich, Cat.#31394) at 37° C. and 125 rpm orbital shaking. One aliquot of reaction mixture was withdrawn at 1 h, 2 h and 3 h and heated at 90° C. for 5 min to inactivate the GTF. The insoluble material was removed by centrifugation at 13,000×g for 5 min, followed by filtration through 0.2 μm RC (regenerated cellulose) membrane. The resulting filtrate was analyzed by HPLC using two Aminex HPX-87C columns series at 85° C. (Bio-Rad, Hercules, Calif.) to quantify sucrose concentration. The sucrose concentration at each time point was plotted against the reaction time and the initial reaction rate was determined from the slope of the linear plot. One unit of GTF activity was defined as the amount of enzyme needed to consume one micromole of sucrose in one minute under the assay condition.

Determination of the α-Glucanohydrolase Activity

Insoluble mutan polymers required for determining mutanase activity were prepared using secreted enzymes produced by *Streptococcus sobrinus* ATCC® 33478™. Specifically, one loop of glycerol stock of *S. sobrinus* ATCC® 33478™ was streaked on a BHI agar plate (Brain Heart Infusion agar, Teknova, Hollister, Calif.), and the plate was incubated at 37° C. for 2 days; A few colonies were picked using a loop to inoculate 2×100 mL BHI liquid medium in the original medium bottle from Teknova, and the culture was incubated at 37° C., static for 24 h. The resulting cells were removed by centrifugation and the resulting supernatant was filtered through 0.2 μm sterile filter; 2×101 mL of filtrate was collected. To the filtrate was added 2×11.2 mL of 200 g/L sucrose (final sucrose 20 g/L). The reaction was incubated at 37° C., with no agitation for 67 h. The resulting polysaccharide polymers were collected by centrifugation at 5000×g for 10 min. The supernatant was carefully decanted. The insoluble polymers were washed 4 times with 40 mL of sterile water. The resulting mutan polymers were lyophilized for 48 h. Mutan polymer (390 mg) was suspended in 39 mL of sterile water to make suspension of 10 mg/mL. The mutan suspension was homogenized by sonication (40% amplitude until large lumps disappear, ~10 min in total). The homogenized suspension was aliquoted and stored at 4° C.

A mutanase assay was initiated by incubating an appropriate amount of enzyme with 0.5 mg/mL mutan polymer (prepared as described above) in 25 mM KOAc buffer at pH 5.5 and 37° C. At various time points, an aliquot of reaction mixture was withdrawn and quenched with equal volume of 100 mM glycine buffer (pH 10). The insoluble material in each quenched sample was removed by centrifugation at 14,000×g for 5 min. The reducing ends of oligosaccharide and polysaccharide polymer produced at each time point were quantified by the p-hydroxybenzoic acid hydrazide solution (PAHBAH) assay (Lever M., *Anal. Biochem.*, (1972) 47:273-279) and the initial rate was determined from the slope of the linear plot of the first three or four time points of the time course. The PAHBAH assay was performed by adding 10 μL of reaction sample supernatant to 100 μL of PAHBAH working solution and heated at 95° C. for 5 min. The working solution was prepared by mixing one part of reagent A (0.05 g/mL p-hydroxy benzoic acid hydrazide and 5% by volume of concentrated hydrochloric acid) and four parts of reagent B (0.05 g/mL NaOH, 0.2 g/mL sodium potassium tartrate). The absorption at 410 nm was recorded and the concentration of the reducing ends was calculated by subtracting appropriate background absorption and using a standard curve generated with various concentrations of glucose as standards.

Determination of Glycosidic Linkages

One-dimensional $^1H$ NMR data were acquired on a Varian Unity Inova system (Agilent Technologies, Santa Clara, Calif.) operating at 500 MHz using a high sensitivity cryoprobe. Water suppression was obtained by carefully placing the observe transmitter frequency on resonance for the residual water signal in a "presat" experiment, and then using the "tnnoesy" experiment with a full phase cycle (multiple of 32) and a mix time of 10 ms.

Typically, dried samples were taken up in 1.0 mL of $D_2O$ and sonicated for 30 min. From the soluble portion of the sample, 100ł was added to a 5 mm NMR tube along with 350ł $D_2O$ and 100ł of $D_2O$ containing 15.3 mM DSS (4,4-dimethyl-4-silapentane-1-sulfonic acid sodium salt) as internal reference and 0.29% $NaN_3$ as bactericide. The abundance of each type of anomeric linkage was measured by the integrating the peak area at the corresponding chemical shift. The percentage of each type of anomeric linkage was calculated from the abundance of the particular linkage and the total abundance anomeric linkages from oligosaccharides.

Methylation Analysis

The distribution of glucosidic linkages in glucans was determined by a well-known technique generally named "methylation analysis," or "partial methylation analysis" (see: F. A. Pettolino, et al., Nature Protocols, (2012) 7(9): 1590-1607). The technique has a number of minor variations but always includes: 1. methylation of all free hydroxyl groups of the glucose units, 2. hydrolysis of the methylated glucan to individual monomer units, 3. reductive ring-opening to eliminate anomers and create methylated glucitols; the anomeric carbon is typically tagged with a deuterium atom to create distinctive mass spectra, 4. acetylation of the free hydroxyl groups (created by hydrolysis and ring opening) to create partially methylated glucitol acetates, also known as partially methylated products, 5. analysis of the resulting partially methylated products by gas chromatography coupled to mass spectrometry and/or flame ionization detection.

The partially methylated products include non-reducing terminal glucose units, linked units and branching points. The individual products are identified by retention time and mass spectrometry. The distribution of the partially-methylated products is the percentage (area %) of each product in the total peak area of all partially methylated products. The gas chromatographic conditions were as follows: RTx-225 column (30 m×250 µm ID×0.1 µm film thickness, Restek Corporation, Bellefonte, Pa., USA), helium carrier gas (0.9 mL/min constant flow rate), oven temperature program starting at 80° C. (hold for 2 min) then 30° C./min to 170° C. (hold for 0 min) then 4° C./min to 240° C. (hold for 25 min), 1 µL injection volume (split 5:1), detection using electron impact mass spectrometry (full scan mode)

Viscosity Measurement

The viscosity of 12 wt % aqueous solutions of soluble fiber was measured using a TA Instruments AR-G2 controlled-stress rotational rheometer (TA Instruments—Waters, LLC, New Castle, Del.) equipped with a cone and plate geometry. The geometry consists of a 40 mm 2° upper cone and a peltier lower plate, both with smooth surfaces. An environmental chamber equipped with a water-saturated sponge was used to minimize solvent (water) evaporation during the test. The viscosity was measured at 20° C. The peltier was set to the desired temperature and 0.65 mL of sample was loaded onto the plate using an Eppendorf pipette (Eppendorf North America, Hauppauge, N.Y.). The cone was lowered to a gap of 50 µm between the bottom of the cone and the plate. The sample was thermally equilibrated for 3 minutes. A shear rate sweep was performed over a shear rate range of 500-10 s$^{-1}$. Sample stability was confirmed by running repeat shear rate points at the end of the test.

Determination of the Concentration of Sucrose, Glucose, Fructose and Leucrose

Sucrose, glucose, fructose, and leucrose were quantitated by HPLC with two tandem Aminex HPX-87C Columns (Bio-Rad, Hercules, Calif.). Chromatographic conditions used were 85° C. at column and detector compartments, 40° C. at sample and injector compartment, flow rate of 0.6 mL/min, and injection volume of 10 µL. Software packages used for data reduction were EMPOWER™ version 3 from Waters (Waters Corp., Milford, Mass.). Calibrations were performed with various concentrations of standards for each individual sugar.

Determination of the Concentration of Oligosaccharides

Soluble oligosaccharides were quantitated by HPLC with two tandem Aminex HPX-42A columns (Bio-Rad). Chromatographic conditions used were 85° C. column temperature and 40° C. detector temperature, water as mobile phase (flow rate of 0.6 mL/min), and injection volume of 10 µL. Software package used for data reduction was EMPOWER™ version 3 from Waters Corp. Oligosaccharide samples from DP2 to DP7 were obtained from Sigma-Aldrich: maltoheptaose (DP7, Cat.#47872), maltohexanose (DP6, Cat.#47873), maltopentose (DP5, Cat.#47876), maltotetraose (DP4, Cat.#47877), isomaltotriose (DP3, Cat.#47884) and maltose (DP2, Cat.#47288). Calibration was performed for each individual oligosaccharide with various concentrations of the standard.

Determination of Digestibility

The digestibility test protocol was adapted from the Megazyme Integrated Total Dietary Fiber Assay (AOAC method 2009.01, Ireland). The final enzyme concentrations were kept the same as the AOAC method: 50 Unit/mL of pancreatic α-amylase (PAA), 3.4 Units/mL for amyloglucosidase (AMG). The substrate concentration in each reaction was 25 mg/mL as recommended by the AOAC method. The total volume for each reaction was 1 mL instead of 40 mL as suggested by the original protocol. Every sample was analyzed in duplicate with and without the treatment of the two digestive enzymes. The detailed procedure is described below:

The enzyme stock solution was prepared by dissolving 20 mg of purified porcine pancreatic α-amylase (150,000 Units/g; AOAC Method 2002.01) from the Integrated Total Dietary Fiber Assay Kit in 29 mL of sodium maleate buffer (50 mM, pH 6.0 plus 2 mM $CaCl_2$) and stir for 5 min, followed by the addition of 60 uL amyloglucosidase solution (AMG, 3300 Units/mL) from the same kit. 0.5 mL of the enzyme stock solution was then mixed with 0.5 mL soluble fiber sample (50 mg/mL) in a glass vial and the digestion reaction mixture was incubated at 37° C. and 150 rpm in orbital motion in a shaking incubator for exactly 16 h. Duplicated reactions were performed in parallel for each fiber sample. The control reactions were performed in duplicate by mixing 0.5 mL maleate buffer (50 mM, pH 6.0 plus 2 mM $CaCl_2$) and 0.5 mL soluble fiber sample (50 mg/mL) and reaction mixtures was incubated at 37° C. and 150 rpm in orbital motion in a shaking incubator for exactly 16 h. After 16 h, all samples were removed from the incubator and immediately 75 µL of 0.75 M TRIZMA® base solution was added to terminate the reaction. The vials were immediately placed in a heating block at 95-100° C., and incubate for 20 min with occasional shaking (by hand). The total volume of each reaction mixture is 1.075 mL after quenching. The amount of released glucose in each reaction was quantified by HPLC with the Aminex HPX-87C Columns (BioRad) as described in the General Methods. Maltodextrin (DE4-7, Sigma) was used as the positive control for the enzymes. To calculate the digestibility, the following formula was used:

Digestibility=100%*[amount of glucose (mg) released after treatment with enzyme−amount of glucose (mg) released in the absence of enzyme]/1.1*amount of total fiber (mg)"

Purification of Soluble Oligosaccharide Fiber

Soluble oligosaccharide fiber present in product mixtures produced by the conversion of sucrose using glucosyltransferase enzymes with or without added mutanases as described in the following examples were purified and isolated by size-exclusion column chromatography (SEC). In a typical procedure, product mixtures were heat-treated at 60° C. to 90° C. for between 15 min and 30 min and then centrifuged at 4000 rpm for 10 min. The resulting supernatant was injected onto an ÄKTAprime purification system (SEC; GE Healthcare Life Sciences) (10 mL-50 mL injection volume) connected to a GE HK 50/60 column packed with 1.1 L of Bio-Gel P2 Gel (Bio-Rad, Fine 45-90 μm) using water as eluent at 0.7 mL/min. The SEC fractions (~5 mL per tube) were analyzed by HPLC for oligosaccharides using a Bio-Rad HPX-47A column. Fractions containing >DP2 oligosaccharides were combined and the soluble fiber isolated by rotary evaporation of the combined fractions to produce a solution containing between 3% and 6% (w/w) solids, where the resulting solution was lyophilized to produce the soluble fiber as a solid product.

Pure Culture Growth on Specific Carbon Sources

To test the capability of microorganisms to grow on specific carbon sources (oligosaccharide or polysaccharide soluble fibers), selected microbes were grown in appropriate media free from carbon sources other than the ones under study. Growth was evaluated by regular (every 30 min) measurement of optical density at 600 nm in an anaerobic environment (80% $N_2$, 10% $CO_2$, 10% $H_2$). Growth was expressed as area under the curve and compared to a positive control (glucose) and a negative control (no added carbon source).

Stock solutions of oligosaccharide soluble fibers (10% w/w) were prepared in demineralised water. The solutions were either sterilised by UV radiation or filtration (0.2 μm). Stocks were stored frozen until used. Appropriate carbon source-free medium was prepared from single ingredients. Test organisms were pre-grown anaerobically in the test medium with the standard carbon source. In honeycomb wells, 20 μL of stock solution was pipetted and 180 μL carbon source-free medium with 1% test microbe was added. As positive control, glucose was used as carbon source, and as negative control, no carbon source was used. To confirm sterility of the stock solutions, uninocculated wells were used. At least three parallel wells were used per run.

The honeycomb plates were placed in a Bioscreen and growth was determined by measuring absorbance at 600 nm. Measurements were taken every 30 min and before measurements, the plates were shaken to assure an even suspension of the microbes. Growth was followed for 24 h. Results were calculated as area under the curve (i.e., $OD_{600}$/24 h). Organisms tested (and their respective growth medium) were: *Clostridium perfringens* ATCC® 3626™ (anaerobic Reinforced Clostridial Medium (from Oxoid Microbiology Products, ThermoScientific) without glucose), *Clostridium difficile* DSM 1296 (Deutsche Sammlung von Mikroorganismen and Zellkulturen DSMZ, Braunschweig, Germany) (anaerobic Reinforced Clostridial Medium (from Oxoid Microbiology Products, Thermo Fisher Scientific Inc., Waltham, Mass.) without glucose), *Escherichia coli* ATCC® 11775™ (anaerobic Trypticase Soy Broth without glucose), *Salmonella typhimurium* EELA (available from DSMZ, Brauchschweig, Germany) (anaerobic Trypticase Soy Broth without glucose), *Lactobacillus acidophilus* NCFM 145 (anaerobic de Man, Rogosa and Sharpe Medium (from DSMZ) without glucose), *Bifidobacterium animalis* subsp. *Lactis* Bi-07 (anaerobic Deutsche Sammlung vom Mikroorgnismen and Zellkulturen medium 58 (from DSMZ), without glucose).

In Vitro Gas Production

To measure the formation of gas by the intestinal microbiota, a pre-conditioned faecal slurry was incubated with test prebiotic (oligosaccharide or polysaccharide soluble fibers) and the volume of gas formed was measured. Fresh faecal material was pre-conditioned by dilution with 3 parts (w/v) of anaerobic simulator medium, stirring for 1 h under anaerobic conditions and filtering through 0.3-mm metal mesh after which it was incubated anaerobically for 24 h at 37° C.

The simulator medium used was composed as described by G. T. Macfarlane et al. (*Microb. Ecol.* 35(2):180-7 (1998)) containing the following constituents (g/L) in distilled water: starch (BDH Ltd.), 5.0; peptone, 0.05; tryptone, 5.0; yeast extract, 5.0; NaCl, 4.5; KCl, 4.5; mucin (porcine gastric type III), 4.0; casein (BDH Ltd.), 3.0; pectin (citrus), 2.0; xylan (oatspelt), 2.0; arabinogalactan (larch wood), 2.0; $NaHCO_3$, 1.5; $MgSO_4$, 1.25; guar gum, 1.0; inulin, 1.0; cysteine, 0.8; $KH_2PO_4$, 0.5; $K_2HPO_4$, 0.5; bile salts No. 3, 0.4; $CaCl_2 \times 6 \, H_2O$, 0.15; $FeSO_4 \times 7 \, H_2O$, 0.005; hemin, 0.05; and Tween 80, 1.0; cysteine hydrochloride, 6.3; $Na_2S \times 9H_2O$, and 0.1% resazurin as an indication of sustained anaerobic conditions. The simulation medium was filtered through 0.3 mm metal mesh and divided into sealed serum bottles.

Test prebiotics were added from 10% (w/w) stock solutions to a final concentration of 1%. The incubation was performed at 37° C. while maintaining anaerobic conditions. Gas production due to microbial activity was measured manually after 24 h incubation using a scaled, airtight glass syringe, thereby also releasing the overpressure from the simulation unit.

Example 1

Expression of *Lactobacillus animalis* KCTC 3501 Glucosyltransferase LanGtf1

A glucosyltransferase gene, LanGtf1, from *Lactobacillus animalis* KCTC 3501 was identified in GENBANK® gi:335358117 (SEQ ID NO: 1). LanGtf1 protein (GTF8117) has a 37 amino acid signal peptide predicted by SignalP4.0 (Thomas Nordahl Petersen et al., *Nature Methods*, 8:785-786, 2011) indicating that LanGtf1 is a secreted protein. Gene sequence encoding the mature protein of LanGtf1 (SEQ ID NO: 3) was optimized for expression in *Bacillus subtilis*. The genes were synthesized by Generay (Shanghai, China), and inserted into the p2JM103BBI plasmid (Vogtentanz et al., *Protein Expr Purif*, (2007) 55:40-52), resulting in pZZH561 plasmid. pZZHB561 contains an aprE promoter, an AprE signal sequence (SEQ ID NO: 7) used to direct protein secretion in *Bacillus subtilis*, an oligonucleotide that encodes a short linker sequence (SEQ ID NO: 11) to facilitate the secretion of the target protein, and the synthetic gene (SEQ ID NO: 2) encoding the target protein (SEQ ID NO: 12).

The plasmid pZZHB561 was used to transform *B. subtilis* BG6006 cells. The *B. subtilis* host BG6006 strain contains 9 protease deletions (amyE::xylRPxylAcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB). The transformed cells of SG1115 were spread on Luria Agar plates supplemented with 5 ppm chloramphenicol. The colony was grown in LB containing 5 ug/mL chloramphenicol for 6-8 hours, and then subcultured into GrantsII medium containing 5 ug/mL chloramphenicol grown at 37° C. for 2-3 days. The cultures were spun at 15,000×g for 30 min at 4° C. and the supernatant was filtered through 0.22 um filters. The filtered supernatant containing mature glucosyl transferase GTF8117 (with signal peptide removed; SEQ ID NO: 3) was aliquoted and frozen at −80° C.

The optimized nucleotide sequence of LanGtf1 gene encoding the mature protein in the plasmid pZZHB561 is set forth below as SEQ ID NO: 2.

Example 2

Expression of *Streptococcus salivarius* M18 Glucosyltransferase

SG1031 is a *Bacillus subtilis* expression strain that expresses the glycosyltransferase GTF6831 (GENBANK® gi: 345526831; SEQ ID NO: 4) from *Streptococcus salivarius* M18. The *B. subtilis* host BG6006 strain contains 9 protease deletions (amyE::xylRPxylAcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB). The full length GTF6831 has 1600 amino acids (SEQ ID NO: 4). The coding sequence (SEQ ID NO: 5) for the 1558 amino acid mature protein (SEQ ID NO: 6) without the putative signal peptide was synthesized by GenScript and fused with the *B. subtilis* AprE signal peptide (SEQ ID NO: 7) by cloning into the NheI and HindIII sites of the replicative *Bacillus* pHYT expression vector under the aprE promoter. The AprE-GTF6831 sequence is provided as SEQ ID NO: 13. The construct was first transformed into *E. coli* DH10B and selected on LB with ampicillin (100 ug/mL) plates. The confirmed construct pDCQ931 expressing GTF6831 was then transformed into *B. subtilis* BG6006 and selected on the LB plates with tetracycline (12.5 ug/mL). The resulted *B. subtilis* expression strain SG1031 was purified and used as the source of the GTF6831 enzyme. SG1031 strain was grown in LB containing 10 ug/mL tetracycline first, and then subcultured into GrantsII medium containing 12.5 ug/mL tetracycline grown at 37° C. for 2-3 days. The cultures were spun at 15,000×g for 30 min at 4° C. and the supernatant was filtered through 0.22 um filters. The filtered supernatant containing GTF6831 (SEQ ID NO: x) was aliquoted and frozen at −80° C.

Example 3

Isolation of Soluble Fiber Produced by GTF8117

A 200-mL reaction containing 200 g/L sucrose and *B. subtilis* crude protein supernatant (5% v/v) containing mature glycosyltransferase GTF8117 from *Lactobacillus animalis* KCTC 3501 (GENBANK® GI: 335358117; Example 1) in distilled, deionized H$_2$O, was stirred at 30° C. for 44 h, then heated to 60° C. for 30 min to inactivate the enzyme. The resulting product mixture was centrifuged and the supernatant analyzed by HPLC for soluble monosaccharides, disaccharides and oligosaccharides, then the entire supernatant was purified by SEC using BioGel P2 resin (BioRad). The SEC fractions that contained oligosaccharides ≥DP3 were combined and concentrated by rotary evaporation for analysis by HPLC (Table 1).

TABLE 1

Soluble oligosaccharide fiber produced by GTF8117.
200 g/L sucrose, GT 8117, 30° C., 44 h

|  | Product mixture, g/L | SEC-purified product, g/L |
|---|---|---|
| ≥DP8 | 90.6 | 148.1 |
| DP7 | 0 | 0 |
| DP6 | 0 | 0 |
| DP5 | 0 | 0 |
| DP4 | 0 | 0 |
| DP3 | 0 | 0 |
| DP2 | 1.8 | 0 |
| Sucrose | 0.6 | 0 |
| Leucrose | 7.5 | 0 |
| Glucose | 1.8 | 0 |
| Fructose | 97.2 | 0 |
| Sum DP2-≥DP8 | 92.4 | 148.1 |
| Sum DP3-≥DP8 | 90.6 | 148.1 |

Example 4

Isolation of Soluble Fiber Produced by GTF8117

A 300-mL reaction containing 200 g/L sucrose and *B. subtilis* crude protein supernatant (10% v/v) containing mature glycosyltransferase GTF8117 from *Lactobacillus animalis* KCTC 3501 (GI: 335358117; Example 1) in distilled, deionized H$_2$O was stirred at 37° C. for 40 h, then heated to 60° C. for 30 min to inactivate the enzyme. The resulting product mixture was centrifuged and the resulting supernatant analyzed by HPLC for soluble monosaccharides, disaccharides and oligosaccharides, then the entire supernatant was purified by SEC using BioGel P2 resin (BioRad). The SEC fractions that contained oligosaccharides ≥DP3 were combined and concentrated by rotary evaporation for analysis by HPLC (Table 2). The concentrate was lyophilized to produce the soluble fiber as a dry solid.

TABLE 2

Soluble oligosaccharide fiber produced by GTF8117.
200 g/L sucrose, GT 8117, 37° C., 40 h

|  | Product mixture, g/L | SEC-purified product, g/L |
|---|---|---|
| ≥DP8 | 78.7 | 98.1 |
| DP7 | 0 | 0 |
| DP6 | 0 | 0 |
| DP5 | 0 | 0 |
| DP4 | 0 | 0 |
| DP3 | 0 | 0 |
| DP2 | 1.7 | 0 |
| Sucrose | 0.5 | 0 |
| Leucrose | 5.0 | 0.2 |
| Glucose | 8.1 | 0.6 |
| Fructose | 90.4 | 1.6 |
| Sum DP2-≥DP8 | 80.4 | 98.1 |
| Sum DP3-≥DP8 | 78.7 | 98.1 |

Example 5

Isolation of Soluble Fiber Produced by GTF6831

A 200-mL reaction containing 200 g/L sucrose and *B. subtilis* crude protein supernatant (10% v/v) containing glycosyltransferase GTF6831 from *Streptococcus salivarius* M18 (GI: 345526831; Example 2) in distilled, deionized H$_2$O, was stirred at 30° C. for 20 h, then heated to 60° C. for 30 min to inactivate the enzyme. The resulting product mixture was centrifuged and the resulting supernatant analyzed by HPLC for soluble monosaccharides, disaccharides and oligosaccharides, then the entire supernatant was purified by SEC using BioGel P2 resin (BioRad). The SEC fractions that contained oligosaccharides ≥DP3 were combined and concentrated by rotary evaporation for analysis by HPLC (Table 3).

TABLE 3

Soluble oligosaccharide fiber produced by GTF6831. 200 g/L sucrose, GTF6831, 30° C., 20 h

|  | Product mixture, g/L | SEC-purified product, g/L |
|---|---|---|
| ≥DP8 | 94.6 | 70.2 |
| DP7 | 0 | 1.1 |
| DP6 | 0.7 | 1.1 |
| DP5 | 0.5 | 1.4 |
| DP4 | 0.4 | 1.7 |
| DP3 | 0 | 3.5 |
| DP2 | 1.3 | 2.1 |
| Sucrose | 0.3 | 2.0 |
| Leucrose | 9.0 | 0 |
| Glucose | 8.8 | 0 |
| Fructose | 82.1 | 0 |
| Sum DP2-≥DP8 | 97.5 | 81.1 |
| Sum DP3-≥DP8 | 96.2 | 79.0 |

Example 6

Isolation of Soluble Fiber Produced by GTF6831

A 1000-mL reaction mixture containing 100 g/L sucrose and *B. subtilis* crude protein supernatant (10% v/v) containing glycosyltransferase GTF6831 from *Streptococcus salivarius* M18 (GI: 345526831; Example 2) in distilled, deionized H$_2$O was sterile filtered (0.22 um) and the filtrate divided equally among three 1-liter sterile flasks. The flasks were shaken at 125 rpm at 37° C. for 20 h, then heated to 60° C. for 30 min to inactivate the enzyme. The resulting product mixtures were centrifuged and the resulting supernatants analyzed by HPLC for soluble monosaccharides, disaccharides and oligosaccharides, then the combined supernatants were concentrated to 450 mL total volume by rotary evaporation. The concentrate was purified by ultrafiltration using a 10 kDa molecular weight cutoff polyethersulfone (PES) membrane (Pall Centramate™ LV), and the retentate concentrated by rotary evaporation for analysis by HPLC (Table 4). The concentrated retentate was lyophilized to produce the soluble fiber as a dry solid.

TABLE 4

Soluble oligosaccharide fiber produced by GTF6831.

100 g/L sucrose, GTF6831, 37° C., 20 h

|  | Product mixture 1, g/L | Product mixture 2, g/L | Product mixture 3, g/L | UF-purified product, g/L |
|---|---|---|---|---|
| ≥DP8 | 43.4 | 43.6 | 43.7 | 104.5 |
| DP7 | 0 | 0 | 0 | 0 |
| DP6 | 0 | 0 | 0 | 0 |
| DP5 | 0 | 0 | 0 | 0 |
| DP4 | 0 | 0 | 0 | 0 |
| DP3 | 0 | 0 | 0 | 0 |
| DP2 | 0 | 0 | 0 | 0 |
| Sucrose | 0.6 | 0.3 | 0.3 | 0 |
| Leucrose | 3.2 | 2.7 | 2.7 | 0.1 |
| Glucose | 7.1 | 7.3 | 7.2 | 0.1 |
| Fructose | 43.9 | 43.4 | 43.4 | 0.1 |
| Sum DP2-≥DP8 | 43.4 | 43.6 | 43.7 | 104.5 |
| Sum DP3-≥DP8 | 43.4 | 43.6 | 43.7 | 104.5 |

Example 7

Anomeric Linkage Analysis of Soluble Fiber Produced by GTF8117 or GTF6831

Solutions of soluble fibers purified by chromatography or by ultrafiltration prepared as described in Examples 4 and Example 6 were dried to a constant weight by lyophilization, and the resulting solids analyzed by $^1$H NMR spectroscopy and by GC/MS as described in the General Methods section (above). The anomeric linkages for each of these soluble oligosaccharide fiber mixtures are reported in Tables 5 and 6.

TABLE 5

Anomeric linkage analysis of soluble oligosaccharides by $^1$H NMR spectroscopy.

| Example # | GTF | % α-(1, 3) | % α-(1, 2) | % α-(1, 3, 6) | % α-(1, 2, 6) | % α-(1, 6) |
|---|---|---|---|---|---|---|
| 70 | GTF8117 | 0 | 0 | 0 | 0 | 100 |
| 72 | GTF6831 | 0 | 0 | 0 | 0 | 100 |

TABLE 6

Anomeric linkage analysis of soluble oligosaccharides by GC/MS.

| Example # | GTF | % α-(1, 4) | % α-(1, 3) | % α-(1, 3, 6) | % 2,1 Fruc | % α-(1, 2) | % α-(1, 6) | % α-(1, 3, 4) | % α-(1, 2, 3) | % α-(1, 4, 6) + α-(1, 2, 6) |
|---|---|---|---|---|---|---|---|---|---|---|
| 70 | GTF8117 | 1.1 | 0.7 | 1.3 | 0.2 | 0.5 | 95 | 0 | 0 | 1.3 |
| 72 | GTF6831 | 0.4 | 0 | 1.3 | 0 | 0.2 | 97 | 0 | 0 | 1.1 |

Example 8

Viscosity of Soluble Fiber Produced by GTF8117 or GTF6831

Solutions of chromatographically-purified soluble oligosaccharide fibers prepared as described in Example 3 and Example 5 were dried to a constant weight by lyophilization, and the resulting solids were used to prepare a 12 wt % solution of soluble fiber in distilled, deionized water. The viscosity of the soluble fiber solutions (reported in centipoise (cP), where 1 cP=1 millipascal-s (mPa-s)) (Table 7) was measured at 20° C. as described in the General Methods section.

TABLE 7

Viscosity of 12% (w/w) soluble oligosaccharide fiber solutions measured at 20° C.

| Example # | GTF | viscosity (cP) |
|---|---|---|
| 3 | GTF8117 | 5.3 |
| 5 | GTF6831 | 5.5 |

(ND = not determined).

Example 9

Digestibility of Soluble Fiber Produced by GTF8117 or GTF6831

Solutions of chromatographically-purified soluble oligosaccharide fibers prepared as described in Example 3 and Example 5 were dried to a constant weight by lyophilization. The digestibility test protocol was adapted from the Megazyme Integrated Total Dietary Fiber Assay (AOAC method 2009.01, Ireland). The final enzyme concentrations were kept the same as the AOAC method: 50 Unit/mL of pancreatic α-amylase (PAA), 3.4 Units/mL for amyloglucosidase (AMG). The substrate concentration in each reaction was 25 mg/mL as recommended by the AOAC method. The total volume for each reaction was 1 mL. Every sample was analyzed in duplicate with and without the treatment of the two digestive enzymes. The amount of released glucose was quantified by HPLC with the Aminex HPX-87C Columns (BioRad) as described in the General Methods. Maltodextrin (DE4-7, Sigma) was used as the positive control for the enzymes (Table 8).

TABLE 8

Digestibility of soluble oligosaccharide fiber.

| Example # | GTF | Digestibility (%) |
|---|---|---|
| 3 | GTF8117 | 0.0 |
| 5 | GTF6831 | 2.2 |

Example 10

Molecular Weight of Soluble Fiber Produced by GTF8117 or GTF6831

Solutions of soluble fibers purified by chromatography or by ultrafiltration prepared as described in Example 4 and Example 6 were dried to a constant weight by lyophilization, and the resulting solids were analyzed by SEC chromatography for number average molecular weight ($M_n$), weight average molecular weight ($M_w$), peak molecular weight ($M_p$), z-average molecular weight ($M_z$), and polydispersity index (PDI=$M_w/M_n$) as described in the General Methods section (Table 9)

TABLE 9

Characterization of soluble oligosaccharide fiber by SEC.

| Example # | GTF | Component (%) | $M_n$ (Daltons) | $M_w$ (Daltons) | $M_p$ (Daltons) | $M_z$ (Daltons) | PDI |
|---|---|---|---|---|---|---|---|
| 4 | GTF8117 | 100 | 16000 | 17100 | 15600 | 46800 | 1.07 |
| 6 | GTF6831 | 65 | 2508 | 3313 | 2406 | 4577 | 1.32 |
| 6 | GTF6831 | 35 | 615 | 709 | 799 | 793 | 1.15 |

Example 11

In Vitro Gas Production Using Soluble Oligosaccharide/Polysaccharide Fiber as Carbon Source Solutions of chromatographically-purified soluble oligosaccharide/polysaccharide fibers were dried to a constant weight by lyophilization. The individual soluble oligosaccharide/polysaccharide soluble fiber samples were subsequently evaluated as carbon source for in vitro gas production using the method described in the General Methods. PROMITOR® 85 (soluble corn fiber, Tate & Lyle), NUTRIOSE® FM06 (soluble corn fiber or dextrin, Roquette), FIBERSOL-2® 600F (digestion-resistant maltodextrin, Archer Daniels Midland Company & Matsutani Chemical), ORAFTI® GR (inulin from Beneo, Mannheim, Germany), LITESSE® Ultra™ (polydextrose, Danisco), GOS (galactooligosaccharide, Clasado Inc., Reading, UK), ORAFTI® P95 (oligofructose (fructooligosaccharide, FOS, Beneo), LACTITOL MC (4-O-β-D-Galactopyranosyl-D-glucitol monohydrate, Danisco) and glucose were included as control carbon sources. Table 10 lists the In vitro gas production by intestinal microbiota at 3 h and 24 h.

TABLE 10

In vitro gas production by intestinal microbiota.

| Sample | mL gas formation in 3 h | mL gas formation in 24 h |
|---|---|---|
| PROMITOR ® 85 | 2.6 | 8.5 |
| NUTRIOSE ® FM06 | 3.0 | 9.0 |
| FIBERSOL-2 ® 600F | 2.8 | 8.8 |
| ORAFTI ® GR | 3.0 | 7.3 |
| LITESSE ® ULTRA ™ | 2.3 | 5.8 |
| GOS | 2.6 | 5.2 |

TABLE 10-continued

In vitro gas production by intestinal microbiota.

| Sample | mL gas formation in 3 h | mL gas formation in 24 h |
|---|---|---|
| ORAFTI ® P95 | 2.6 | 7.5 |
| LACTITOL ® MC | 2.0 | 4.8 |
| Glucose | 2.4 | 5.2 |
| GTF6831 | 3.5 | 8.5 |
| GTF8117 | 3.0 | 6.7 |

Example 12

Colonic Fermentation Modeling and Measurement of Fatty Acids

Colonic fermentation was modeled using a semi-continuous colon simulator as described by Mäkivuokko et al. (*Nutri. Cancer* (2005) 52(1):94-104); in short; a colon simulator consists of four glass vessels which contain a simulated ileal fluid as described by Macfarlane et al. (*Microb. Ecol.* (1998) 35(2):180-187). The simulator is inoculated with a fresh human faecal microbiota and fed every third hour with new ileal liquid and part of the contents is transferred from one vessel to the next. The ileal fluid contains one of the described test components at a concentration of 1%. The simulation lasts for 48 h after which the content of the four vessels is harvested for further analysis. The further analysis involves the determination of microbial metabolites such as short chain fatty acids (SCFA); also referred to as volatile fatty acids (VFA) and branched chain fatty acids (BCFA). Analysis was performed as described by Holben et al. (*Microb. Ecol.* (2002) 44:175-185); in short; simulator content was centrifuged and the supernatant was used for SCFA and BCFA analysis. Pivalic acid (internal standard) and water were mixed with the supernatant and centrifuged. After centrifugation, oxalic acid solution was added to the supernatant and then the mixture was incubated at 4° C., and then centrifuged again. The resulting supernatant was analyzed by gas chromatography using a flame ionization detector and helium as the carrier gas. Comparative data generated from samples of LITESSE® ULTRA™ (polydextrose, Danisco), ORAFTI® P95 (oligofructose; fructooligosaccharide, "FOS", Beneo), lactitol (Lactitol MC (4-O-δ-D-galactopyranosyl-D-glucitol monohydrate, Danisco), and a negative control is also provided. The concentration of acetic, propionic, butyric, isobutyric, valeric, isovaleric, 2-methylbutyric, and lactic acid was determined (Table 11).

TABLE 11

Simulator metabolism and measurement of fatty acid production.

| Sample | Acetic (mM) | Propionic (mM) | Butyric (mM) | Lactic (mM) | Valeric (mM) | Short Chain Fatty Acids (SCFA) (mM) | Branched Chain Fatty Acids (BCFA) (mM) |
|---|---|---|---|---|---|---|---|
| GTF6831 | 69 | 30 | 60 | 1 | 3 | 161 | 3.8 |
| GTF8117 | 176 | 91 | 71 | 1 | 5 | 345 | 5.9 |
| Control | 83 | 31 | 40 | 3 | 6 | 163 | 7.2 |
| LITESSE ® polydextrose | 256 | 76 | 84 | 1 | 6 | 423 | 5.3 |
| FOS | 91 | 9 | 8 | 14 | — | 152 | 2.1 |
| Lactitol | 318 | 42 | 94 | 52 | — | 506 | 7.5 |

Example 13

Preparation of a Yogurt—Drinkable Smoothie

The following example describes the preparation of a yogurt—drinkable smoothie with the present fibers.

TABLE 12

| Ingredients | wt % |
|---|---|
| Distilled Water | 49.00 |
| Supro XT40 Soy Protein Isolate | 6.50 |
| Fructose | 1.00 |
| Grindsted A5D525, Danisco | 0.30 |
| Apple Juice Concentrate (70 Brix) | 14.79 |
| Strawberry Puree, Single Strength | 4.00 |
| Banana Puree, Single Strength | 6.00 |
| Plain Lowfat Yogurt-Greek Style, Cabot | 9.00 |
| 1% Red 40 Soln | 0.17 |
| Strawberry Flavor (DD-148-459-6) | 0.65 |
| Banana Flavor (#29513) | 0.20 |
| 75/25 Malic/Citric Blend | 0.40 |
| Present Soluble Fiber Sample | 8.00 |
| Total | 100.00 |

Step No. Procedure
  Pectin Solution Formation
1 Heat 50% of the formula water to 160° F. (~71.1° C.).
2 Disperse the pectin with high shear; mix for 10 minutes.
3 Add the juice concentrates and yogurt; mix for 5-10 minutes until the yogurt is dispersed.
  Protein Slurry
1 Into 50% of the batch water at 140° F. (60° C.), add the Supro XT40 and mix well.
2 Heat to 170° F. (~76.7° C.) and hold for 15 minutes.
3 Add the pectin/juice/yogurt slurry to the protein solution; mix for 5 minutes.
4 Add the fructose, fiber, flavors and colors; mix for 3 minutes.

5 Adjust the pH using phosphoric acid to the desired range (pH range 4.0-4.1).
6 Ultra High Temperature (UHT) process at 224° F. (106.7° C.) for 7 seconds with UHT homogenization after heating at 2500/500 psig (17.24/3.45 MPa) using the indirect steam (IDS) unit.
7 Collect bottles and cool in ice bath.
8 Store product in refrigerated conditions.

Example 14

Preparation of a Fiber Water Formulation

The following example describes the preparation of a fiber water with the present fibers.

TABLE 13

| Ingredient | wt % |
| --- | --- |
| Water, deionized | 86.41 |
| Pistachio Green #06509 | 0.00 |
| Present Soluble Fiber Sample | 8.00 |
| Sucrose | 5.28 |
| Citric Acid | 0.08 |
| Flavor (M748699M) | 0.20 |
| Vitamin C, ascorbic acid | 0.02 |
| TOTAL | 100.00 |

Step No. Procedure
1 Add dry ingredients and mix for 15 minutes.
2 Add remaining dry ingredients; mix for 3 minutes
3 Adjust pH to 3.0+/−0.05 using citric acid as shown in formulation.
4 Ultra High Temperature (UHT) processing at 224° F. (106.7° C.) for 7 seconds with homogenization at 2500/500 psig (17.24/3.45 MPa).
5 Collect bottles and cool in ice bath.
6 Store product in refrigerated conditions.

Example 15

Preparation of a Spoonable Yogurt Formulation

The following example describes the preparation of a spoonable yogurt with the present fibers.

TABLE 14

| Ingredient | wt % |
| --- | --- |
| Skim Milk | 84.00 |
| Sugar | 5.00 |
| Yogurt (6051) | 3.00 |
| Cultures (add to pH break point) | |
| Present Soluble Fiber | 8.00 |
| TOTAL | 100.00 |

Step No. Procedure
1 Add dry ingredients to base milk liquid; mix for 5 min.
2 Pasteurize at 195° F. (~90.6° C.) for 30 seconds, homogenize at 2500 psig (17.24 MPa), and cool to 105-110° F. (~40.6-43.3° C.).
3 Inoculate with culture; mix gently and add to water batch or hot box at 108° F. (~42.2° C.) until pH reaches 4.5-4.6. Fruit Prep Procedure 1 Add water to batch tank, heat to 140° F. (~60° C.).
2 Pre-blend carbohydrates and stabilizers. Add to batch tank and mix well.
3 Add Acid to reduce the pH to the desired range (target pH 3.5-4.0).
4 Add Flavor.
5 Cool and refrigerate.

Example 16

Preparation of a Model Snack Bar Formulation

The following example describes the preparation of a model snack bar with the present fibers.

TABLE 15

| Ingredients | wt % |
| --- | --- |
| Corn Syrup 63 DE | 15.30 |
| Present Fiber solution (70 Brix) | 16.60 |
| Sunflower Oil | 1.00 |
| Coconut Oil | 1.00 |
| Vanilla Flavor | 0.40 |
| Chocolate Chips | 7.55 |
| SUPRO ® Nugget 309 | 22.10 |
| Rolled Oats | 18.00 |
| Arabic Gum | 2.55 |
| Alkalized Cocoa Powder | 1.00 |
| Milk Chocolate Coating Compound | 14.50 |
| TOTAL | 100.00 |

Step No. Procedure
1 Combine corn syrup with liquid fiber solution. Warm syrup in microwave for 10 seconds.
2 Combine syrup with oils and liquid flavor in mixing bowl. Mix for 1 minute at speed 2.
3 Add all dry ingredient in bowl and mix for 45 seconds at speed 1.
4 Scrape and mix for another 30 seconds or till dough is mixed.
5 Melt chocolate coating.
6 Fully coat the bar with chocolate coating.

Example 17

Preparation of a High Fiber Wafer

The following example describes the preparation of a high fiber wafer with the present fibers.

TABLE 16

| Ingredients | wt % |
| --- | --- |
| Flour, white plain | 38.17 |
| Present fiber | 2.67 |
| Oil, vegetable | 0.84 |
| GRINSTED ® CITREM 2-in-1[1] citric acid ester made from sunflower or palm oil (emulsifier) | 0.61 |
| Salt | 0.27 |
| Sodium bicarbonate | 0.11 |
| Water | 57.33 |

[1]Danisco.

Step No. Procedure
1. High shear the water, oil and CITREM for 20 seconds.
2. Add dry ingredients slowly, high shear for 2-4 minutes.
3. Rest batter for 60 minutes.

4. Deposit batter onto hot plate set at 200° C. top and bottom, bake for 1 minute 30 seconds
5. Allow cooling pack as soon as possible.

Example 18

Preparation of a Soft Chocolate Chip Cookie

The following example describes the preparation of a soft chocolate chip cookie with the present fibers.

TABLE 17

| Ingredients | wt % |
|---|---|
| Stage 1 | |
| Lactitol, C | 16.00 |
| Cake margarine | 17.70 |
| Salt | 0.30 |
| Baking powder | 0.80 |
| Eggs, dried whole | 0.80 |
| Bicarbonate of soda | 0.20 |
| Vanilla flavor | 0.26 |
| Caramel flavor | 0.03 |
| Sucralose powder | 0.01 |
| Stage 2 | |
| Present Fiber Solution (70 brix) | 9.50 |
| water | 4.30 |
| Stage 3 | |
| Flour, pastry | 21.30 |
| Flour, high ratio cake | 13.70 |
| Stage Four | |
| Chocolate chips, 100% lactitol, sugar free | 15.10 |

Step No. Procedure
1. Cream together stage one, fast speed for 1 minute.
2. Blend stage two to above, slow speed for 2 minutes.
3. Add stage three, slow speed for 20 seconds.
4. Scrape down bowl; add stage four, slow speed for 20 seconds.
5. Divide into 30 g pieces, flatten, and place onto silicone lined baking trays.
6. Bake at 190° C. for 10 minutes approximately.

Example 19

Preparation of a Reduced Fat Short-Crust Pastry

The following example describes the preparation of a reduced fat short-crust pastry with the present fibers.

TABLE 18

| Ingredients | wt % |
|---|---|
| Flour, plain white | 56.6 |
| Water | 15.1 |
| Margarine | 11.0 |
| Shortening | 11.0 |
| Present fiber | 6.0 |
| Salt | 0.3 |

Step No. Procedure
1. Dry blend the flour, salt and present glucan fiber (dry)
2. Gently rub in the fat until the mixture resembles fine breadcrumbs.
3. Add enough water to make a smooth dough.

Example 20

Preparation of a Low Sugar Cereal Cluster

The following example describes the preparation of a low sugar cereal cluster with one of the present fibers.

TABLE 19

| Ingredients | wt % |
|---|---|
| Syrup Binder | 30.0 |
| Lactitol, MC 50% | |
| Present Fiber Solution (70 brix) 25% | |
| Water 25% | |
| Cereal Mix | 60.0 |
| Rolled Oats 70% | |
| Flaked Oats 10% | |
| Crisp Rice 10% | |
| Rolled Oats 10% | |
| Vegetable oil | 10.0 |

Step No. Procedure
1. Chop the fines.
2. Weight the cereal mix and add fines.
3. Add vegetable oil on the cereals and mix well.
4. Prepare the syrup by dissolving the ingredients.
5. Allow the syrup to cool down.
6. Add the desired amount of syrup to the cereal mix.
7. Blend well to ensure even coating of the cereals.
8. Spread onto a tray.
9. Place in a dryer/oven and allow to dry out.
10. Leave to cool down completely before breaking into clusters.

Example 21

Preparation of a Pectin Jelly

The following example describes the preparation of a pectin jelly with the present fibers.

TABLE 20

| Ingredients | wt % |
|---|---|
| Component A | |
| Xylitol | 4.4 |
| Pectin | 1.3 |
| Component B | |
| Water | 13.75 |
| Sodium citrate | 0.3 |
| Citric Acid, anhydrous | 0.3 |
| Component C | |
| Present Fiber Solution (70 brix) | 58.1 |
| Xylitol | 21.5 |
| Component D | |
| Citric acid | 0.35 |
| Flavor, Color | q.s. |

Step No. Procedure
1. Dry blend the pectin with the xylitol (Component A).
2. Heat Component B until solution starts to boil.
3. Add Component A gradually, and then boil until completely dissolved.
4. Add Component C gradually to avoid excessive cooling of the batch.
5. Boil to 113° C.

6. Allow to cool to <100° C. and then add colour, flavor and acid (Component D). Deposit immediately into starch molds.
7. Leave until firm, then de-starch.

Example 22

Preparation of a Chewy Candy

The following example describes the preparation of a chewy candy with the present fibers.

TABLE 21

| Ingredients | wt % |
|---|---|
| Present glucan fiber | 35 |
| Xylitol | 35 |
| Water | 10 |
| Vegetable fat | 4.0 |
| Glycerol Monostearate (GMS) | 0.5 |
| Lecithin | 0.5 |
| Gelatin 180 bloom (40% solution) | 4.0 |
| Xylitol, CM50 | 10.0 |
| Flavor, color & acid | q.s. |

Step No. Procedure
1. Mix the present glucan fiber, xylitol, water, fat, GMS and lecithin together and then cook gently to 158° C.
2. Cool the mass to below 90° C. and then add the gelatin solution, flavor, color and acid.
3. Cool further and then add the xylitol CM. Pull the mass immediately for 5 minutes.
4. Allow the mass to cool again before processing (cut and wrap or drop rolling).

Example 23

Preparation of a Coffee—Cherry Ice Cream

The following example describes the preparation of a coffee-cherry ice cream with the present fibers.

TABLE 22

| Ingredients | wt % |
|---|---|
| Fructose, C | 8.00 |
| Present glucan fiber | 10.00 |
| Skimmed milk powder | 9.40 |
| Anhydrous Milk Fat (AMF) | 4.00 |
| CREMODAN ® SE 709 Emulsifier & Stabilizer System[1] | 0.65 |
| Cherry Flavoring U35814[1] | 0.15 |
| Instant coffee | 0.50 |
| Tri-sodium citrate | 0.20 |
| Water | 67.10 |

[1]Danisco.

Step No. Procedure
1. Add the dry ingredients to the water, while agitating vigorously.
2. Melt the fat.
3. Add the fat to the mix at 40° C.
4. Homogenize at 200 bar/70-75° C.
5. Pasteurize at 80-85° C./20-40 seconds.
6. Cool to ageing temperature (5° C.).
7. Age for minimum 4 hours.
8. Add flavor to the mix.
9. Freeze in continuous freezer to desired overrun (100% is recommended).
10. Harden and storage at −25° C.

What is claimed is:

1. A soluble α-glucan fiber composition, said soluble α-glucan fiber composition comprising:
   (a) an α-(1,6) linkage consisting of at least 95% α-(1,6) glycosidic linkages;
   (b) 1% or less α-(1,3) glycosidic linkages;
   (c) less than 2% α-(1,3,6) glycosidic linkages; and
   (d) less than 1.5% α-(1,4) glycosidic linkages; and said soluble α-glucan fiber has
   (e) a weight average molecular weight of less than 20000 Daltons;
   (f) a viscosity of less than 0.25 Pascal second (Pa·s) at 12 wt % in water at 20° C.;
   (g) a dextrose equivalence (DE) in the range of 1 to 30;
   (h) a digestibility of less than 12% as measured by the Association of Analytical Communities (AOAC) method 2009.01;
   (i) a solubility of at least 20% (w/w) in pH 7 water at 25° C.; and
   (j) a polydispersity index of less than 5.

2. A carbohydrate composition comprising: 0.01 to 99 wt % (dry solids basis) of the soluble α-glucan fiber composition of claim 1.

3. The carbohydrate composition of claim 2 further comprising: a monosaccharide, a disaccharide, glucose, sucrose, fructose, leucrose, corn syrup, high fructose corn syrup, isomerized sugar, maltose, trehalose, panose, raffinose, cellobiose, isomaltose, honey, maple sugar, a fruit-derived sweetener, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, a resistant maltodextrin, a branched maltodextrin, inulin, polydextrose, a fructooligosaccharide, a galactooligosaccharide, an isomaltooligosaccharide, a xylooligosaccharide, an arabinoxylooligosaccharide, a nigerooligosaccharide, a gentiooligosaccharide, a filler, an excipient, or a binder.

4. A food product comprising the soluble α-glucan fiber composition of claim 1 or the carbohydrate composition of claim 2 or 3.

5. A cosmetic composition, a pharmaceutical composition or a low carcinogenicity composition comprising the soluble α-glucan fiber composition of claim 1.

6. A food composition suitable for consumption by animals comprising the soluble α-glucan fiber composition of claim 1.

7. A composition comprising 0.01 to 99 wt % (dry solids basis) of the soluble α-glucan fiber composition of claim 1 and an additional agent selected from a synbiotic, a peptide, a peptide hydrolysate, a protein, a protein hydrolysate, a soy protein, a dairy protein, an amino acid, a polyol, a polyphenol, a vitamin, a mineral, an herbal, an herbal extract, a fatty acid, a polyunsaturated fatty acid (PUFAs), a phytosteroid, betaine, a carotenoid, a digestive enzyme, or a probiotic organism.

* * * * *